United States Patent
Speeg et al.

(10) Patent No.: US 10,905,403 B2
(45) Date of Patent: Feb. 2, 2021

(54) PRESENTATION OF BIOPSY SAMPLE BY BIOPSY DEVICE

(71) Applicant: Devicor Medical Products, Inc., Cincinnati, OH (US)

(72) Inventors: Trevor W. V. Speeg, Williamsburg, OH (US); Gavin M. Monson, Oxford, OH (US); John A. Hibner, Mason, OH (US); Andrew P. Nock, Dayton, OH (US); Shailendra K. Parihar, Mason, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 897 days.

(21) Appl. No.: 15/099,104

(22) Filed: Apr. 14, 2016

(65) Prior Publication Data

US 2016/0228106 A1  Aug. 11, 2016

Related U.S. Application Data

(63) Continuation of application No. 11/942,807, filed on Nov. 20, 2007, now Pat. No. 9,345,457.
(Continued)

(51) Int. Cl.
*A61B 10/02* (2006.01)
*A61B 10/00* (2006.01)

(52) U.S. Cl.
CPC ...... *A61B 10/0266* (2013.01); *A61B 10/0096* (2013.01); *A61B 10/0275* (2013.01);
(Continued)

(58) Field of Classification Search
CPC ............ A61B 10/0096; A61B 10/0266; A61B 10/0275; A61B 10/0283; A61B 2010/0208; A61B 2010/0225
See application file for complete search history.

(56) References Cited

U.S. PATENT DOCUMENTS 3,630,192 A  12/1971  Jamshidi
3,732,858 A  5/1973  Banko
(Continued)

FOREIGN PATENT DOCUMENTS

AU  2007242954  7/2008
AU  2013200957  3/2013
(Continued)

OTHER PUBLICATIONS

Chinese Office Action dated Nov. 23, 2016 for Application No. CN 201210470709.9, 8 pgs.
(Continued)

*Primary Examiner* — Patrick Fernandes
(74) *Attorney, Agent, or Firm* — Frost Brown Todd LLC

(57) ABSTRACT

A biopsy device includes a cutter defining a cutter lumen and a tissue sample holder for collecting tissue samples. In one example, the tissue sample holder includes a rotatable manifold, and has a plurality of chambers that are each configured to separately hold tissue samples. A tissue sample holder rotation mechanism is operable to rotate the manifold to successively align each of the chambers with the cutter lumen. A controller in communication with the rotation mechanism is configured to rotate the manifold to a presentation position to present a collected tissue sample within a chamber to a user (e.g., at an angular position approximately 90 degrees from the cutter lumen). The controller is further configured to rotate the manifold align the next, empty chamber with the cutter lumen in response to a user input instructing the biopsy device to obtain another tissue sample.

20 Claims, 69 Drawing Sheets

Related U.S. Application Data

(60) Provisional application No. 60/874,792, filed on Dec. 13, 2006, provisional application No. 60/869,736, filed on Dec. 13, 2006.

(52) U.S. Cl.
 CPC .. *A61B 10/0283* (2013.01); *A61B 2010/0208* (2013.01); *A61B 2010/0225* (2013.01)

(56) References Cited

U.S. PATENT DOCUMENTS

| | | |
|---|---|---|
| 3,734,099 A | 5/1973 | Bender et al. |
| 3,889,657 A | 6/1975 | Baumgarten |
| 3,945,375 A | 3/1976 | Banko |
| 3,996,935 A | 12/1976 | Banko |
| 4,038,988 A | 8/1977 | Perisse |
| 4,051,852 A | 10/1977 | Villari |
| 4,083,706 A | 4/1978 | Wiley |
| 4,203,444 A | 5/1980 | Bonnell et al. |
| 4,257,425 A | 3/1981 | Ryan |
| 4,316,465 A | 2/1982 | Dotson, Jr. |
| 4,320,761 A | 3/1982 | Haddad |
| 4,368,734 A | 1/1983 | Banko |
| 4,393,879 A | 7/1983 | Milgrom |
| 4,517,977 A | 5/1985 | Frost |
| 4,554,473 A | 11/1985 | Muller |
| 4,600,014 A | 7/1986 | Beraha |
| 4,650,460 A * | 3/1987 | Roizenblatt ......... A61F 9/00763 604/22 |
| 4,782,833 A | 11/1988 | Einhorn et al. |
| 4,919,146 A | 4/1990 | Rhinehart et al. |
| RE33,258 E | 7/1990 | Onik et al. |
| 4,989,614 A | 2/1991 | Dejter, Jr. et al. |
| 4,995,877 A | 2/1991 | Ams et al. |
| 5,047,008 A | 9/1991 | de Juan, Jr. et al. |
| 5,108,381 A | 4/1992 | Kolozsi |
| 5,112,299 A | 5/1992 | Pascaloff |
| 5,133,359 A | 7/1992 | Kedem |
| 5,197,484 A | 3/1993 | Kornberg et al. |
| 5,213,110 A | 5/1993 | Kedem et al. |
| 5,217,478 A | 6/1993 | Rexroth |
| 5,217,479 A | 6/1993 | Shuler |
| 5,226,909 A | 7/1993 | Evans et al. |
| 5,231,110 A | 7/1993 | Seele et al. |
| 5,234,000 A | 8/1993 | Hakky et al. |
| 5,249,121 A | 9/1993 | Baum et al. |
| 5,275,609 A | 1/1994 | Pingleton et al. |
| 5,290,303 A | 3/1994 | Pingleton et al. |
| 5,295,980 A | 3/1994 | Ersek |
| 5,312,425 A | 5/1994 | Evans et al. |
| 5,320,110 A | 6/1994 | Wang |
| 5,320,635 A | 6/1994 | Smith |
| 5,341,816 A | 8/1994 | Allen |
| 5,353,804 A | 10/1994 | Kornberg et al. |
| 5,403,276 A | 4/1995 | Schechter et al. |
| 5,415,169 A | 5/1995 | Siczek et al. |
| 5,423,844 A | 6/1995 | Miller |
| 5,424,625 A | 6/1995 | Haner |
| 5,431,645 A | 7/1995 | Smith et al. |
| 5,432,065 A | 7/1995 | Fuller |
| 5,455,766 A * | 10/1995 | Scheller ............... A61B 17/32 606/4 |
| 5,505,210 A | 4/1996 | Clement |
| 5,520,635 A | 5/1996 | Gelbfish |
| 5,526,822 A * | 6/1996 | Burbank ............ A61B 10/0266 600/567 |
| 5,543,695 A | 8/1996 | Culp et al. |
| 5,580,347 A | 12/1996 | Reimels |
| 5,601,585 A | 2/1997 | Banik et al. |
| 5,643,304 A | 7/1997 | Schechter et al. |
| 5,645,209 A | 7/1997 | Green et al. |
| 5,649,547 A | 7/1997 | Ritchart et al. |
| 5,669,923 A | 9/1997 | Gordon |
| 5,685,840 A | 11/1997 | Schechter et al. |
| 5,689,159 A | 11/1997 | Culp et al. |
| 5,769,086 A | 6/1998 | Ritchart et al. |
| 5,775,333 A | 7/1998 | Burbank et al. |
| 5,791,908 A | 8/1998 | Gillio |
| 5,804,936 A | 9/1998 | Brodsky et al. |
| 5,823,998 A | 10/1998 | Yamagata |
| 5,848,978 A | 12/1998 | Cecchi |
| 5,871,454 A | 2/1999 | Majlessi |
| 5,876,329 A | 3/1999 | Harhen |
| 5,910,139 A | 6/1999 | Cochran et al. |
| 5,913,857 A | 6/1999 | Ritchart et al. |
| 5,928,164 A | 7/1999 | Burbank et al. |
| 5,944,673 A | 8/1999 | Gregoire et al. |
| 5,964,716 A | 10/1999 | Gregoire et al. |
| 5,976,164 A | 11/1999 | Bencini et al. |
| 5,980,469 A | 11/1999 | Burbank et al. |
| 6,007,497 A | 12/1999 | Huitema |
| 6,013,956 A | 1/2000 | Anderson, Jr. |
| 6,017,316 A | 1/2000 | Ritchart et al. |
| 6,019,733 A | 2/2000 | Farascioni |
| 6,050,955 A | 4/2000 | Bryan et al. |
| 6,061,446 A | 5/2000 | Lester et al. |
| 6,077,230 A | 6/2000 | Gregoire et al. |
| 6,080,113 A | 6/2000 | Heneveld et al. |
| 6,086,544 A | 7/2000 | Hibner et al. |
| 6,096,042 A | 8/2000 | Herbert |
| 6,106,512 A | 8/2000 | Cochran et al. |
| 6,120,462 A * | 9/2000 | Hibner ............... A61B 10/0275 600/566 |
| 6,120,733 A | 9/2000 | Goodman et al. |
| 6,142,955 A | 11/2000 | Farascioni et al. |
| 6,142,956 A | 11/2000 | Kortenbach et al. |
| 6,162,187 A | 12/2000 | Buzzard et al. |
| 6,213,957 B1 | 4/2001 | Milliman et al. |
| 6,228,055 B1 | 5/2001 | Forester et al. |
| 6,231,522 B1 | 5/2001 | Voegele et al. |
| 6,245,084 B1 | 6/2001 | Mark et al. |
| 6,273,862 B1 | 8/2001 | Privitera et al. |
| 6,346,107 B1 | 2/2002 | Cucin |
| 6,409,970 B1 | 6/2002 | Phifer |
| 6,428,487 B1 | 8/2002 | Burdorff et al. |
| 6,432,065 B1 | 8/2002 | Burdoff et al. |
| 6,485,436 B1 | 11/2002 | Truckai et al. |
| 6,527,731 B2 | 3/2003 | Weiss et al. |
| 6,544,194 B1 | 4/2003 | Kortenback et al. |
| 6,585,664 B2 | 7/2003 | Burdorff et al. |
| 6,592,530 B1 | 7/2003 | Farhadi |
| 6,602,227 B1 | 8/2003 | Cimino et al. |
| 6,620,111 B2 | 9/2003 | Stephens et al. |
| 6,626,849 B2 | 9/2003 | Huitema et al. |
| 6,626,850 B1 | 9/2003 | Cha et al. |
| 6,638,235 B2 | 10/2003 | Miller et al. |
| 6,656,428 B1 | 12/2003 | Clark et al. |
| 6,659,338 B1 | 12/2003 | Dittmann et al. |
| 6,712,774 B2 | 3/2004 | Voegele et al. |
| 6,722,392 B1 | 4/2004 | David et al. |
| 6,749,576 B2 | 6/2004 | Bauer |
| 6,752,768 B2 | 6/2004 | Burdorff et al. |
| 6,758,824 B1 | 7/2004 | Miller et al. |
| 6,849,080 B2 | 2/2005 | Lee et al. |
| 6,852,108 B2 | 2/2005 | Barry et al. |
| 6,904,305 B2 | 6/2005 | Tsekos |
| 6,923,809 B2 | 8/2005 | Eggers et al. |
| 6,986,748 B2 | 1/2006 | McAlister et al. |
| 6,993,375 B2 | 1/2006 | Burbank et al. |
| 6,996,433 B2 | 2/2006 | Burbank et al. |
| 6,996,443 B2 | 2/2006 | Marshall et al. |
| 7,001,341 B2 | 2/2006 | Gellman et al. |
| 7,025,098 B2 | 4/2006 | Osborne |
| 7,025,732 B2 | 4/2006 | Thompson et al. |
| 7,047,063 B2 | 5/2006 | Burbank et al. |
| 7,053,586 B2 | 5/2006 | Jones |
| 7,108,660 B2 | 9/2006 | Stephens et al. |
| 7,153,274 B2 | 12/2006 | Stephens et al. |
| 7,156,815 B2 | 1/2007 | Leigh et al. |
| 7,204,811 B2 | 4/2007 | Kortenbach et al. |
| 7,226,424 B2 | 6/2007 | Ritchart et al. |
| 7,229,419 B2 | 6/2007 | Hancock |
| 7,229,439 B2 | 6/2007 | Burbank et al. |

(56) References Cited

U.S. PATENT DOCUMENTS

| | | |
|---|---|---|
| 7,252,641 B2 | 8/2007 | Thompson et al. |
| 7,276,032 B2 | 10/2007 | Hibner |
| 7,335,216 B2 | 2/2008 | Bender |
| 7,372,510 B2 | 5/2008 | Abileah |
| 7,419,472 B2 | 9/2008 | Hibner et al. |
| 7,438,692 B2 | 10/2008 | Tsonton et al. |
| 7,442,171 B2 | 10/2008 | Stephens et al. |
| 7,465,279 B2 | 12/2008 | Beckman et al. |
| 7,488,295 B2 | 2/2009 | Burbank et al. |
| 7,508,610 B2 | 3/2009 | Kosugi et al. |
| 7,510,534 B2 | 3/2009 | Burdoff et al. |
| 7,517,322 B2 | 4/2009 | Weikel et al. |
| 7,575,556 B2 | 8/2009 | Speeg et al. |
| 7,641,668 B2 | 1/2010 | Perry et al. |
| 7,645,240 B2 | 1/2010 | Thompson et al. |
| 7,648,466 B2 | 1/2010 | Stephens et al. |
| 7,736,382 B2 | 6/2010 | Webb et al. |
| 7,740,597 B2 | 6/2010 | Cicenas et al. |
| 7,753,857 B2 | 7/2010 | Hibner |
| 7,758,515 B2 | 7/2010 | Hibner |
| 7,794,409 B2 | 9/2010 | Damarati |
| 7,806,834 B2 | 10/2010 | Beckman et al. |
| 7,806,835 B2 | 10/2010 | Hibner et al. |
| 7,828,745 B2 | 11/2010 | McAlister et al. |
| 7,828,748 B2 | 11/2010 | Hibner |
| 7,837,632 B2 | 11/2010 | Stephens et al. |
| 7,846,107 B2 | 12/2010 | Hoffman et al. |
| 7,854,706 B2 | 12/2010 | Hibner |
| 7,854,707 B2 | 12/2010 | Hibner et al. |
| 7,858,038 B2 | 12/2010 | Andreyko et al. |
| 7,867,173 B2 | 1/2011 | Hibner et al. |
| 7,893,817 B2 | 2/2011 | Kim |
| 7,896,817 B2 | 3/2011 | Garrison |
| 7,914,464 B2 | 3/2011 | Burdorff et al. |
| 7,918,804 B2 | 4/2011 | Monson et al. |
| 7,938,786 B2 | 5/2011 | Ritchie et al. |
| 7,981,049 B2 | 7/2011 | Ritchie et al. |
| 8,002,713 B2 | 8/2011 | Heske et al. |
| 8,016,772 B2 | 9/2011 | Heske et al. |
| 8,052,616 B2 | 11/2011 | Andreisek et al. |
| 8,083,687 B2 | 12/2011 | Parihar |
| 8,105,849 B2 | 1/2012 | McDevitt et al. |
| 8,109,885 B2 | 2/2012 | Heske et al. |
| 8,118,755 B2 | 2/2012 | Hibner et al. |
| 8,124,128 B2 | 2/2012 | Ladner et al. |
| 8,172,773 B2 | 5/2012 | Heske et al. |
| 8,206,316 B2 | 6/2012 | Hibner et al. |
| 8,241,226 B2 | 8/2012 | Hibner et al. |
| 8,251,916 B2 | 8/2012 | Speeg et al. |
| 8,454,531 B2 | 6/2013 | Speeg et al. |
| 8,480,595 B2 | 7/2013 | Speeg et al. |
| 8,485,987 B2 | 7/2013 | Videbaek et al. |
| 8,622,924 B2 | 1/2014 | Speeg et al. |
| 8,702,623 B2 | 4/2014 | Parihar et al. |
| 8,764,680 B2 | 7/2014 | Rhad et al. |
| 8,801,742 B2 | 8/2014 | Rhad et al. |
| 8,858,465 B2 | 10/2014 | Fiebig |
| 8,932,233 B2 | 1/2015 | Haberstich et al. |
| 8,938,285 B2 | 1/2015 | Fiebig et al. |
| 8,968,212 B2 | 3/2015 | Speeg et al. |
| 9,039,634 B2 | 5/2015 | Speeg et al. |
| 9,095,326 B2 | 8/2015 | Ritchie et al. |
| 9,326,755 B2 | 5/2016 | Fiebig et al. |
| 9,345,457 B2 | 5/2016 | Speeg et al. |
| 9,414,814 B2 | 8/2016 | Hibner et al. |
| 9,433,403 B2 | 9/2016 | Speeg et al. |
| 9,486,184 B2 | 11/2016 | Hibner et al. |
| 9,968,339 B2 | 5/2018 | Hibner et al. |
| 2001/0014776 A1 | 8/2001 | Oriol et al. |
| 2002/0120212 A1 | 8/2002 | Ritchart et al. |
| 2002/0193656 A1 | 12/2002 | Ravins et al. |
| 2003/0199753 A1 | 10/2003 | Hibner et al. |
| 2005/0004559 A1 | 1/2005 | Quick et al. |
| 2005/0049521 A1 | 3/2005 | Miller et al. |
| 2005/0082518 A1 | 4/2005 | Kunitz |
| 2005/0256445 A1 | 11/2005 | Cucin |
| 2006/0074345 A1 | 4/2006 | Hibner |
| 2006/0085759 A1 | 4/2006 | Knapheide |
| 2006/0282012 A1 | 12/2006 | McAlister et al. |
| 2007/0010738 A1 | 1/2007 | Mark et al. |
| 2007/0055173 A1 | 3/2007 | DeLonzor et al. |
| 2007/0191732 A1 | 8/2007 | Voegele |
| 2007/0213632 A1 | 9/2007 | Okazaki et al. |
| 2007/0270714 A1 | 11/2007 | Cushner et al. |
| 2008/0004545 A1 | 1/2008 | Garrison |
| 2008/0221479 A1 | 9/2008 | Ritchie et al. |
| 2009/0131819 A1 | 5/2009 | Ritchie et al. |
| 2009/0131821 A1 | 5/2009 | Speeg et al. |
| 2009/0192408 A1 | 7/2009 | Mark |
| 2010/0152610 A1 | 6/2010 | Parihar et al. |
| 2010/0160819 A1 | 6/2010 | Parihar et al. |
| 2012/0116246 A1 | 5/2012 | Hibner et al. |
| 2013/0245494 A1 | 9/2013 | Speeg et al. |
| 2013/0324882 A1 | 12/2013 | Mescher |
| 2014/0039343 A1 | 2/2014 | Mescher et al. |
| 2016/0228102 A1 | 4/2016 | Speeg et al. |
| 2016/0228105 A1 | 4/2016 | Speeg et al. |
| 2018/0221002 A1 | 8/2018 | Mescher et al. |

FOREIGN PATENT DOCUMENTS

| | | |
|---|---|---|
| AU | 2013200958 | 3/2013 |
| CA | 2672664 A1 | 6/2008 |
| CA | 2644140 A1 | 5/2009 |
| CN | 1745515 A | 3/2006 |
| CN | 102961168 A | 3/2013 |
| EP | 0 378 692 | 7/1990 |
| EP | 1 074 271 | 2/2001 |
| EP | 1 040 790 | 10/2002 |
| EP | 1 642 534 A2 | 4/2006 |
| EP | 1642533 A1 | 4/2006 |
| EP | 1 815 815 | 8/2007 |
| EP | 1 832 234 | 9/2007 |
| EP | 1 932 481 | 6/2008 |
| EP | 2 062 535 A1 | 5/2009 |
| EP | 2 062 537 A1 | 5/2009 |
| EP | 2 120 724 A2 | 11/2009 |
| GB | 2018601 | 10/1979 |
| JP | 2000316867 | 11/2000 |
| JP | 200695313 | 4/2006 |
| JP | 2008504915 | 2/2008 |
| JP | 2009532081 | 9/2009 |
| JP | 5722380 B2 | 5/2015 |
| WO | WO 1990/08508 | 8/1990 |
| WO | WO 1993/14707 | 8/1993 |
| WO | WO 1995/25465 | 9/1995 |
| WO | WO 1997/24991 | 7/1997 |
| WO | WO 1998/06338 | 2/1998 |
| WO | WO 1998/25556 | 6/1998 |
| WO | WO 1998/33436 | 8/1998 |
| WO | WO 2000/030531 | 6/2000 |
| WO | WO 2003/077768 | 9/2003 |
| WO | WO 2004/016177 | 2/2004 |
| WO | WO 2006/005342 | 1/2006 |
| WO | WO 2006/005344 | 1/2006 |
| WO | WO 2006/038634 | 4/2006 |
| WO | WO 2007/019152 | 2/2007 |
| WO | WO 2007/112751 | 10/2007 |
| WO | WO 2008/076712 | 6/2008 |

OTHER PUBLICATIONS

Defendants' Final Invalidity Contentions, dated Sep. 11, 2009, *Ethicon Endo-Surgery, Inc.* v. *Hologic, Inc., et al.;* Case No. 1:07-cv-00834; US District Court, Southern District of Ohio.

Defendants' Identification of Prior Art, dated Dec. 31, 2009, *Ethicon Endo-Surgery, Inc.* v. *Hologic, Inc., et al.;* Case No. 1:07-cv-00834; US District Court, Southern District of Ohio.

Defendants' Preliminary Invalidity Contentions, dated Apr. 25, 2008, *Ethicon Endo-Surgery, Inc.* v. *Hologic, Inc., et al.;* Case No. 1:07-cv-00834; US District Court, Southern District of Ohio.

(56) References Cited

OTHER PUBLICATIONS

Defendants' Supplemental Preliminary Invalidity Contentions, dated Jul. 25, 2008, *Ethicon Endo-Surgery, Inc.* v. *Hologic, Inc., et al.;* Case No. 1:07-cv-00834; US District Court, Southern District of Ohio.
Defendants' Third Supplemental Preliminary Invalidity Contentions, dated Dec. 31, 2009, *Ethicon Endo-Surgery, Inc.* v. *Hologic, Inc., et al.;* Case No. 1:07-cv-00834; US District Court, Southern District of Ohio.
EnCor MRI Specifications and Breast Biopsy System, SenoRx (2005) p. 102.
Mamotome MR Biopsy System Operator's Manual, Ethicon Endo-Surgery, Inc., Cincinnati, Ohio (2006) pp. 1-86.
Parker et al., "From the RSNA Refresher Courses: Performing a Breast Biopsy with a Directional, Vacuum-assisted Biopsy Instrument," *RadioGraphics 1997;* 17 (RSNA 1997) pp. 1233-1252.
Parker, et al., "Stereotactic Breast Biopsy with a Biopsy Gun," Radiology 1990; 176 (RSNA 1990) pp. 741-747.
Transcript of Testimony by Dr. David Lipson on 2/12/20010, at trial; *Ethicon Endo-Surgery, Inc.* v. *Hologic, Inc., et al.;* Case No. 1:07-cv-00834; US District Court, Southern District of Ohio.
Van Berkel, C., "55.1: 3D Touchless Display Interaction," SID 02 Digest, pp. 1410-1413.
Australian First Examination Report dated Jan. 24, 2014 for Application No. AU 2013200958.
Australian Notice of Acceptance, dated Feb. 27, 2015 for Application No. AU 2013200958, 3pgs.
Australian First Examination Report dated Mar. 25, 2014 for Application No. AU 2013201864.
Australian Notice of Acceptance dated May 28, 2015 for Application No. AU 2013201864.
Australian First Examination Report dated Jun. 24, 2014 for Application No. AU 2013202934.
Australian Notice of Acceptance dated Jul. 20, 2015 for Application No. AU 2013202934.
Australian Patent Examination Report No. 1, dated Jan. 29, 2014 for Application No. AU 2013200957, 4pgs.
Australian Notice of Acceptance, dated Feb. 17, 2015 for Application No. AU 2013200957, 2 pgs.
Australian Patent Examination Report No. 1, dated Jan. 31, 2014 for Application No. 2013201295.
Canadian Office Action dated Apr. 24, 2015 for Application No. CA 2,644,140.
Canadian Office Action dated Nov. 13, 2014 for Application No. CA 2,672,664, 6 pgs.
Chinese First Office Action dated Dec. 19, 2013 for Application No. 201210367531.5.
Chinese Second Office Action dated Sep. 9, 2014 for Application No. CN 20120367531.5.
Chinese Office Action dated Feb. 28, 2014 for Application No. CN 201210470709.9.
Chinese Office Action dated Dec. 1, 2014 for Application No. CN 201210470709.9.
Chinese Office Action dated Jun. 17, 2015 for Application No. CN 201210470709.9.
Chinese Office Action dated Nov. 20, 2013 for Application No. CN 20121007979.2.
Chinese Office Action dated Apr. 7, 2014 for Application No. CN 20121007979.2.
Chinese Office Action dated Nov. 15, 2014for Application No. CN 20121007979.2.
Chinese Office Action dated Apr. 15, 2015 for Application No. CN 20121007979.2.
European Communication, dated Oct. 20, 2010 for Application No. EP 08 253 776.2, 9pgs.
European Communication, dated Apr. 14, 2011 for Application No. EP 08 253 776.2, 1 pg.
European Search Report dated Dec. 11, 2007 for Application No. EP 07253220.
European Search Report dated Mar. 9, 2009 for Application No. EP 08253774.
European Search Report dated Mar. 9, 2009 for Application No. EP 08253775.
European Search Report dated Mar. 9, 2009 for Application No. EP 08253781.
European Search Report dated Mar. 10, 2009 for Application No. EP 08253776.
International Search Report dated Jul. 18, 2007 for Application No. PCT/US2006/030022.
Japanese Office Action dated Jun. 11, 2014 for Application No. JP 2013-090053, 7 pgs.
Japanese Office Action dated Sep. 9, 2014 for Application No. JP 2013-253905.
Japanese Office Action dated Sep. 12, 2014 for Application No. JP 2013-253905.
Japanese Office Action dated Sep. 24, 2014 for Application No. JP 2013-215367.
Japanese Office Action dated May 29, 2015 for Application No. JP 2013-215367.
U.S. Non-Final Rejection dated Mar. 20, 2008 for U.S. Appl. No. 11/782,963.
U.S. Final Rejection dated Sep. 26, 2008 for U.S. Appl. No. 11/782,963.
U.S. Non-Final Rejection dated Apr. 4, 2008 for U.S. Appl. No. 11/739,117.
U.S. Appl. No. 60/869,736, filed Dec. 13, 2006.
U.S. Appl. No. 60/874,792, filed Dec. 13, 2006.
U.S. Appl. No. 13/869,490.
Canadian Office Action dated Dec. 18, 2015 for Application No. CA 2,672,664, 3 pgs.
Chinese Office Action dated Dec. 17, 2015 for Application No. CN 201210470709.9, 20 pgs.
Chinese Appeal Board Opinion dated Jun. 7, 2016 for Application No. CN 201210470709.9, 12 pgs.
Chinese Office Action dated Mar. 16, 2017 for Application No. CN 201210470709.9, 8 pgs.
European Search Report and Written Opinion dated Jan. 3, 2019 for Application No. EP 18195987.5, 8 pgs.
Canadian Office Action dated May 28, 2018 for Application No. CA 2,969,611, 4 pgs.
Chinese Patent Reexamination Board Decision, Reversal of Rejection Decision, dated Sep. 9, 2016 for Application No. CN 201210470709. 9, 35 pgs.
Chinese Office Action, Notification of Allowance, dated Jun. 26, 2017 for Application No. CN 201210470709.9, 1 pg.
U.S. Office Action, Non-Final, dated Oct. 6, 2008 for U.S. Appl. No. 11/736,117, 6 pgs.
U.S. Appl. No. 61/566,793, filed Dec. 5, 2011.
U.S. Appl. No. 11/942,816; Ritchie et al. filed Nov. 20, 2007.
U.S. Appl. No. 11/942,919; Speeg et al. filed Nov. 20, 2007.
U.S. Appl. No. 15/099,080; Speeg et al. filed Apr. 14, 2016.
U.S. Appl. No. 15/099,093; Speeg et al. filed Apr. 14, 2016.
Brazilian Pre-Examination Office Action dated Feb. 15, 2019 for Application No. PI0806158-0, 4 pgs.
Brazilian Pre-Examination Office Action dated Feb. 15, 2019 for Application No. PI0806161-0, 4 pgs.
Brazilian Pre-Examination Office Action dated Feb. 15, 2019 for Application No. PI0806162-9, 4 pgs.
Canadian Office Action dated Apr. 16, 2019 for Application No. CA 2,969,611, 4 pgs.

* cited by examiner

PRESENTATION OF BIOPSY SAMPLE BY BIOPSY DEVICE

This application is a continuation of U.S. patent application Ser. No. 11/942,807, entitled "Presentation of Biopsy Sample by Biopsy Device," filed Nov. 11, 2007, published as U.S. Pub. No. 2008/0214955 on Sep. 4, 2008, which claims priority to U.S. Provisional Patent App. No. 60/874,792, entitled "Biopsy Sample Storage," filed Dec. 13, 2006. U.S. patent application Ser. No. 11/942,807 also claims priority to U.S. Provisional Patent App. No. 60/869,736, entitled "Biopsy System," filed Dec. 13, 2006.

BACKGROUND

Biopsy samples have been obtained in a variety of ways in various medical procedures using a variety of devices. Biopsy devices may be used under stereotactic guidance, ultrasound guidance, MRI guidance, or otherwise. Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2007/0118048, entitled "Remote Thumbwheel for a Surgical Biopsy Device," published May 24, 2007; U.S. Provisional Patent Application Ser. No. 60/869,736, entitled "Biopsy System," filed Dec. 13, 2006; and U.S. Provisional Patent Application Ser. No. 60/874,792, entitled "Biopsy Sample Storage," filed Dec. 13, 2006. The disclosure of each of the above-cited U.S. Patents, U.S. Patent Application Publications, and U.S. Provisional Patent Applications is incorporated by reference herein. While several systems and methods have been made and used for obtaining a biopsy sample, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
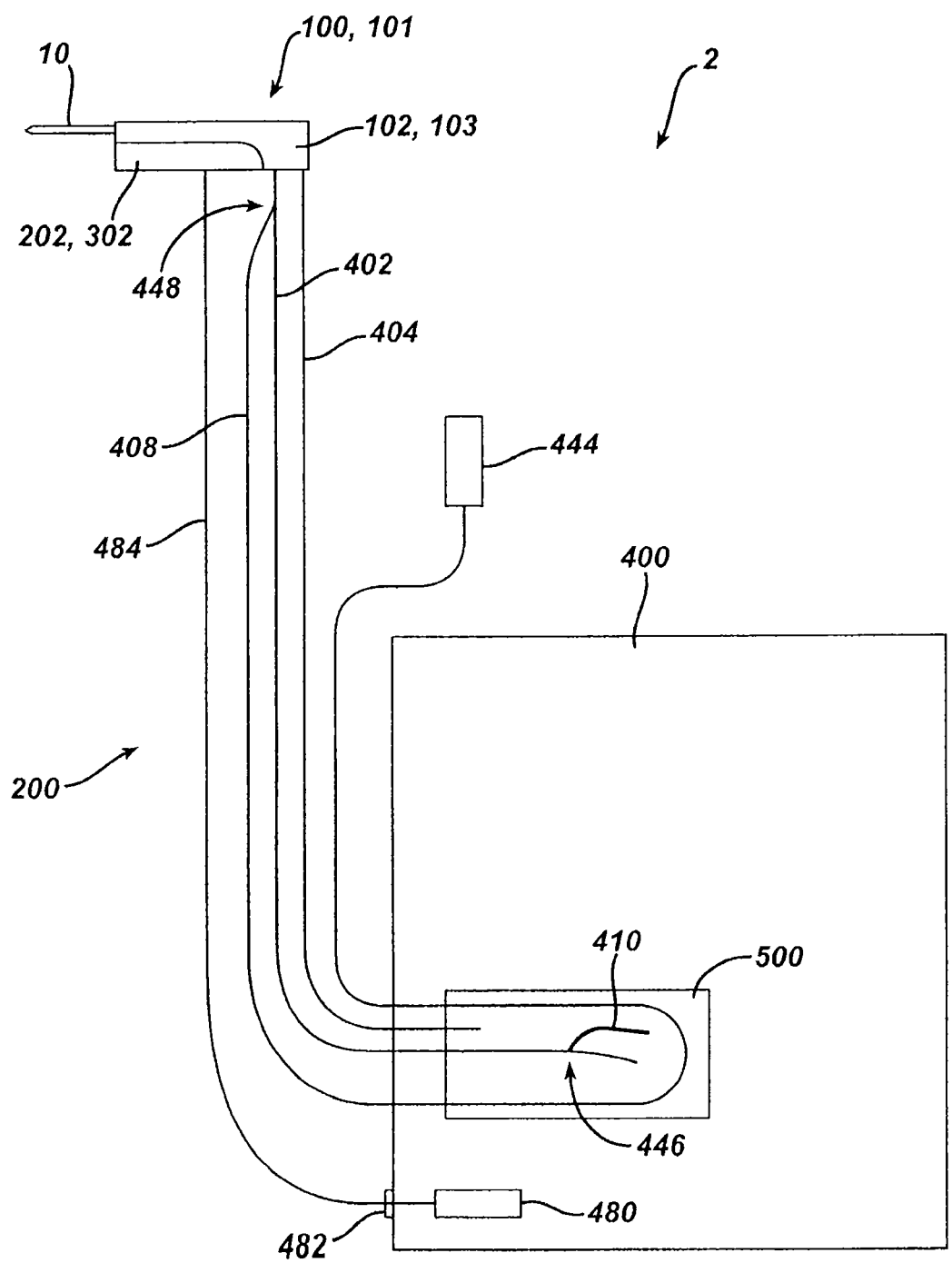
FIG. 1 depicts a schematic view of an exemplary biopsy system.
Figure 2:
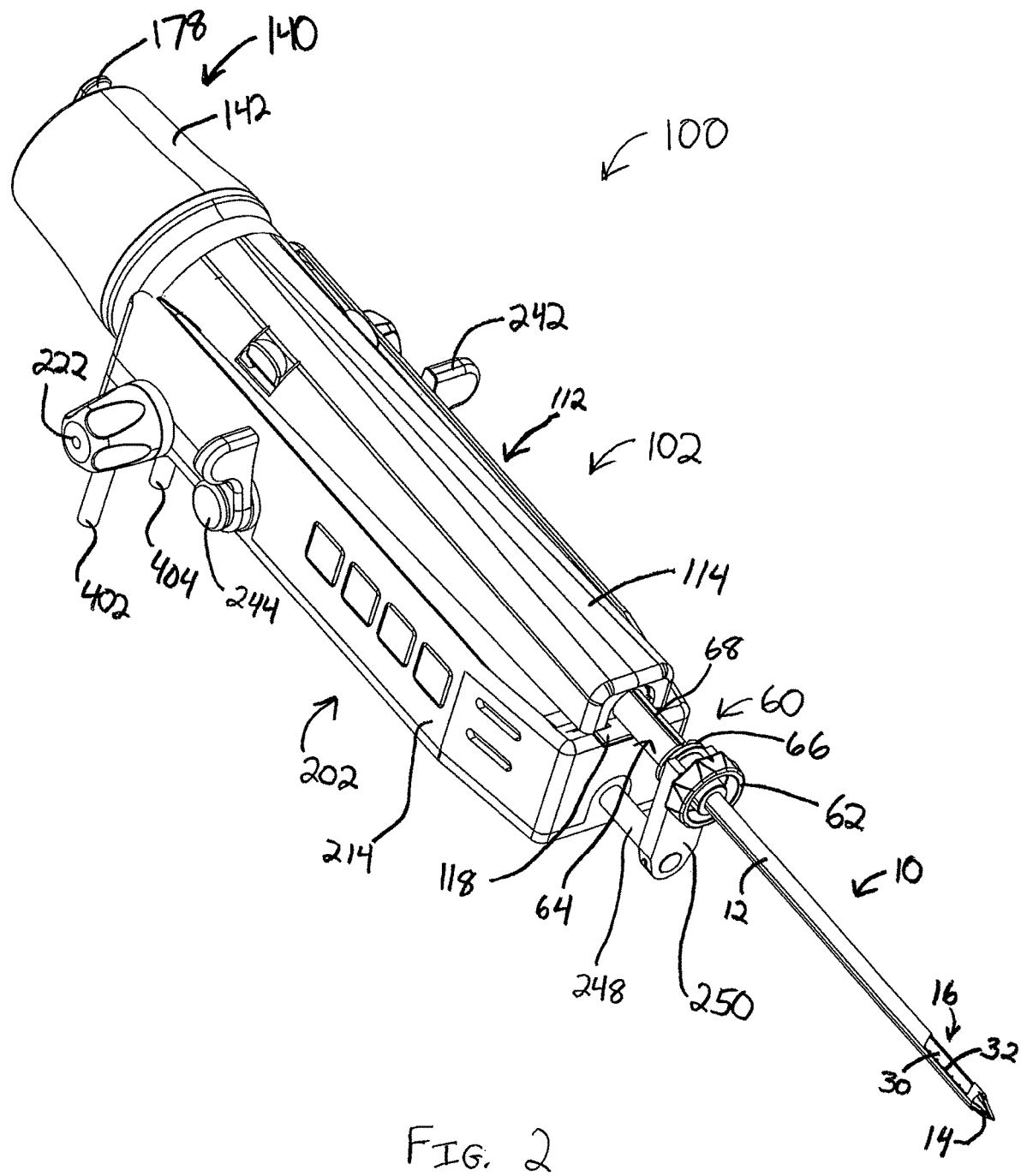
FIG. 2 depicts a perspective view of an exemplary assembled biopsy device, for use in a stereotactic setting.
Figure 3:
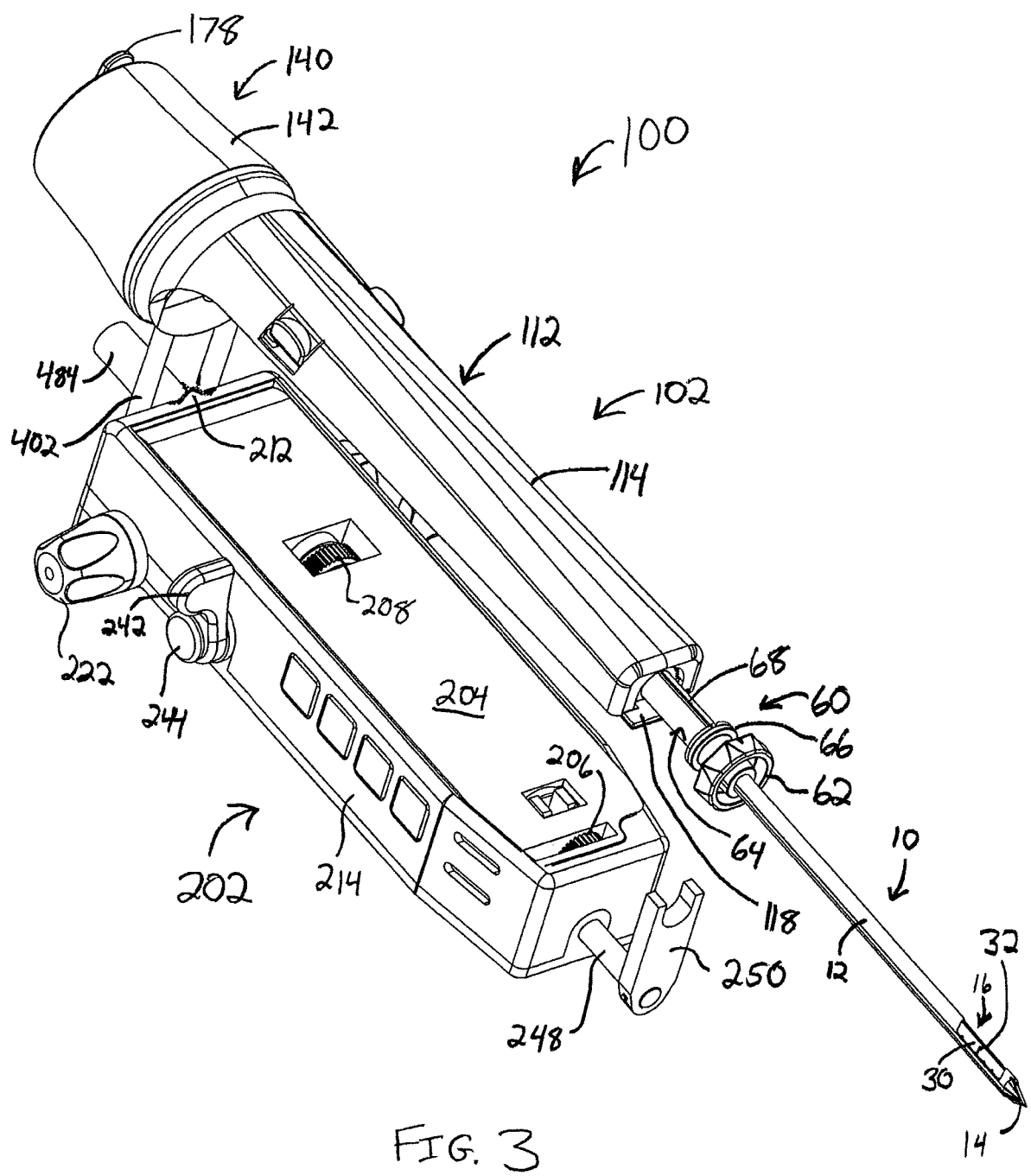
FIG. 3 depicts an exploded view of the biopsy device of FIG. 2, with the probe detached from the holster.
Figure 4:
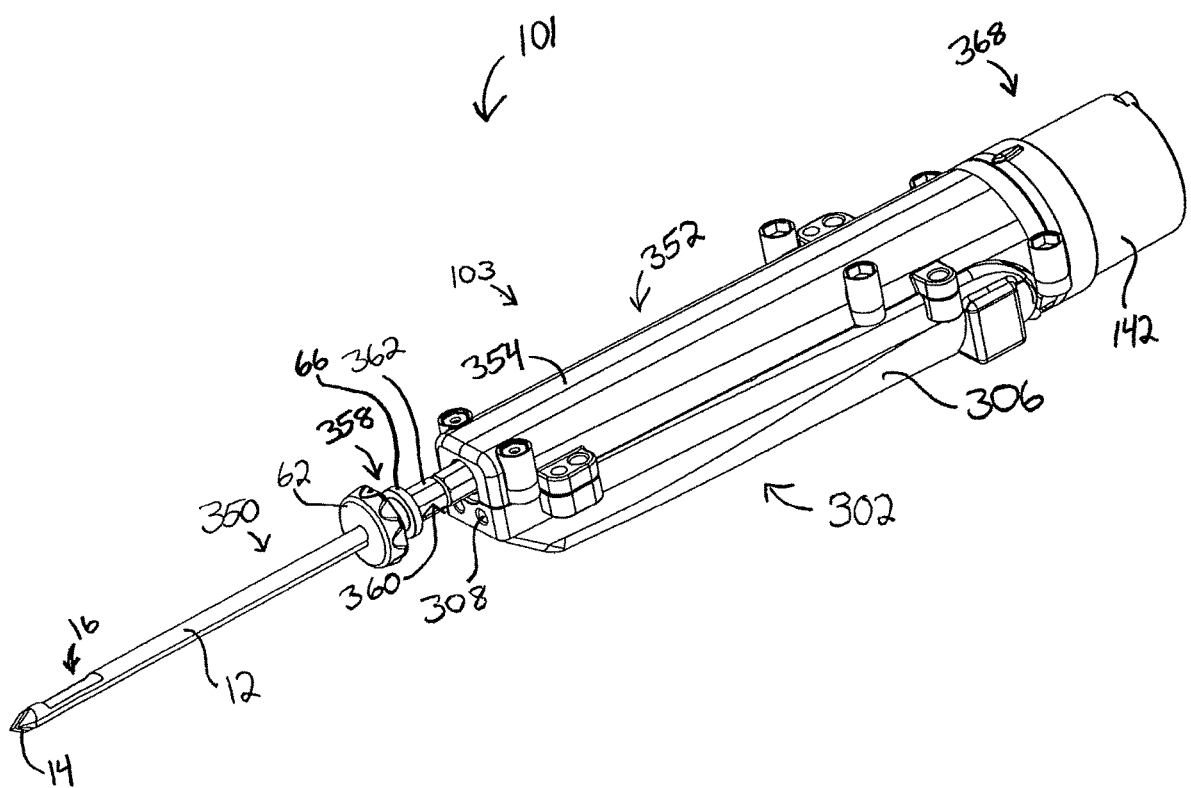
FIG. 4 depicts a perspective view of an exemplary assembled biopsy device, for use in an ultrasound setting.
Figure 5:
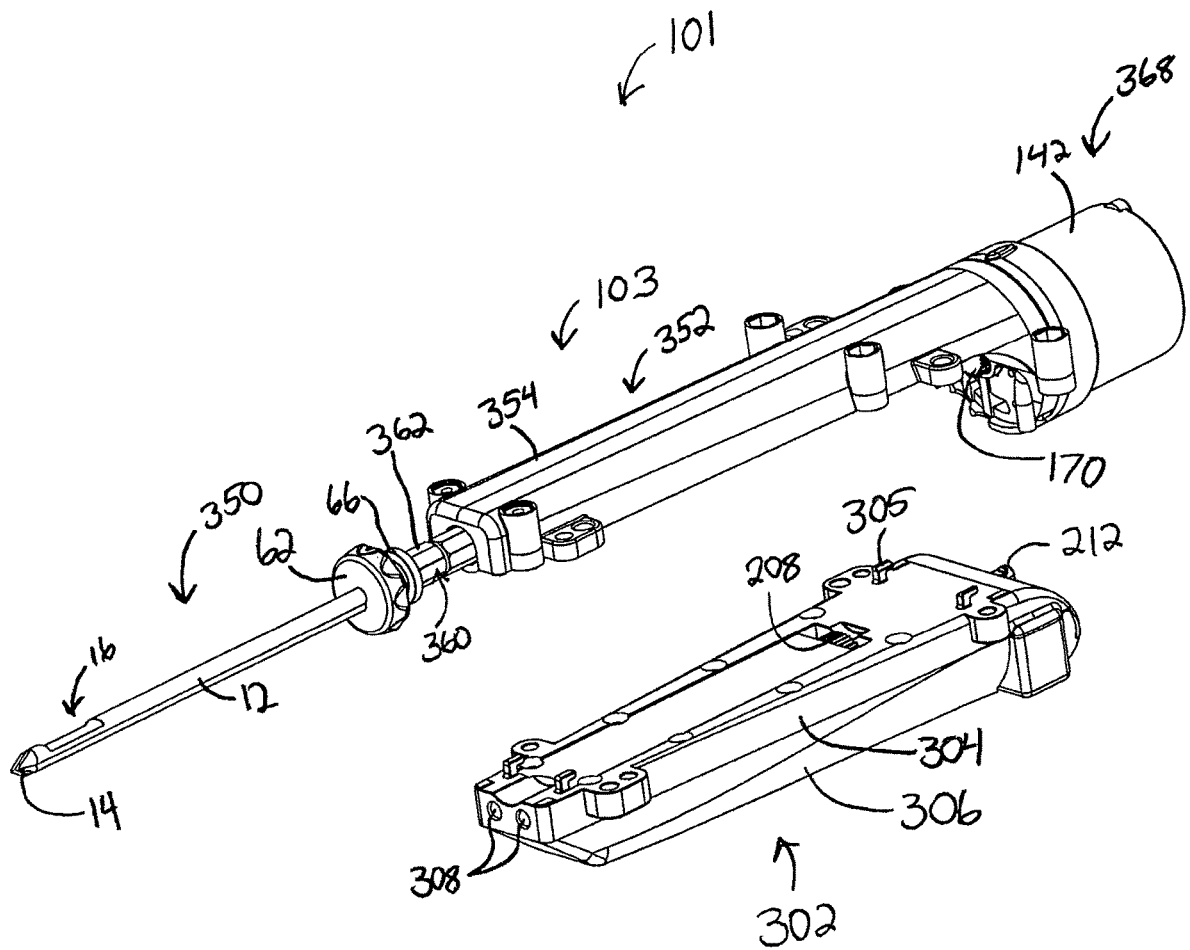
FIG. 5 depicts an exploded view of the biopsy device of FIG. 4, with the probe detached from the holster.
Figure 6:
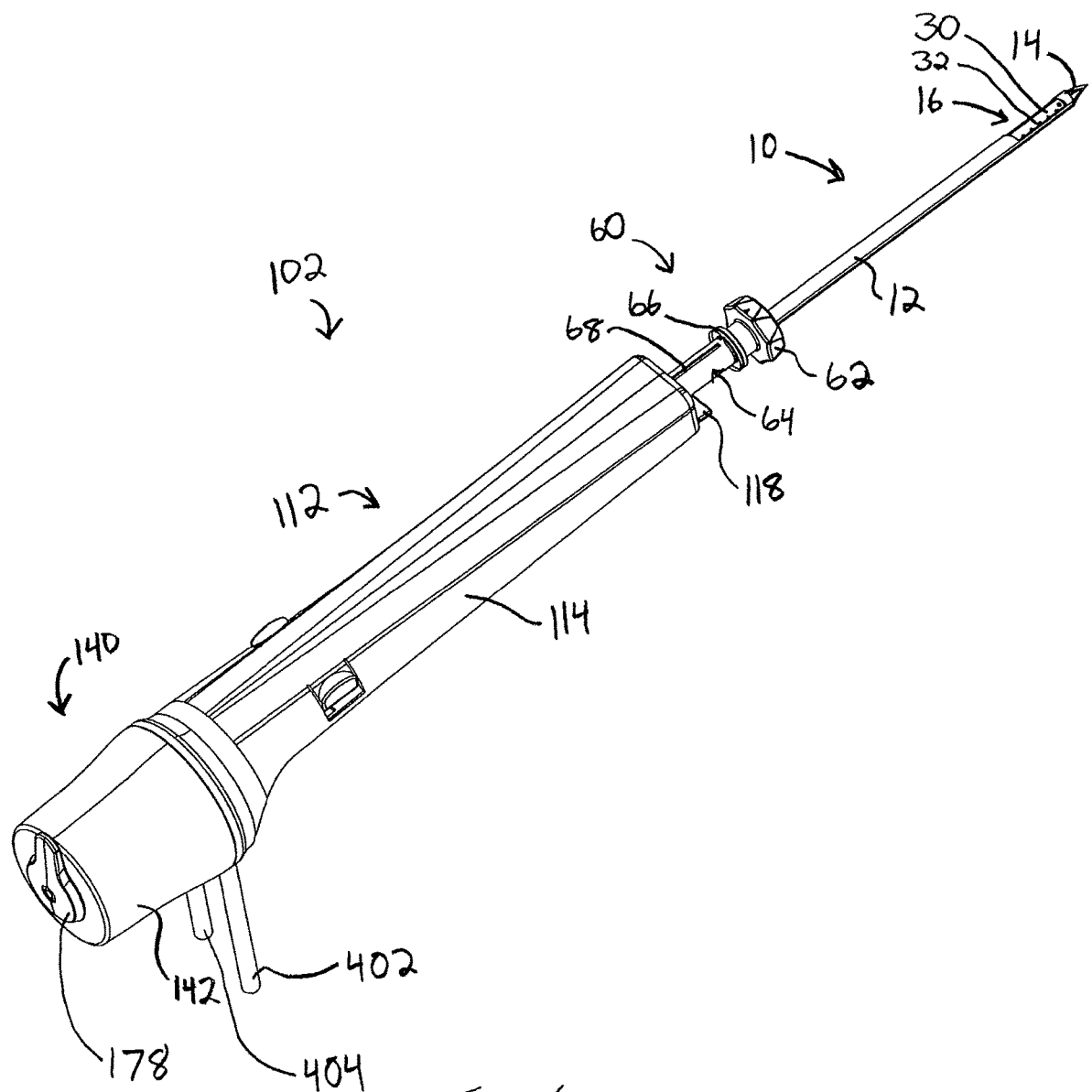
FIG. 6 depicts a top perspective view of a probe portion of the biopsy device of FIG. 3.
Figure 7:
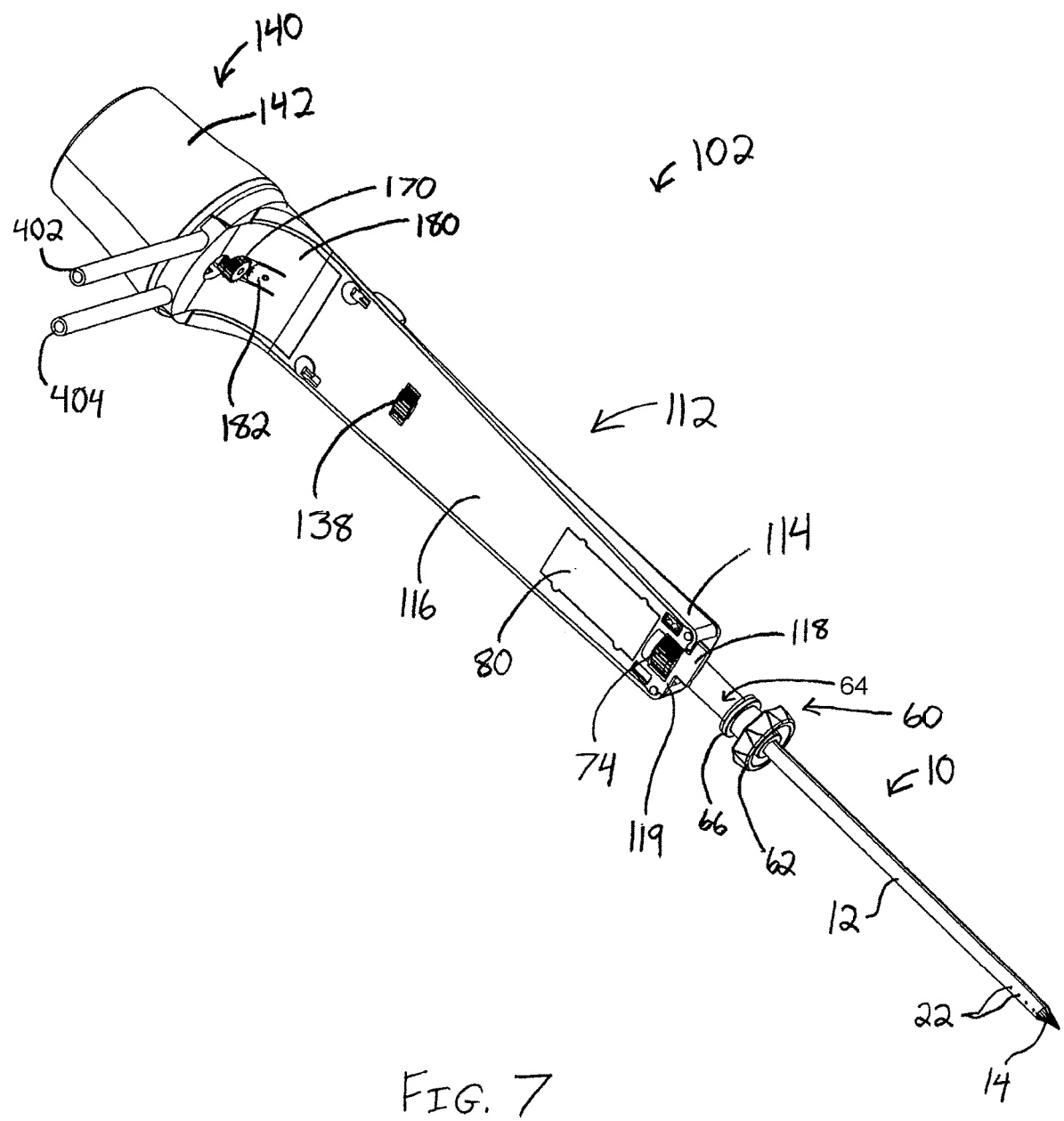
FIG. 7 depicts a bottom perspective view of the probe portion of FIG. 6.
Figure 8:
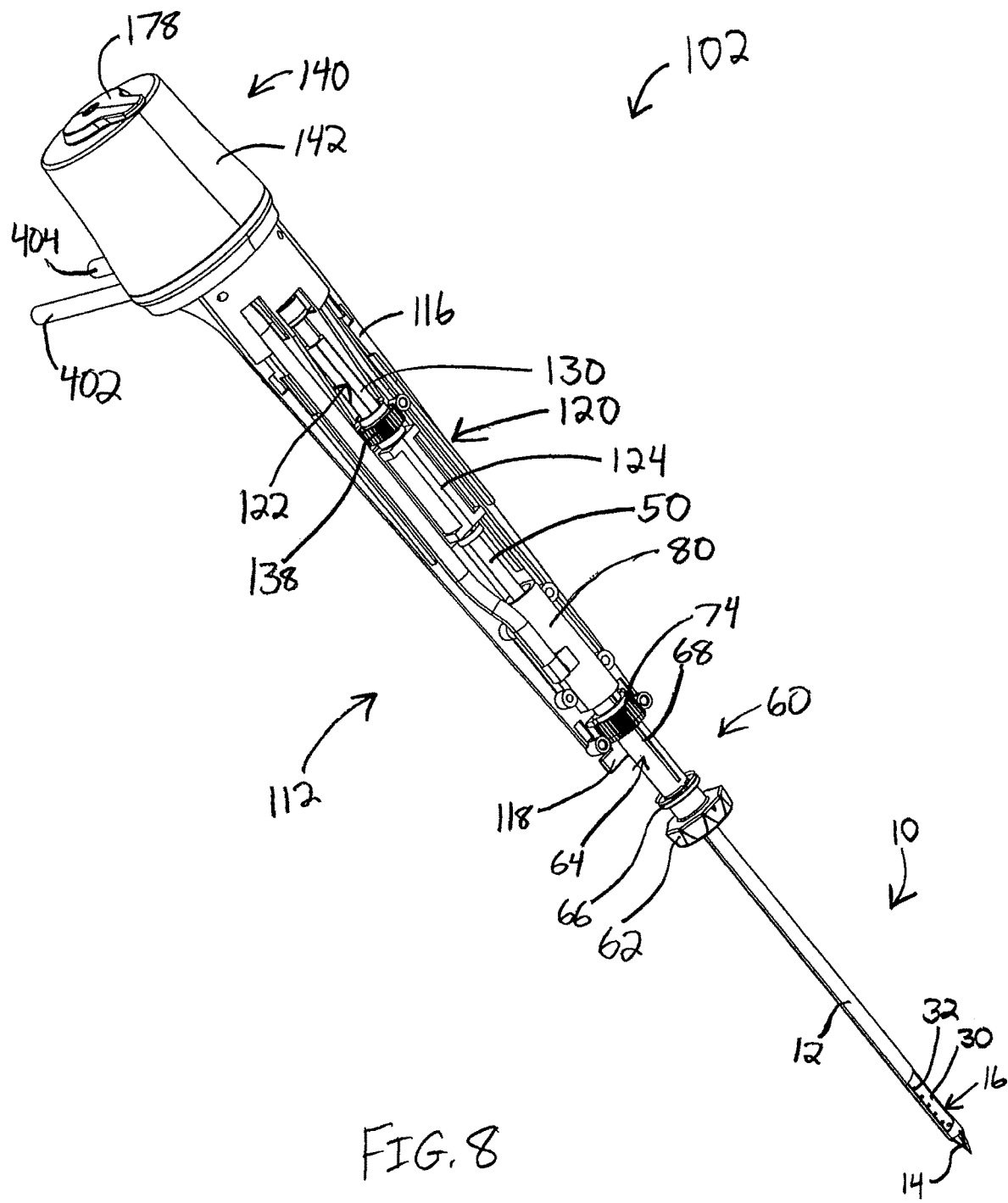
FIG. 8 depicts a top perspective view of the probe portion of FIG. 6, with a top cover removed.
Figure 9:
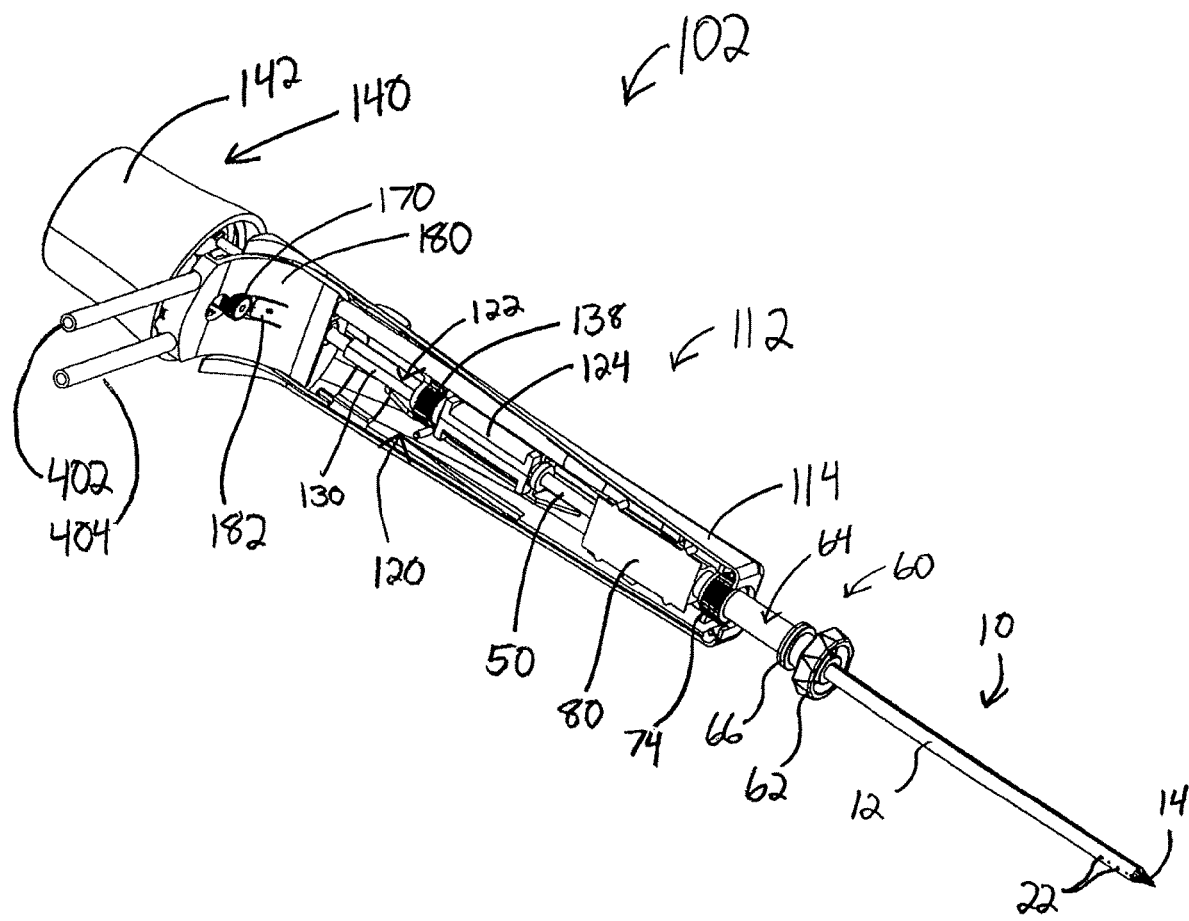
FIG. 9 depicts a bottom perspective view of the probe portion of FIG. 6, with a base removed.
Figure 10:
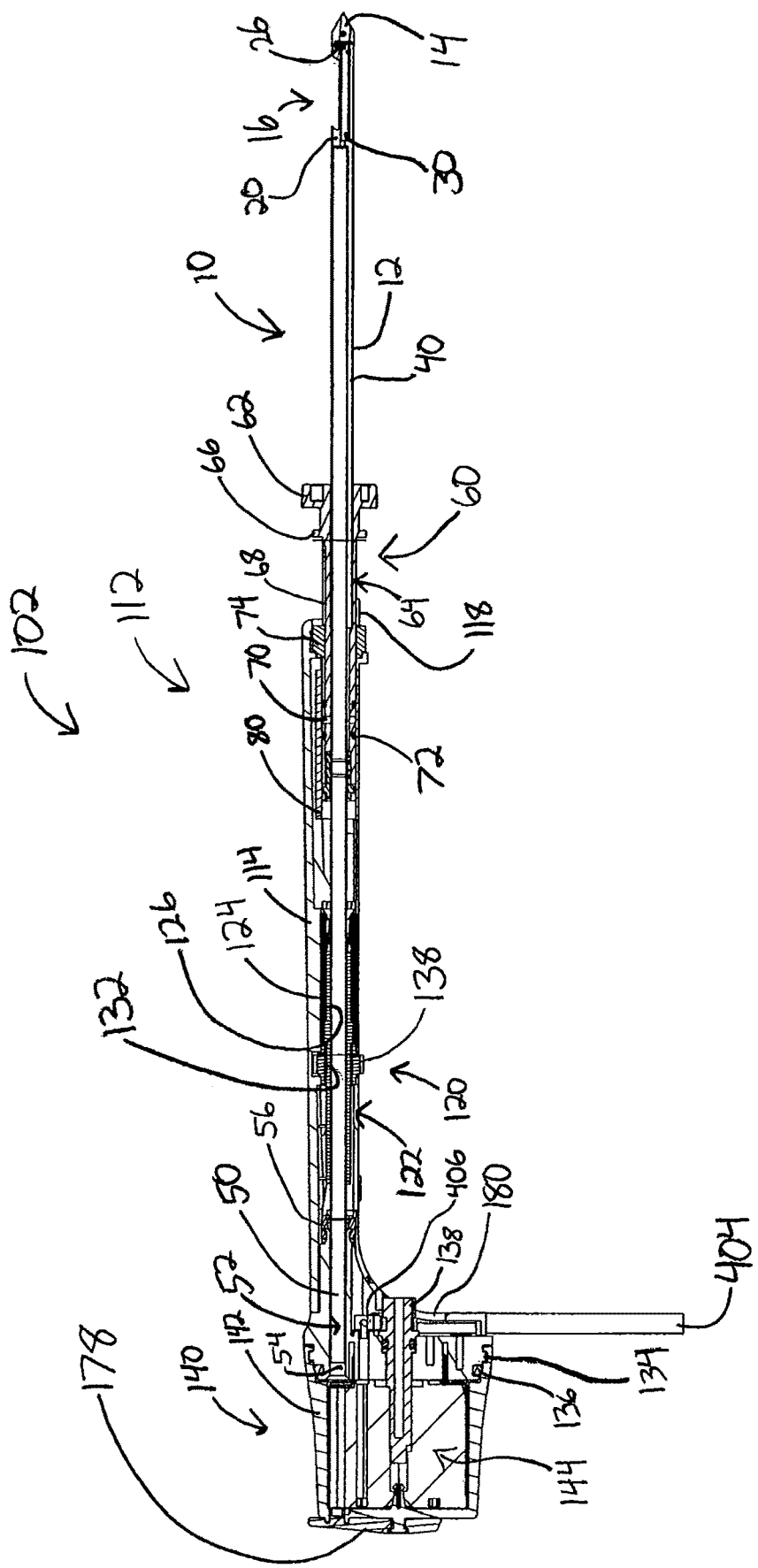
FIG. 10 depicts a lateral cross-sectional view of the probe portion of FIG. 6, taken along a longitudinal plane.

As shown in FIG. 1, an exemplary biopsy system (2) includes a biopsy device (100, 101) and a vacuum control module (400). As shown in FIGS. 2-3, biopsy device (100) comprises a probe (102) and a holster (202). Similarly, as shown in FIGS. 4-5, biopsy device (101) comprises a probe (103) and a holster (302). As will be described in greater detail below, each probe (102, 103) is separable from its corresponding holster (202, 302). Use of the term "holster" herein should not be read as requiring any portion of probe (102, 103) to be inserted into any portion of holster (202, 302). Indeed, in some variations of biopsy devices (100, 101), probe (102, 103) may simply sit on holster (202, 302). In some other variations, a portion of holster (202, 302) may be inserted into probe (102, 103). Furthermore, in some biopsy devices (100, 101), probe (102, 103) and holster (202, 302) may be of unitary or integral construction, such that the two components cannot be separated. Still other suitable structural and functional relationships between probe (102, 103) and holster (202, 302) will be apparent to those of ordinary skill in the art in view of the teachings herein.

Some variations of biopsy devices (100, 101) may include one or more sensors (not shown), in probe (102, 103) and/or in holster (202, 302), that is/are configured to detect when probe (102, 103) is coupled with holster (202, 302). Such sensors or other features may further be configured to permit only certain types of probes (102, 103) and holsters (202, 302) to be coupled together. In addition or in the alternative, such sensors may be configured to disable one or more functions of probes (102, 103) and/or holsters (202, 302) until a suitable probe (102, 103) and holster (202, 302) are coupled together. Of course, such sensors and features may be varied or omitted as desired.

By way of example only, probe (102, 103) may be provided as a disposable component, while holster (202, 302) may be provided as a reusable component. Vacuum control module (400) is provided on a cart (not shown) in the present example, though like other components described herein, a cart is merely optional. Among other components described herein, a footswitch (not shown) and/or other devices may be used to provide at least some degree of control of at least a portion of biopsy system (2). Conduits (200) provide communication of power (e.g., electrical, pneumatic, etc.), control signals, saline, vacuum, and venting from vacuum control module (400) to biopsy device (100, 101). Each of these components will be described in greater detail below.

I. Exemplary Probe for Stereotactic Use

As shown in FIGS. 6-14, probe (102) comprises a needle portion (10) and a body portion (112). Body portion (112) comprises a cover member (114) and a base member (116).

A tissue sample holder (140) is removably secured to base member (116), though tissue sample holder (140) may alternatively be secured to cover member (114) or some other component. As will be described in greater detail below, a pair of tubes (402, 404) are coupled with probe (102).

A. Exemplary Needle

Figure 11:
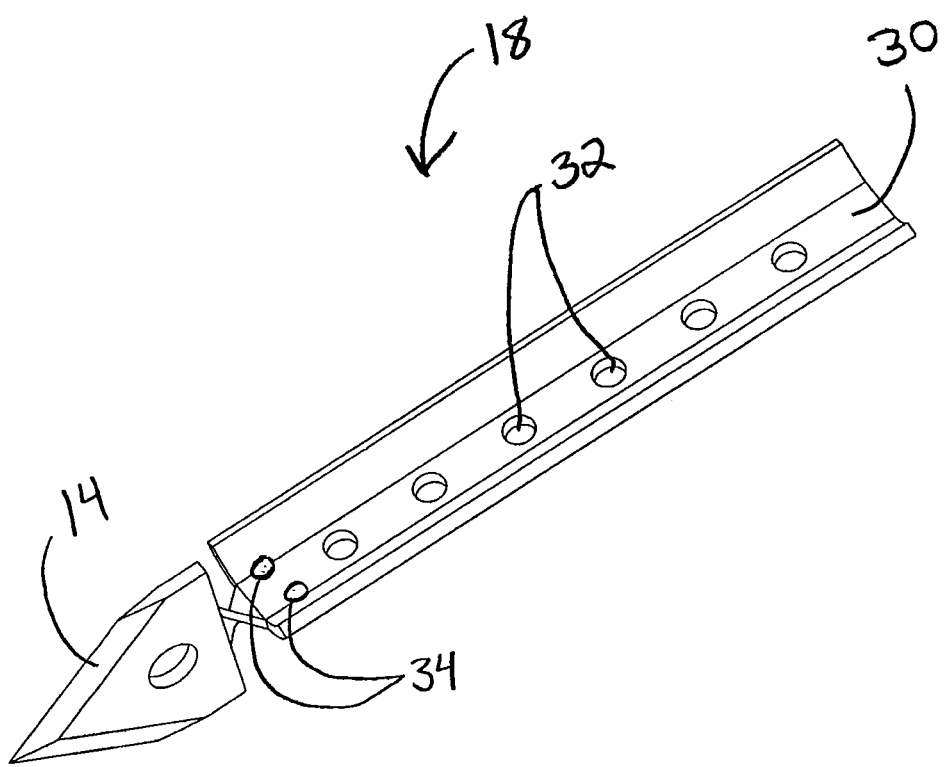
FIG. 11 depicts a perspective view of a needle component of the probe portion of FIG. 6.

In the present example, needle portion (10) comprises an outer cannula (12) having a tissue piercing tip (14) and a transverse tissue receiving aperture (16) located proximally from the tissue piercing tip (14). Tissue piercing tip (14) is configured to penetrate tissue without requiring a high amount of force, and without requiring an opening to be preformed in the tissue prior to insertion of tip (14). Suitable configurations for tissue piercing tip (14) will be apparent to those of ordinary skill in the art in view of the teachings herein. For instance, as shown in FIG. 11, tip (14) of the present example is part of a needle piece (18), which is formed of a stamped piece of metal. In particular, needle piece (18) is stamped to form tip (14) and wall (30), which will be described in greater detail below. A plurality of openings (32), including venting openings (34) are formed through wall. Various ways in which fluid may be communicated through openings (32, 34) will be described in greater detail below, with reference to FIGS. 61-65. Needle piece (18) is then twisted such that tip (14) and wall (30) are substantially perpendicular to one another. Needle piece (18) is then inserted into cannula (12), with tip (14) protruding through a slot formed in the distal end of cannula (12). A tissue stop (26) is provided immediately proximal to tip (14). Still other ways in which tip (14) may be formed, including alternative techniques, materials, and configurations, will be apparent to those of ordinary skill in the art in view of the teachings herein.

The interior of outer cannula (12) of the present example defines a cannula lumen (20) and a vacuum lumen (40), with a wall (30) separating the cannula lumen (20) from the vacuum lumen (40). A plurality of external openings (22) are formed in outer cannula (12), and are in fluid communication with vacuum lumen (40). Examples of openings that are similar to external openings (22) are disclosed in U.S. Pub. No. 2007/0032742, entitled "Biopsy Device with Vacuum Assisted Bleeding Control," published Feb. 8, 2007, the disclosure of which is incorporated by reference herein. Of course, as with other components described herein, external openings (22) are merely optional.

In some embodiments, wall (30) extends a substantial amount of the length of needle portion (10). In other embodiments, wall (30) proximally extends just past the region where the distal end of a cutter (50), which will be described below, terminates in needle portion (10). For instance, cannula lumen (20) may be sized and configured such that, with cutter (50) disposed therein, a gap exists between the exterior of cutter (50) and at least a portion of the interior of cannula (12). Such a gap may provide a vacuum lumen (40) along the length of cannula (12) proximal to the proximal end of wall (30). Still other ways in which a vacuum lumen (40) may be provided will be apparent to those of ordinary skill in the art in view of the teachings herein.

In the present example, a plurality of transverse openings (32, 34) are formed through wall (30) to provide fluid communication between cannula lumen (20) and vacuum lumen (40). As will be described in greater detail below, vacuum, saline, and/or pressurized air may be communicated from vacuum lumen (40) to cannula lumen (20) via transverse openings (32, 34).

B. Exemplary Cutter

A hollow cutter (50) is disposed within cannula lumen (20). The interior of cutter (50) defines a cutter lumen (52), such that fluid and tissue may be communicated through cutter (50) via cutter lumen (52). As will be described in greater detail below, cutter (50) is configured to rotate within cannula lumen (20) and translate axially within cannula lumen (20). In particular, cutter (50) is configured to sever a biopsy sample from tissue protruding through transverse aperture (16) of outer cannula (12). As will also be described in greater detail below, cutter (50) is further configured to permit severed tissue samples (4) to be communicated proximally through cutter lumen (52). Merely illustrative examples of such severing and proximal communication are described in U.S. Pat. No. 5,526,822, the disclosure of which is incorporated by reference herein, though any other suitable structures or techniques may be used for severing and/or communicating tissue samples (4) within a biopsy system (2).

Cutter (50) may be subject to various treatments or configurations in order to facilitate proximal communication of tissue samples (4) through cutter lumen (52). For instance, the surface finish inside of cutter (50), defining cutter lumen (52), may be subject to shot peening (e.g., with glass beads, sodium bicarbonate, etc.) to reduce adhesion between tissue and cutter (50). In addition, or in the alternative, the interior of cutter (50), defining cutter lumen (52), may be subject to acid etching and/or plasma etching to reduce adhesion between tissue and cutter (50). In addition, or in the alternative, a hydrolubricous material or other non-stick coating may be applied to the interior of cutter (50), defining cutter lumen (52), to reduce friction between tissue and cutter (50). In addition, or in the alternative, the interior of cutter (50), defining cutter lumen (52), may be subject to a rifling surface cut. Other suitable treatments for the interior of cutter (50) will be apparent to those of ordinary skill in the art in view of the teachings herein. Alternatively, the interior of cutter (50) may be subject to no treatment at all in some embodiments.

In an alternate embodiment of cutter (50), a distal portion of cutter (50) has an inner diameter and outer diameter that are less than the inner diameter and outer diameter of a proximal portion of cutter (50). For instance, the distal-most inch of cutter (50) may provide a neck down region (not shown), which transitions into a region having a greater diameter along the remaining, proximal length of cutter (50). Such a neck down configuration may reduce tissue compression as a tissue sample (4) moves proximally through cutter lumen (52). The distal end of outer cannula (12) may also have a complimentary neck down region that is either the same length as, shorter than, or longer than a neck down region of cutter (50). Other suitable lengths of a neck down region in cutter (50) and/or outer cannula (12) will be apparent to those of ordinary skill in the art in view of the teachings herein.

In another alternative embodiment of cutter (50), a plurality of raised surfaces are provided, extending inwardly within the interior of cutter (50), running the length of cutter (50). Such raised surfaces may be configured to reduce tissue surface contact with the interior of cutter (50).

In yet another alternative embodiment of cutter (50), an inner sleeve (not shown) may be provided within the distal end interior of cutter (50). For instance, such an inner sleeve may have a length of approximately 0.15 inches or any other suitable length. The distal end of cutter (50) may be chamfered after such an inner sleeve is inserted, such that chamfered cutter (50) end and the chamfered sleeve end collectively provide a sharp edge for severing tissue. As a severed tissue sample (4) travels proximally through cutter lumen (52), it will encounter a greater inner diameter of cutter lumen (52) as soon as the tissue sample (4) passes the proximal end of the inner sleeve. This increase in effective diameter may reduce compression of the tissue sample (4), thereby improving transport reliability of the tissue sample (4). Still other suitable variations of cutter (50) will be apparent to those of ordinary skill in the art in view of the teachings herein.

C. Exemplary Needle Hub

Figure 12:
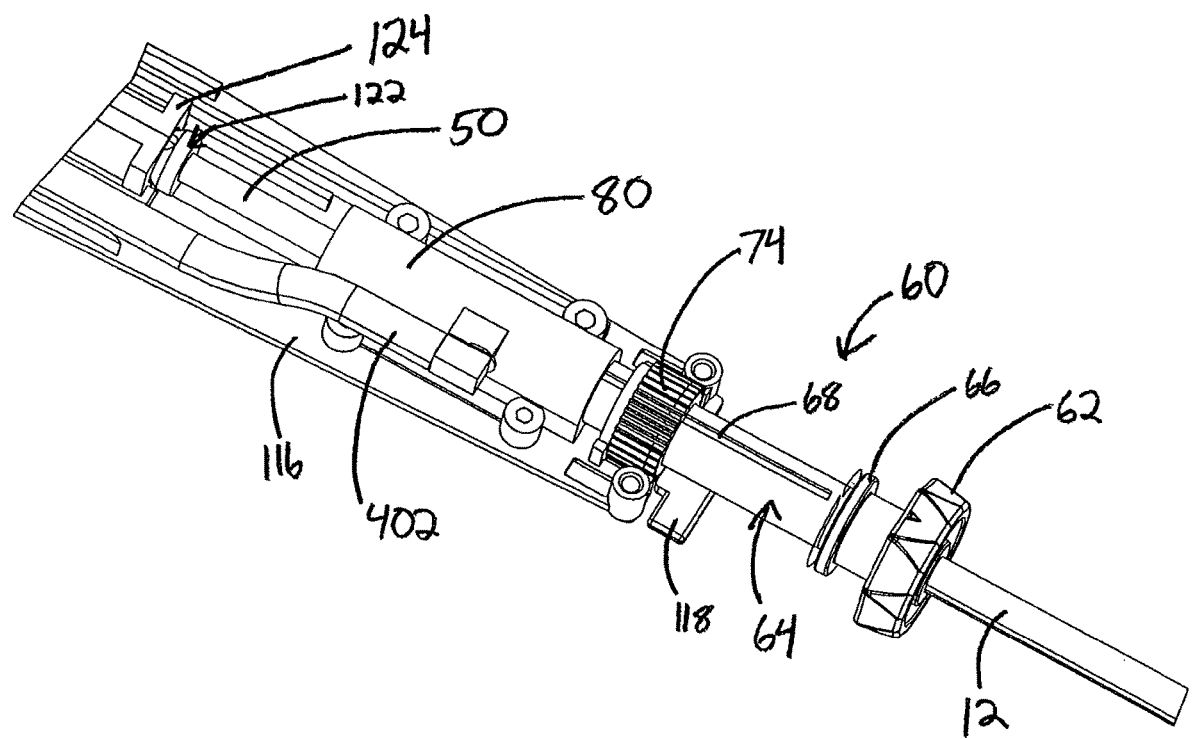
FIG. 12 depicts a partial perspective view of the probe portion of FIG. 6, showing a needle hub assembly.
Figure 13:
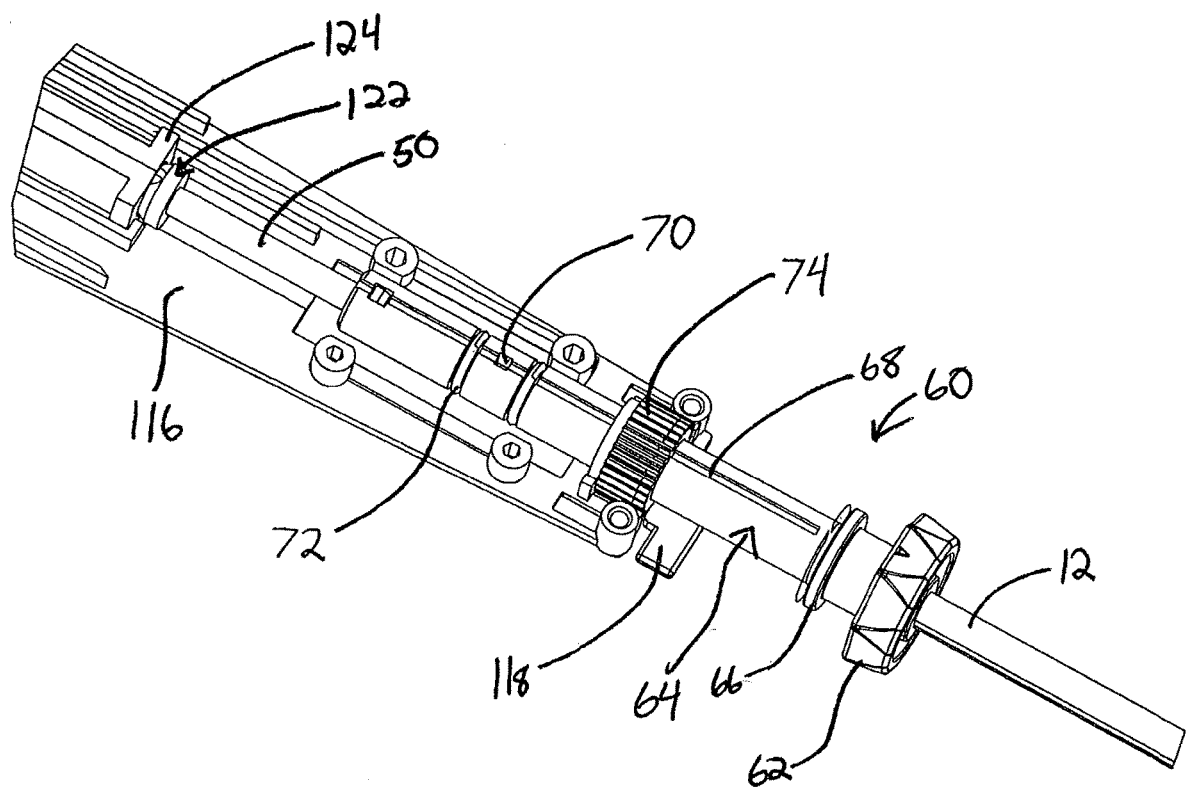
FIG. 13 depicts a partial perspective view of the probe portion of FIG. 6, showing a needle hub assembly with a needle manifold removed.

As shown in FIGS. 12-13, a needle hub (60) is secured to outer cannula (12), and comprises a thumbwheel (62) and a sleeve portion (64) extending proximally from thumbwheel (62). Needle hub (60) of the present example is overmolded about a proximal portion of outer cannula (12), though needle hub (60) may be formed and/or secured relative to outer cannula (12) using any other suitable techniques (e.g., set screws, adhesives, etc.). Furthermore, while needle hub (60) of the present example is formed of a plastic material, any other suitable material or combination of materials may be used.

Sleeve portion (64) of the present example comprises an annular projection (66), a longitudinal slot (68), and a transverse opening (70), which is formed near the proximal end of sleeve portion (64). One or more additional transverse openings (70) (e.g., diametrically opposed transverse openings (70)) may also be provided in sleeve portion (64). A pair of o-rings (72) are positioned such that one o-ring (72) is proximal to transverse opening (70) and another o-ring (72) is distal to transverse opening (70). As will be described in greater detail below, transverse opening (70) is in fluid communication with the interior defined by needle hub (60), which is also in fluid communication with vacuum lumen (40) of outer cannula (12). Other suitable configurations for sleeve portion (64) will be apparent to those of ordinary skill in the art in view of the teachings herein.

Thumbwheel (62) is operable to rotate outer cannula (12) about its longitudinal axis, relative to cover member (114) and base member (116). For instance, thumbwheel (62) may be used to orient aperture (16) to a number of desired orientations about the longitudinal axis defined by outer cannula (12). Such multiple orientations may be desirable, by way of example only, to obtain a plurality of tissue samples (4) from a biopsy site, without requiring the needle portion (10) to be removed from the patient during the acquisition of such a plurality of tissue samples (4). An illustrative example of such rotation and acquisition of multiple tissue samples (4) is disclosed in U.S. Pat. No. 5,526,822, the disclosure of which is incorporated by reference herein. Other ways in which multiple tissue samples (4) may be obtained at various locations will be apparent to those of ordinary skill in the art in view of the teachings herein. For instance, rotation of outer cannula (12) may be motorized or automated, such as using any of the components described in greater detail below, or using any other suitable components or techniques. As another non-exhaustive example, an entire biopsy device (101) may be rotated during acquisition of tissue samples (4), without necessarily removing biopsy device (101) from the patient during such rotation and tissue sample (4) acquisition, to obtain tissue samples (4) from various orientations about the longitudinal axis defined by outer cannula (12).

It will also be appreciated that other structures may be used to perform manual rotation of outer cannula (12). In particular, and as shown in FIG. 12-13, an exposed gear (74) may be engaged with outer cannula (12). In this example, gear (74) is slid onto the proximal end of sleeve portion (64). A radially inwardly extending projection (not shown) of gear (74) is configured to mate with slot (68) of sleeve portion (64), such that gear (74) rotates unitarily with sleeve portion (64) while being movable longitudinally along sleeve portion (64). With sleeve portion (64) being unitarily engaged with outer cannula (12), rotation of gear (74) will further cause rotation of cannula (12) for reorienting aperture (16). Gear (74) is further configured to engage with a complimentary exposed gear (206) of holster (202), as will be described in greater detail below. In particular, gear (74) is configured to mesh with gear (206) such that gear (206) can impart rotation to gear (74), thereby rotating outer cannula (12). Some exemplary structures and techniques for selectively causing gear (206) to rotate will be discussed in greater detail below, while others will be apparent to those of ordinary skill in the art in view of the teachings herein.

It will also be appreciated in view of the teachings herein that the orientation of aperture (16) may be indicated on a graphical user interface. For instance, one or more sensors may be operable to detect the orientation of aperture (16), and communicate indicative data to a processor. The processor may be in communication with a display (e.g., display screen (702), described below, etc.) to provide visual indication of aperture (16) orientation. Other ways in which the orientation of aperture (16) may be indicated to a user will be apparent to those of ordinary skill in the art in view of the teachings herein. Alternatively, orientation of aperture (16) may be not indicated to a user.

D. Exemplary Needle Manifold

As shown in FIG. 12, a needle manifold (80) is provided about sleeve portion (64). Needle manifold (80) is fixed relative to base member (116) in this example. Needle manifold (80) is in fluid communication with tube (402), such that tube (402) may communicate saline, a vacuum, atmospheric air, and/or pressurized air, etc., to needle manifold (80), as will be described in greater detail below. Needle manifold (80) is further in fluid communication with the interior of sleeve portion (64), via transverse opening (70). O-rings (64) are configured to maintain a fluid seal between needle manifold (80) and sleeve portion (64), even as sleeve portion (64) translates longitudinally relative to needle manifold (80), such as during firing of needle (10) as will be described in greater detail below; and even during rotation of sleeve portion (64) about its longitudinal axis. A seal (not shown) is also provided at the proximal end of sleeve portion (64), at the interface between sleeve portion (64) and cutter (50). Needle manifold (80), sleeve portion (64), and outer cannula (12) are thus configured and arranged such that saline, a vacuum, atmospheric air, and/or pressurized air, etc. that is communicated via tube (402) to needle manifold (80) will be communicated to vacuum lumen (40) via transverse opening (70). Of course, any other suitable structures or arrangements may be used to communicate saline, a vacuum, atmospheric air, and/or pressurized air, etc. from tube (402) to vacuum lumen (40).

E. Exemplary Cutter Rotation and Translation Mechanism

Figure 14:
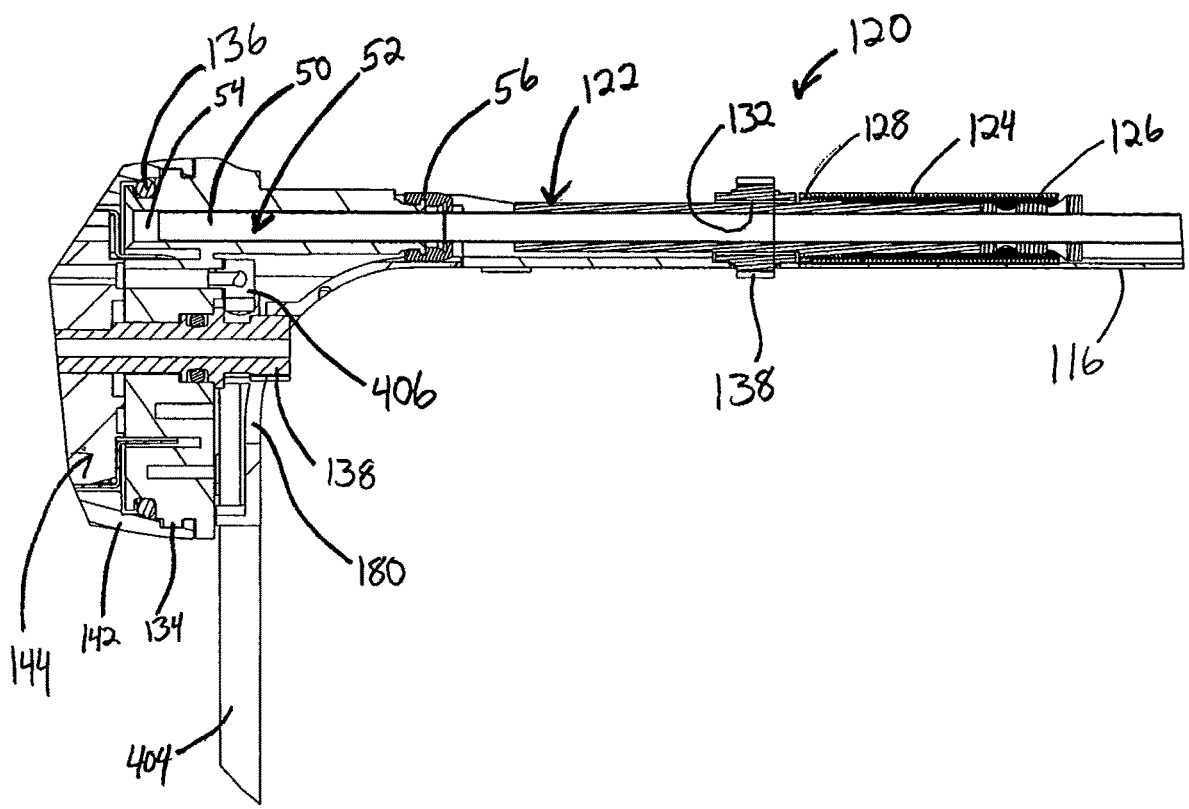
FIG. 14 depicts a partial, cross-sectional view of a cutter rotation and translation mechanism of the probe portion of FIG. 6, taken along a longitudinal plane.
Figure 15:
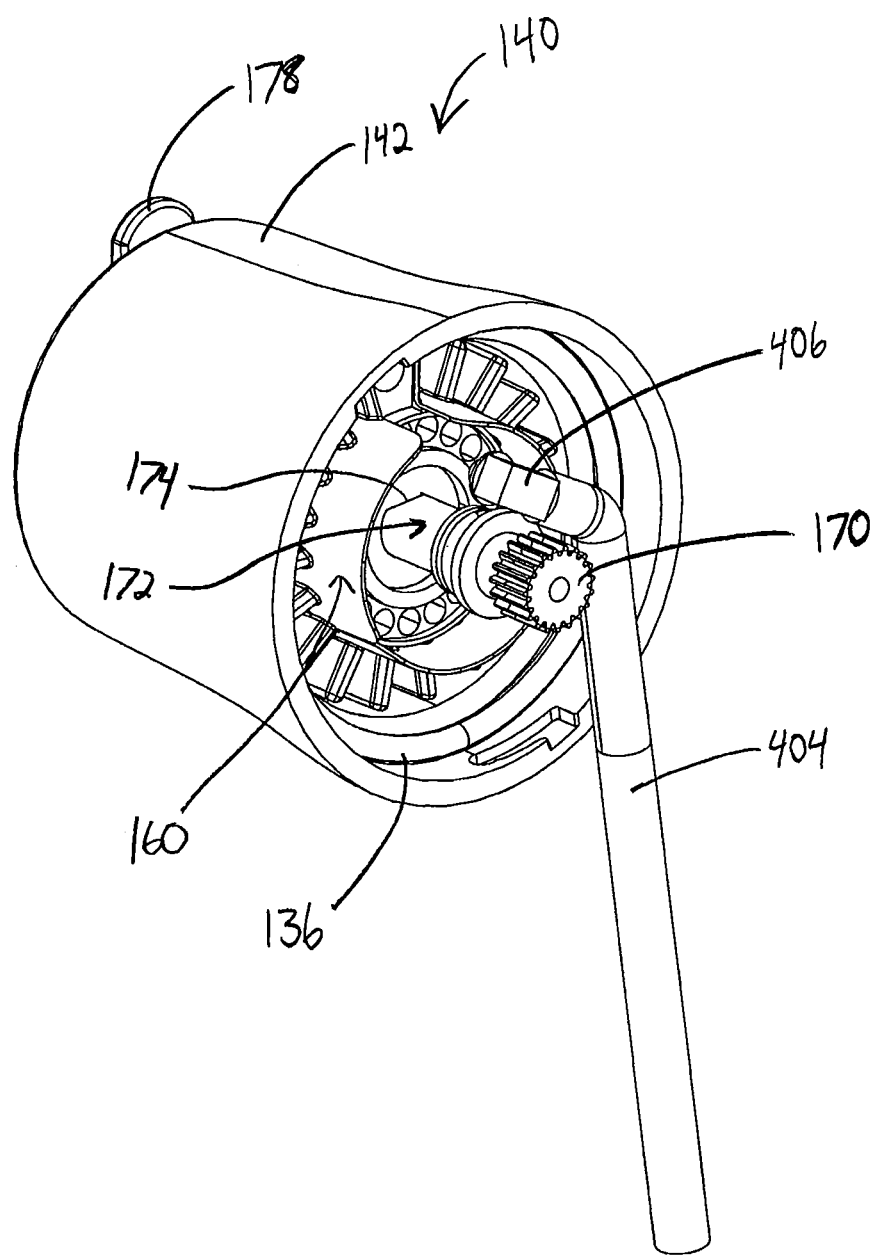
FIG. 15 depicts a front perspective view of an exemplary tissue sample holder.
Figure 16:
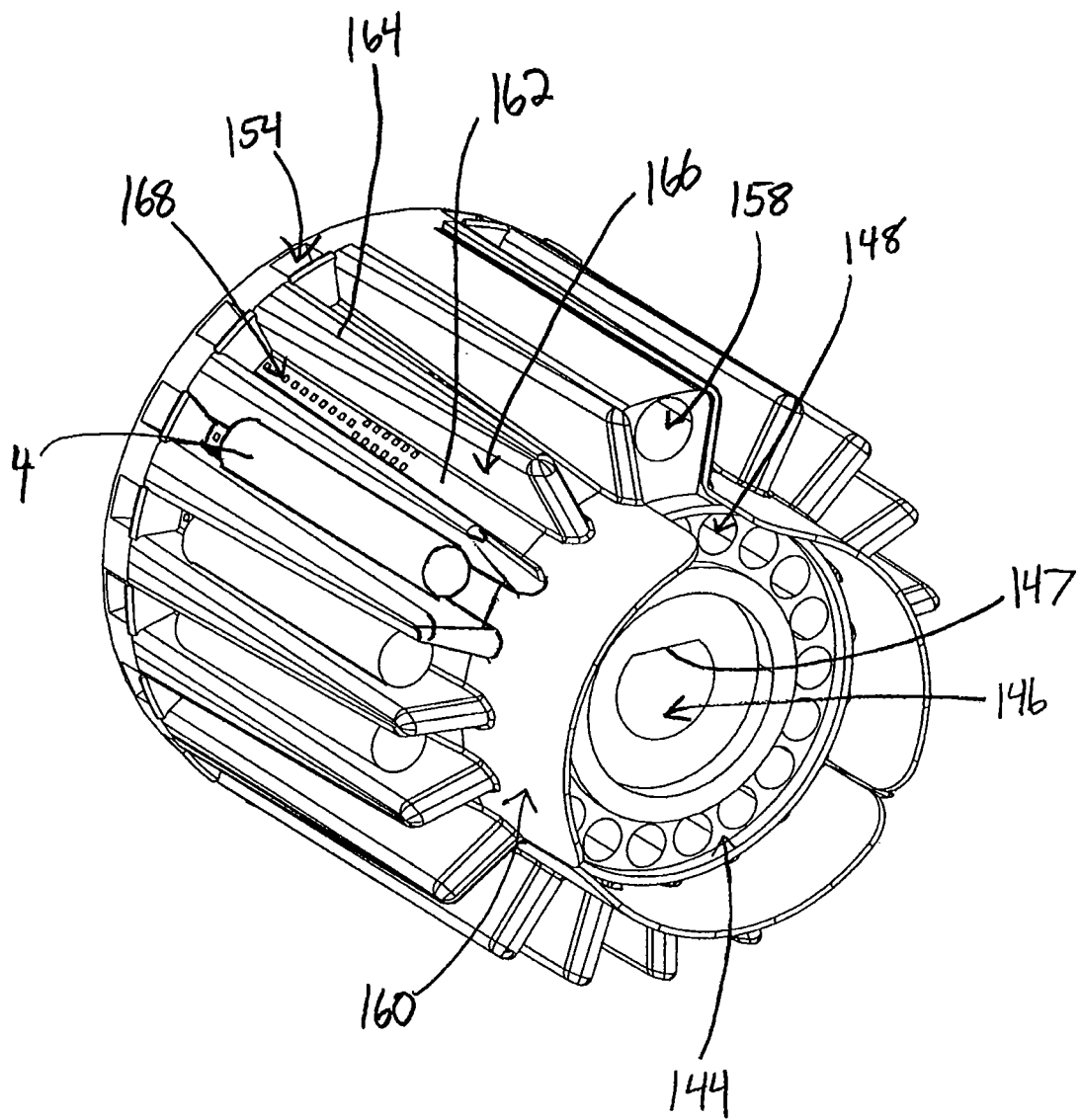
FIG. 16 depicts the tissue sample holder of FIG. 15, with a cup and other components removed.
Figure 17:
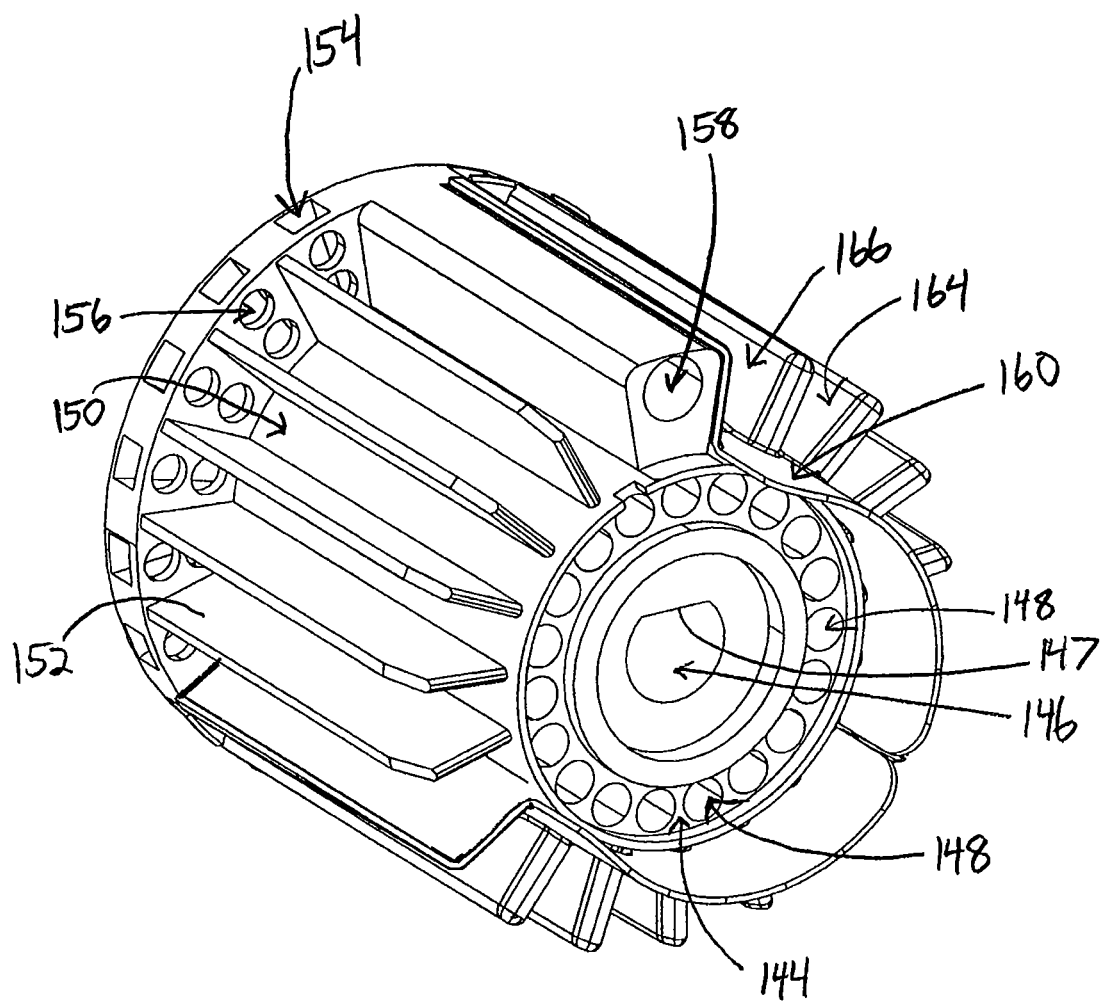
FIG. 17 depicts the tissue sample holder of FIG. 15, with a tissue sample tray removed.
Figure 18:
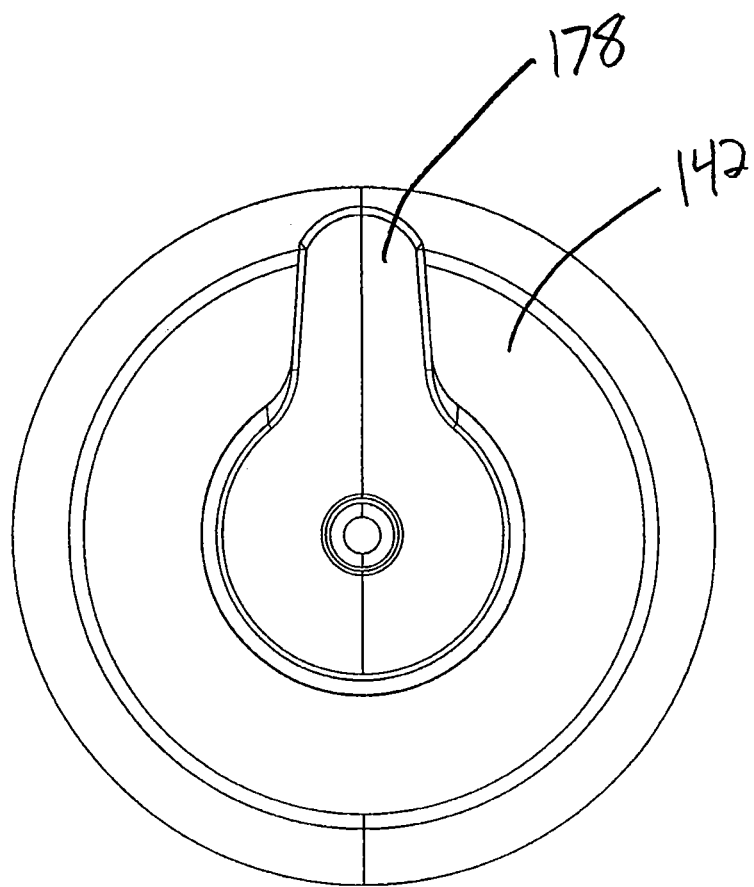
FIG. 18 depicts a rear view of the tissue sample holder of FIG. 15.
Figure 19:
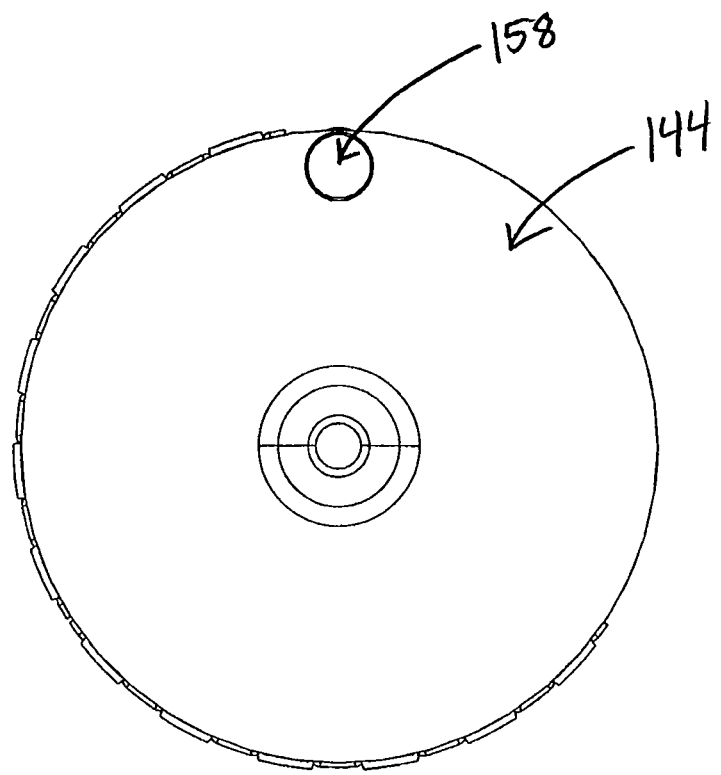
FIG. 19 depicts a rear view of the tissue sample holder of FIG. 15, with a cup and other components removed.

In the present example, and as shown in FIG. 14, body portion (112) of probe (102) comprises a cutter rotation and translation mechanism (120), which is operable to rotate and translate cutter (50) within outer cannula (12). Cutter rotation and translation mechanism (120) comprises a sleeve (122) unitarily secured to cutter (50), a nut member (124), and a gear (138). In the present example, sleeve (122) is formed of plastic overmolded about cutter (50), though any other suitable materials may be used, and sleeve (122) may be secured relative to cutter (50) using any other suitable structures or techniques (e.g., set screws, etc.). Nut member (124) is secured relative to base member (116), and has internal threads (126). A portion of sleeve (122) has external threads (128) that are configured to engage with threads (126) of nut member (124). Threads (126, 128) are configured such that, as sleeve (122) rotates relative to nut member (124), sleeve (122) will longitudinally translate relative to nut member (124), depending on the direction of such relative rotation. By way of example only, threads (126, 128) may be configured to have a pitch that provides approximately 40-50 threads per inch. Such a thread pitch may provide a ratio of cutter (50) rotation to cutter (50) translation that is ideal for severing tissue. Alternatively, any other thread pitch may be used. With sleeve (122) being unitarily secured to cutter (50) in the present example, longitudinal translation of sleeve (122) relative to nut member (124) will result in the same translation of cutter (50).

Another portion of sleeve (122) has a plurality of external flats (130), which are configured to engage with a complimentary plurality of internal flats (132) of gear (138). Gear (138) is positioned coaxially about sleeve (122) and cutter (50). Flats (130, 132) are configured such that rotation of gear (138) causes rotation of sleeve (122). With sleeve (122) being unitarily secured to cutter (50) in the present example, rotation of gear (138) and sleeve (122) will result in the same rotation of cutter (50). Flats (130, 132) are further configured such that sleeve (122) may translate longitudinally relative to gear (138) (e.g., the fit between sleeve (122) and gear (138) is not so tight as to prevent such translation). It will therefore be appreciated that, as gear (138) rotates, given the relative configurations of threads (126, 128) and flats (130, 132), such rotation of gear (138) will simultaneously result in rotation and longitudinal translation of sleeve (122), which will in turn result in simultaneous rotation and longitudinal translation of cutter (50).

In the present example, gear (138) is partially exposed through base member (116), and is configured to mate with a complimentary exposed gear (208) of holster (202), as will be described in greater detail below. In particular, gear (138) is configured to mesh with gear (208) such that gear (208) can impart rotation to gear (138), thereby activating cutter rotation and translation mechanism (120). As will be described in greater detail below, gear (208) is in communication with a motor (272) that is within holster (202). In the present example, gears (138, 208) and threads (126, 128) are configured such that each revolution of motor (272) results in approximately 0.00012 inches of translation of cutter (50). Of course, any of these components may have other configurations that result in any other suitable ratio of cutter (50) translation to motor (272) rotation.

It will be appreciated in view of the teachings herein that cutter rotation and translation mechanism (120) described above is merely exemplary, and that translation and/or rotation of cutter (50) may alternatively be provided in various other ways. For instance, biopsy probe (102) may include a motor (not shown) or other device, such that biopsy probe (102) lacks exposed gear (138). Alternatively, any suitable structure other than exposed gear (138) (e.g., a rack, etc.) may be used to receive communication of motion or energy from some other component, in order to rotate and/or translate cutter (15). Furthermore, cutter rotation and translation mechanism (120) may be configured such that more than one exposed gear (138) is present (e.g., one gear (138) for receiving translation motion, and another gear (138) for receiving rotation motion, etc.). In other merely illustrative alternatives, translation and/or rotation of cutter (50) may be performed at least in part by pneumatic actuators (not shown), pneumatic motors (not shown), or a variety of other components. Furthermore, it will be appreciated that pneumatic components may be combined with other mechanical components and/or electro-mechanical components in order to translate and/or rotate cutter (50).

Base member (116) further comprises a cutter passage (54), through which the proximal end of cutter (50) is disposed. A seal (56) is provided at the distal interface of cutter (50) and cutter passage (54), to prevent escape of a vacuum or fluid between the outer surface of cutter (50) and the inner surface of the distal end of cutter passage (54). Cutter passage (54) is sized such that, as cutter (50) translates during use of biopsy device (100), the distal end of cutter (50) remains within cutter passage (54). Of course, any other suitable structures or configurations may be used.

F. Exemplary "Sharps Reduction" Variation

In the present example, needle portion (10) and cutter (50) are configured to be removable from biopsy probe (102), such as after a session of use of biopsy device (100). In particular, base member (116) of body portion (112) of biopsy probe (102) comprises a release tab (118), which is resiliently movable relative to base member (116) via an arm (119). Release tab (118) is configured to restrict axial movement of needle portion (10) by restricting axial movement of gear (74), which is engaged with sleeve portion (64) of hub (60) as noted above, when release tab (118) is in a default position. Of course, the engagement between and configurations of gear (74) and sleeve portion (64) will permit some degree of axial movement of needle portion (10), such as for firing of needle portion (10), even while release tab (118) is in a default position. However, when release tab (118) is sufficiently depressed, such as by a user, release tab will provide clearance for gear (74) to be moved distally of base member (116). In other words, with release tab (118) sufficiently depressed, the entirety of needle portion (10), including the entirety of needle hub (60) and gear (74), may be axially pulled distally from body portion (112) of biopsy probe (102); such that the entirety of needle portion (10), including the entirety of needle hub (60) and gear (74), may be completely separated from body portion (112).

It will be appreciated in view of the disclosure herein that, with the entirety of needle portion (10), including the entirety of needle hub (60) and gear (74), completely separated from body portion (112), cutter (50) will still be extending from body portion (112). To remove cutter (50) from body portion, a user may simply "unscrew" cutter (50) from body portion (112). In particular, the user may grip a portion of needle (50) protruding from body portion (112) and rotate needle (50) relative to body portion (112) while pulling distally on cutter (50). Such rotation and pulling of cutter (50) may cause interaction of threads (126, 128) that ultimately results in threads (128) passing completely distally past threads (126). With threads (128) passing completely distally past threads (126), no other components of body portion (112) will substantially constrain cutter (50) in the axial direction, such that cutter (50) may be pulled distally completely from body portion (112) without further rotation. In other words, after sufficient rotation of cutter (50) relative to body portion (112), cutter (50) may be completely separated from body portion (112). It will be appreciated in view of the teachings herein that sleeve (122) and needle manifold (80) may be configured such that sleeve (122) may be axially passed completely through needle manifold (80). Gear (138) may essentially remain in its place as sleeve (122) and the rest of cutter (50) is pulled axially relative thereto. Other suitable relationships between components to provide, permit, or facilitate removability of needle portion (10) and cutter (50) from body portion (112) will be apparent to those of ordinary skill in the art in view of the teachings herein.

While a release tab (118) and other components have been described as providing and/or permitting complete removability of needle portion (10) and cutter (50) from body portion (112), it will be appreciated in view of the teachings herein that such removability may be provided using a variety of other structures and techniques. For instance, in some embodiments, tab (118) or some other feature is configured to break away from base member (116) when engaged with sufficient force, permitting removal of the entirety of needle portion (10), including the entirety of needle hub (60) and gear (74). In yet another alternate embodiment, probe (102) is configured such that, when needle portion (10) and needle hub (60) are manually angulated relative to rest of body portion (112), a retention feature located in base member (116) is disengaged, allowing the entirety of needle portion (10), including the entirety of needle hub (60) and gear (74), to be removed axially from body portion (112). Still other components, features, and techniques for providing, permitting, or facilitating removability of needle portion (10) and cutter (50) from body portion (112) will be apparent to those of ordinary skill in the art in view of the teachings herein.

It will also be appreciated that such removability may reduce the amount of "sharps" provided by biopsy device (100). In particular, to the extent that sharp device components that have been exposed to bodily fluids need to be disposed of in a manner different from disposal of other waste (e.g., placed in a "sharps bin" as opposed to a regular trash bin), the complete removability of needle portion (10) and cutter (50) from body portion (112) may permit the needle portion (10) and cutter (50) to be handled in accordance with "sharps" waste disposal procedure without requiring the remainder of body portion (112) to be subject to the same waste disposal. In other words, and by way of example only, after a use of biopsy device (100), the needle portion (10) and cutter (50) may be removed from body portion (112) and placed in a "sharps bin," while the remainder of body portion (112) may be placed in a regular trash bin.

G. Exemplary Tissue Sample Holder Manifold

As shown in FIGS. 15-19, a tissue sample holder (140) is provided at the end of body portion (112) of probe (102). Tissue sample holder (140) comprises a cup (142), a manifold (144), and a plurality of trays (160). Manifold (144) includes a central recess (146), a plurality of longitudinal passages (148), a plurality of chambers (150) defined by radially extending walls (152), and plurality of radial passages (154). Each longitudinal passage (148) is substantially in fluid isolation relative to every other longitudinal passage (148). However, each radial passage (154) is substantially in fluid communication with every other radial passage (154) via an annular passage (not shown) located within the rear of manifold (144). Alternatively, each radial passage (154) may be substantially in fluid isolation relative to every other radial passage (154). In the present example, each longitudinal passage (148) is in fluid communication with a corresponding one of each radial passage (154). In particular, each longitudinal passage (148) terminates proximally in a corresponding radial passage (154).

In addition, each radial passage (154) is in fluid communication with a corresponding one of each chamber (150), via a respective pair of openings (156). Accordingly, it will be appreciated that each longitudinal passage (148) is in fluid communication with a corresponding chamber (150), via a corresponding radial passage (154) and pair of openings (156). In particular, the radial position of each longitudinal passage (148) relative to central recess (146) corresponds with the radial position of the associated radial passage (154), pair of openings (156), and chamber (150). Of course, any other suitable structures or configurations for manifold (144) may be used.

In some variations, a screen, mesh, or other component is provided on or in manifold (144), or elsewhere within tissue sample holder (140), to prevent passage of tissue into or through certain openings or gaps. In other variations, such components are omitted.

H. Exemplary Tissue Sample Trays

Trays (160) of the present example are configured to be placed on manifold (144), and to receive tissue samples (4) as will be described in greater detail below. Each tray (160) may be rigid, and may be preformed to have a generally arcuate configuration. Alternatively, trays (160) may be formed of a flexible material, such that trays (160) may be bent to conform to the curvature of manifold (144). Alternatively, trays (160) may comprise one or more joints, such that portions of trays (160) may bend or flex at such joints. Still other suitable configurations may be used.

Each tray (160) of the present example has a base portion (162) and a plurality of hollow wall portions (164). Hollow wall portions (164) define chambers (166). By way of example only, each chamber (166) may be configured to receive a single tissue sample (4) captured by cutter (50). Alternatively, chambers (166) may be configured such that each chamber (166) may hold more than one tissue sample (4). Manifold (144) and chambers (166) of the present example are further configured such that blood, saline, and/or other fluids may pass through a chamber (166) and exit through tube (404), even if a tissue sample (4) is within such a chamber (166). In other words, chamber (166) will permit fluids to pass around a tissue sample (4).

As shown, the underside of each hollow wall portion (164) is configured to receive a wall (152) of manifold (144). Wall portions (164) and walls (152) are configured such that a gap is provided between each base portion (162) and manifold (144) when trays (160) are placed on manifold (144). As is also shown, each hollow wall portion (164) has a generally tapered configuration, though any other suitable configuration may be used. In addition, trays (160) have a plurality of openings (168) that are formed, in sets, through the base portion (162) within each chamber (164). Accordingly, each chamber (166) of trays (160) is in fluid communication with an associated chamber (150) of manifold (144) via openings (168). Each longitudinal passage (148) of manifold (144) is therefore in fluid communication with a corresponding chamber (166) of trays (160). It will therefore be appreciated that, when tube (404) is placed in fluid communication with a given longitudinal passage (148), tube (404) will be in fluid communication with the chamber (166) that is associated with that longitudinal passage (148).

In the present example, manifold (144) and trays (160) provide eighteen chambers (150, 166). Alternatively, any other number of chambers (150, 166) (i.e., more or less than eighteen) may be provided. For instance, in one variation, manifold (144) provides three chambers (150), and three trays (160) are used that each have only one chamber (166). In yet another variation, a single tray (160) is used. For instance, a single tray (160) may provide a single large chamber (166) or any suitable number of chambers (166). Other suitable numbers of chambers (150, 166) and ways in which such chambers (150, 166) may be provided will be apparent to those of ordinary skill in the art in view of the teachings herein. Furthermore, manifold (144) and trays (160) may have any suitable shape.

Each tray (160) may further comprise one or more types of markings or other indicia to distinguish one chamber (166) from another chamber (166). For instance, a number or other distinguishing marking may be provided on or near each chamber (166), such as in relief form, in recessed form, or otherwise. In another embodiment, a radiopaque marker is provided on or near each chamber (166). For instance, an entire tray (160) that is carrying one or more tissue samples (4) may be placed under X-ray for evaluation, and the radiopaque marker associated with each chamber (166) (and hence, associated with each tissue sample (4)), may be visible in the image obtained using X-ray. In other words, tissue samples (4) need not necessarily be removed from trays (160) in order to take an X-ray or radiograph image of tissue samples (4). Furthermore, trays (160) may be dropped directly into formalin or any other liquid with tissue samples (4) still on trays (160). In addition, trays (160) may be placed in a sleeve or container, etc., individually or in groups, to protect tissue samples (4) and/or to ensure that tissue samples (4) stay in trays (160) or for other purposes. Such a sleeve or container may be flexible, rigid, or have other properties. By way of example only, a sleeve or other container may be flat, and may be configured to flatten out a flexible tray (160) that is inserted therein. Other structures and techniques that may be used with trays (160), such as after tissue samples (4) are communicated to trays (160) will be apparent to those of ordinary skill in the art in view of the teachings herein.

Cup (142) is configured to engage bayonets (134) of base member (116), such that cup (142) may be removed from or secured to base member (116) upon sufficient rotation of cup (142) relative to base member (116). In addition, an o-ring (136) is provided about base member (116) to provide a seal between base member (116) and cup (142). Of course, any other suitable structures may be used to provide engagement of cup (142) with base member (116) and/or to provide a seal between base member (116) and cup (142). Cup (142) is also formed of a transparent material in the present example, enabling the user to visually inspect tissue samples (4) in tissue sample holder (140) while tissue sample holder (140) is still coupled with base member (116). For instance, a user may inspect tissue samples (4) for color, size, and density (e.g., to the extent that chamber (166) is full of saline, etc.).

It will also be appreciated in view of the teachings herein that the removability of cup (142) and trays (160) may permit a user to harvest a relatively large number of tissues samples in a relatively short period of time. Furthermore, the removability of cup (142) and trays (160) may permit a user to remove unsatisfactory tissue samples (4) from tissue sample holder (140) (e.g., using tweezers, etc.) and then re-couple trays (160) and cup (142) for further sampling. Other ways in which the removability and other properties of tissue sample holder (140) of the present example may be utilized will be apparent to those of ordinary skill in the art in view of the teachings herein.

I. Exemplary Rotation and Alignment of Manifold

Manifold (144) of the present example is configured to rotate relative to base member (116), as will be described in greater detail below. Manifold (144) of the present example is further configured such that each longitudinal passage (148) may be selectively aligned with a port (406) that is in fluid communication with tube (404). Such alignment of a longitudinal passage (148) and port (406) will place the aligned longitudinal passage (148) in fluid communication with tube (404), such that induction of a vacuum within tube (404) will effect induction of a vacuum within longitudinal passage (148), as well as within the chamber (166) associated with that longitudinal passage (148). In addition, manifold (144) and trays (160) of the present example are configured such that each chamber (166) may be selectively placed in fluid communication with cutter lumen (52). It will therefore be appreciated that a vacuum in tube (404) may induce a vacuum in cutter lumen (52), with the vacuum being communicated via port (406), an associated longitudinal passage (148), an associated radial passage (154), an associated pair of openings (156), an associated chamber (150), an associated set of openings (168), and an associated chamber (166). Of course, there are a variety of other ways in which a vacuum may be induced within a cutter lumen (52), and any other suitable structures or techniques may be used. Furthermore, pressurized air, a liquid (e.g., saline), or any other fluid may be communicated in either direction through the above-mentioned components in lieu of or in addition to a vacuum being induced therein.

A gear (170) is engaged with manifold (144) of the present example. In particular, gear (170) has a shaft (172) that is inserted within central recess (146) of manifold (144). The shaft (172) has a flat (174) that is configured to engage a complimentary flat (147) of central recess (146). Engagement of flats (174, 147) is such that gear (170), shaft (172), and manifold (144) rotate unitarily. Alternatively, gear (170) and manifold (144) may have any other suitable configurations or relationships. Nevertheless, gear (170) of the present example may be used to rotate manifold (144), which will in turn permit selective alignment of longitudinal passages (148) with port (406), in addition to contemporaneously permitting selective alignment of chambers (166) with cutter lumen (52). In particular, and as will be described in greater detail below, gear (170) is configured to mesh with a complimentary gear (210) of holster (202), such that gear (210) may be used to impart rotation to gear (170). Such rotation may be used to selectively (e.g., consecutively) align chambers (166) with cutter lumen (52), to successively collect a discrete tissue sample (4) in each chamber (166) during use of biopsy device (100). Furthermore, such collection of tissue samples (4) may be performed without having to withdraw and re-insert needle portion (10) relative to patient during such a process.

J. Exemplary "Parking Pawl"

Figure 20:
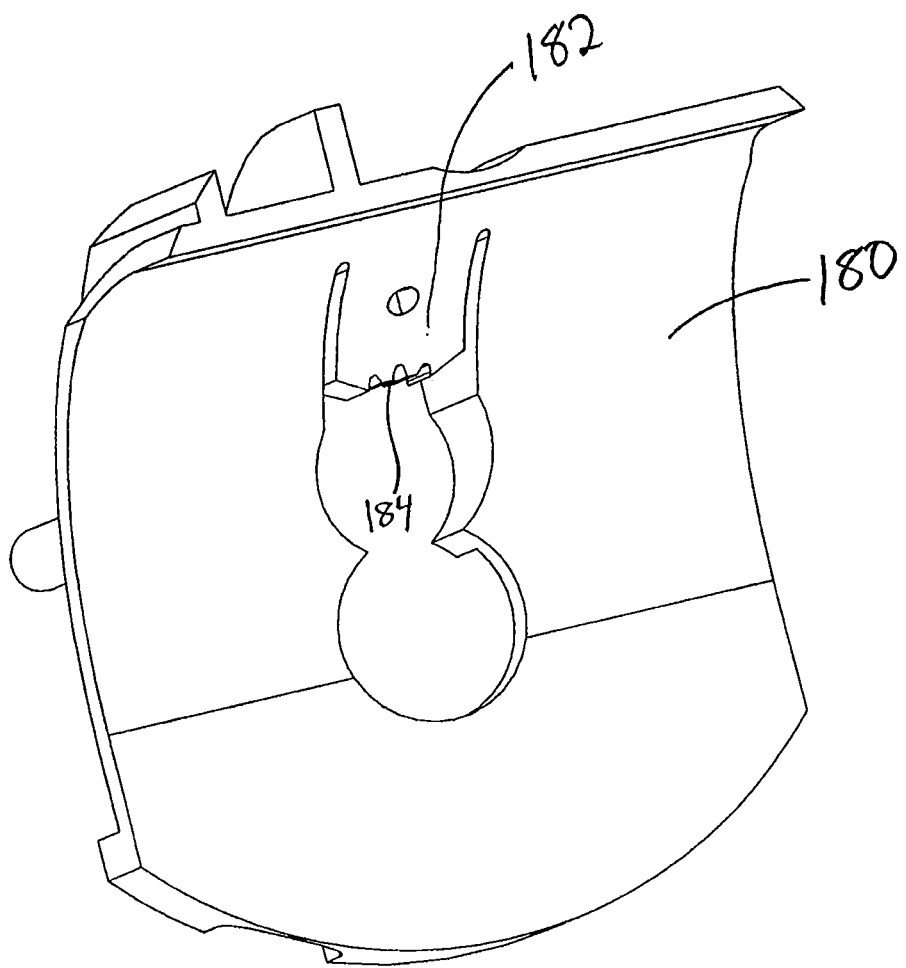
FIG. 20 depicts a perspective view of an engagement member.

Body portion (112) of the present example further comprises an engagement member (180), which is secured to base member (116). As shown in FIG. 20, engagement member (180) comprises a pawl portion (182) having teeth (184). Pawl portion (182) is resiliently urged for teeth (184) to engage with gear (170). In particular, engagement of teeth (184) of pawl portion (182) with gear (170) prevents rotation of gear (170) (and hence, prevents rotation of manifold (144)). Accordingly, pawl portion (182) is configured to prevent rotation of manifold (144) when pawl portion (182) is in a default position. In the present example, pawl portion (182) is in the default position when biopsy probe (102) is not coupled with a holster (202). However, when biopsy probe (102) is coupled with a holster (202), a boss (212) on holster (202) is configured to engage pawl portion (182). In particular, boss (212) on holster (202) is configured to disengage pawl portion (182) from gear (170) when biopsy probe (102) is coupled with a holster (202), such that pawl portion (182) will no longer prevent rotation of gear (170) or manifold (144) when biopsy probe (102) is coupled with a holster (202). When biopsy probe (102) is removed from holster (202), the resilience of engagement member (180)

urges pawl portion (182) back to the default position, such that pawl portion (182) will again prevent rotation of gear (170) and manifold (144).

When biopsy probe (102) is packaged for shipment from a manufacturing facility, or in other situations, tissue sample holder (140) may be configured such that a predetermined chamber (166) is aligned with cutter lumen (52). With pawl portion (182) maintaining such alignment to the time when biopsy probe (102) is coupled with a holster (202) for a first use, software or control logic that is used to control biopsy device (100) may "safely assume" that the predetermined chamber (166) is aligned with cutter lumen (52), and may control biopsy device (100) accordingly. Furthermore, if biopsy probe (102) is removed from holster (202) during a tissue sample (4) acquisition procedure, software or control logic that is used to control biopsy device (100) may "remember" which chamber (166) was last aligned with cutter lumen (52), to the extent that software tracks which chamber (166) is being or has been used during a procedure. If biopsy probe (102) is recoupled with holster (202) to continue the procedure, the software or control logic may continue to control biopsy device (100) based on the chamber (166) that the software "remembered." Alternatively, a user may specify that a new biopsy probe (102) has been coupled with holster (202), which may result in the software or control logic again "assuming" that the predetermined chamber (166) is the one that is aligned with the cutter lumen (52).

While a pawl portion (182) has been described as a structure selectively preventing the rotation of gear (170) and manifold (144), it will be appreciated that any other alternative structures may be used for such purposes. By way of example only, a Geneva wheel mechanism (not shown) may be used as an alternative mechanism for rotating manifold (144) and maintaining the rotational position of manifold (144) between intentional rotations. For instance, gear (170) may be substituted with a Geneva driven wheel (not shown), while gear (210) may be substituted with a Geneva drive wheel (not shown). Other suitable alternatives for rotating manifold (144) and/or maintaining the rotational position of manifold (144) will be apparent to those of ordinary skill in the art in view of the teachings herein. In addition, it will be appreciated that a biopsy device (100) may lack a pawl portion (182) or other rotation prevention feature altogether, such that a manifold (144) may freely rotate when biopsy probe (102) is not coupled with a holster (202).

K. Exemplary Dedicated Passage

As shown in FIGS. 16-17, 19, and 21, tissue sample holder (140) of the present example has a passage (158) formed through manifold (144). Passage (158) extends longitudinally, completely through manifold (144), and is offset from but parallel with the central axis defined by manifold (144). Like chambers (166), passage (158) is configured to be selectively aligned with cutter lumen (52). However, unlike chambers (166), passage (158) is not in fluid communication with any of longitudinal passages (148) or radial passages (154). In other versions, passage (158) may be provided in fluid communication with one or more longitudinal passages (148) and/or radial passages (154).

Passage (158) of the present example is configured to permit instruments and/or liquids, other materials, etc., to be passed through manifold (144) and through cutter lumen (52). For instance, passage (158) may be used to insert an instrument for deploying one or more markers at a biopsy site, via cutter lumen (52) and via outer cannula (12), out through aperture (16). A merely exemplary marker applier that may be inserted through passage (158) may include the MAMMOMARK biopsy site marker applier, by Ethicon Endo-Surgery, Inc. of Cincinnati, Ohio. Other suitable marker applier devices that may be inserted through passage (158) may include any of those described in U.S. Pat. Nos. 7,047,063; 6,996,433; 6,993,375; or U.S. Pub. No. 2005/0228311, the disclosure of each of which is incorporated by reference herein. Any of such appliers, including variations of the same, may be introduced through passage (158) to deploy one or more markers at a biopsy site, via aperture (16), while needle portion (10) remains inserted in a patient (e.g., shortly after biopsy samples are extracted from the patient, etc.). Such marker deployment may be accomplished even while tissue samples (4) reside within tissue sample holder (140), secured to biopsy probe (102). Alternatively, such marker appliers may be inserted directly into cutter lumen (52) with tissue sample holder (140) being removed from biopsy probe (102).

As noted above, biopsy probe (102) may be initially provided with a predetermined chamber (166) being aligned with cutter lumen (52) by default. However, in other versions, biopsy probe (102) is initially provided with passage (158) being aligned with cutter lumen (52) by default. Furthermore, to the extent that a user desires having passage (158) aligned with cutter lumen (52) during use of biopsy device (100), after manifold (144) has been rotated during such use, the controls may be used to command manifold (144) to rotate to align passage (158) with cutter lumen (52).

Cup (142) further comprises an opening (176) and a hatch (178). Opening (176) is configured to be aligned with passage (158) when cup (142) is secured to base member (116), such as by rotating manifold (144) to align passage (158) with opening (176). Hatch (178) is configured to selectively cover opening (176). For instance, hatch (178) may be configured to seal opening (176) when hatch (178) covers opening (176). Hatch (178) may further be configured to permit a user to "peel back" hatch (178) and/or pivot hatch (178) in order to gain access to opening (176) and passage (158). It will be appreciated in view of the disclosure herein that hatch (178) may be substituted or supplemented with a variety of alternative structures, including but not limited to a removable stopper or other structure.

L. Exemplary Medicine Applier

Figure 21:
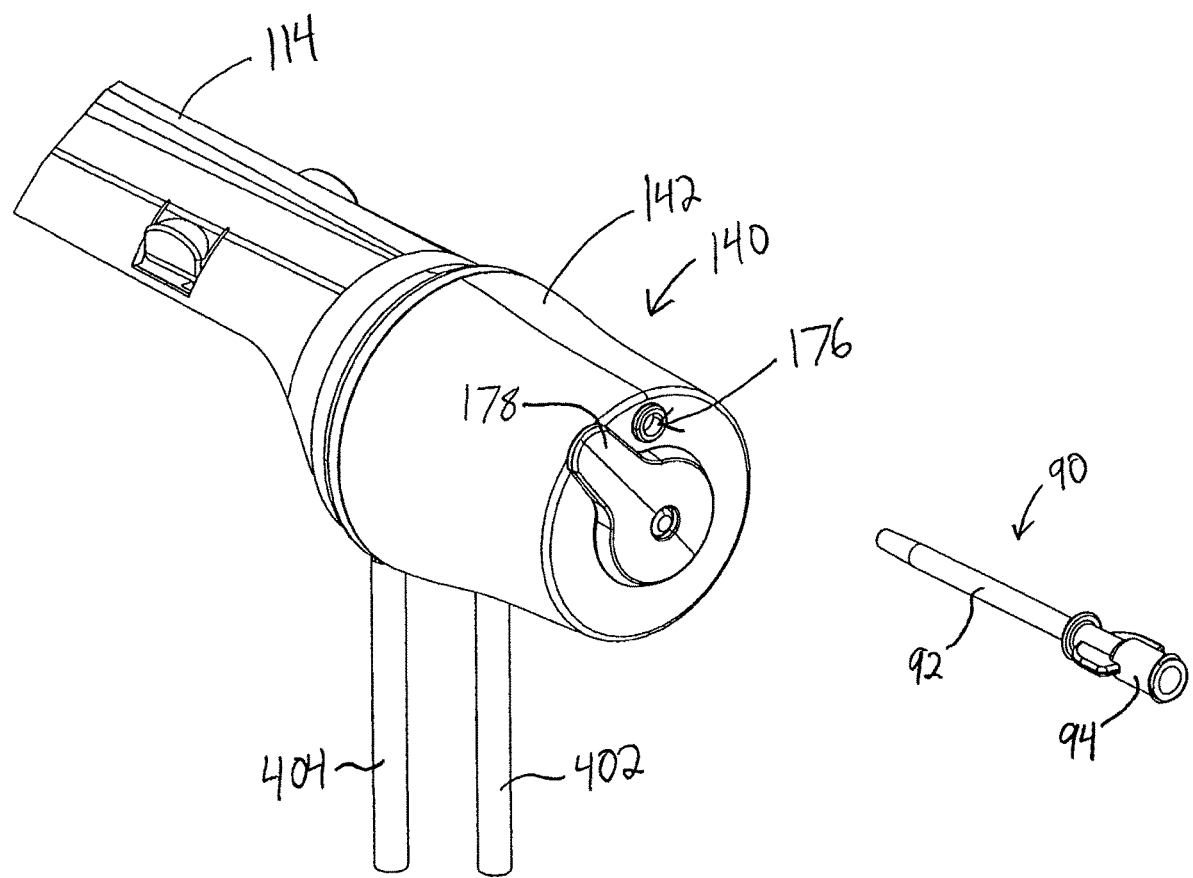
FIG. 21 depicts an exploded view of an applier and the tissue sample holder of FIG. 15.
Figure 22:
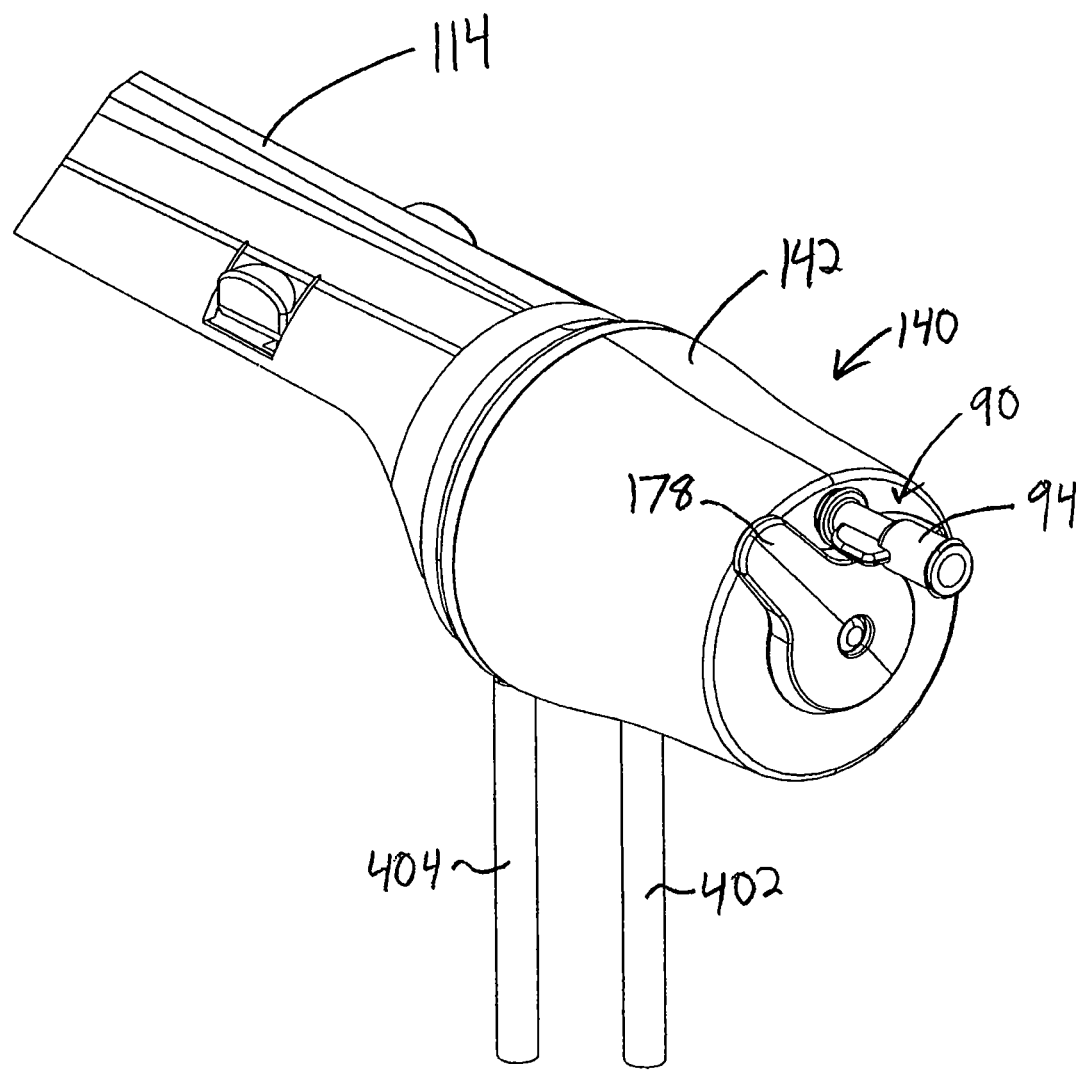
FIG. 22 depicts a perspective view of the applier of FIG. 21 inserted in the tissue sample holder of FIG. 15.
Figure 23:
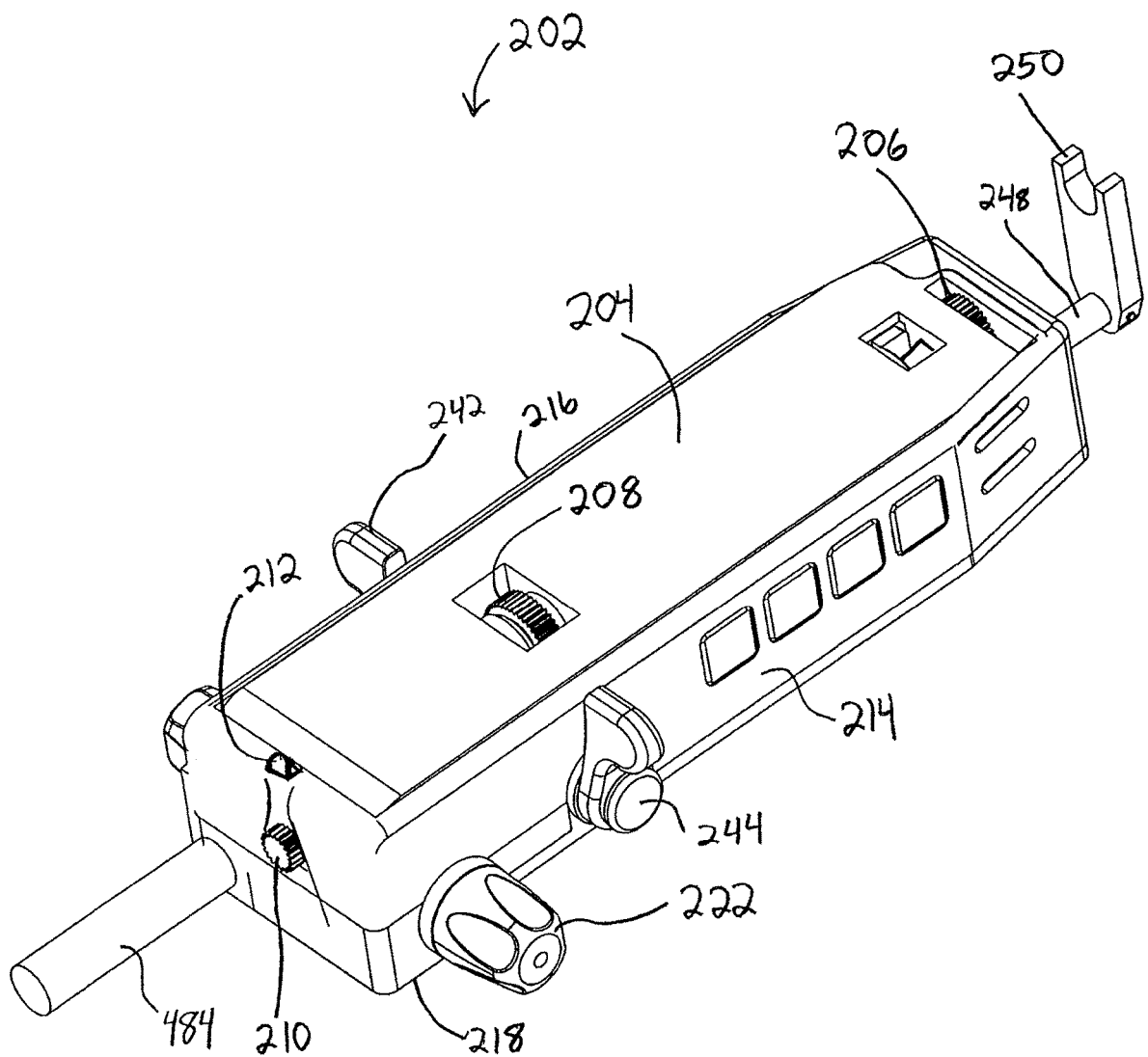
FIG. 23 depicts a perspective view of a holster of the biopsy device of FIG. 2.
Figure 24:
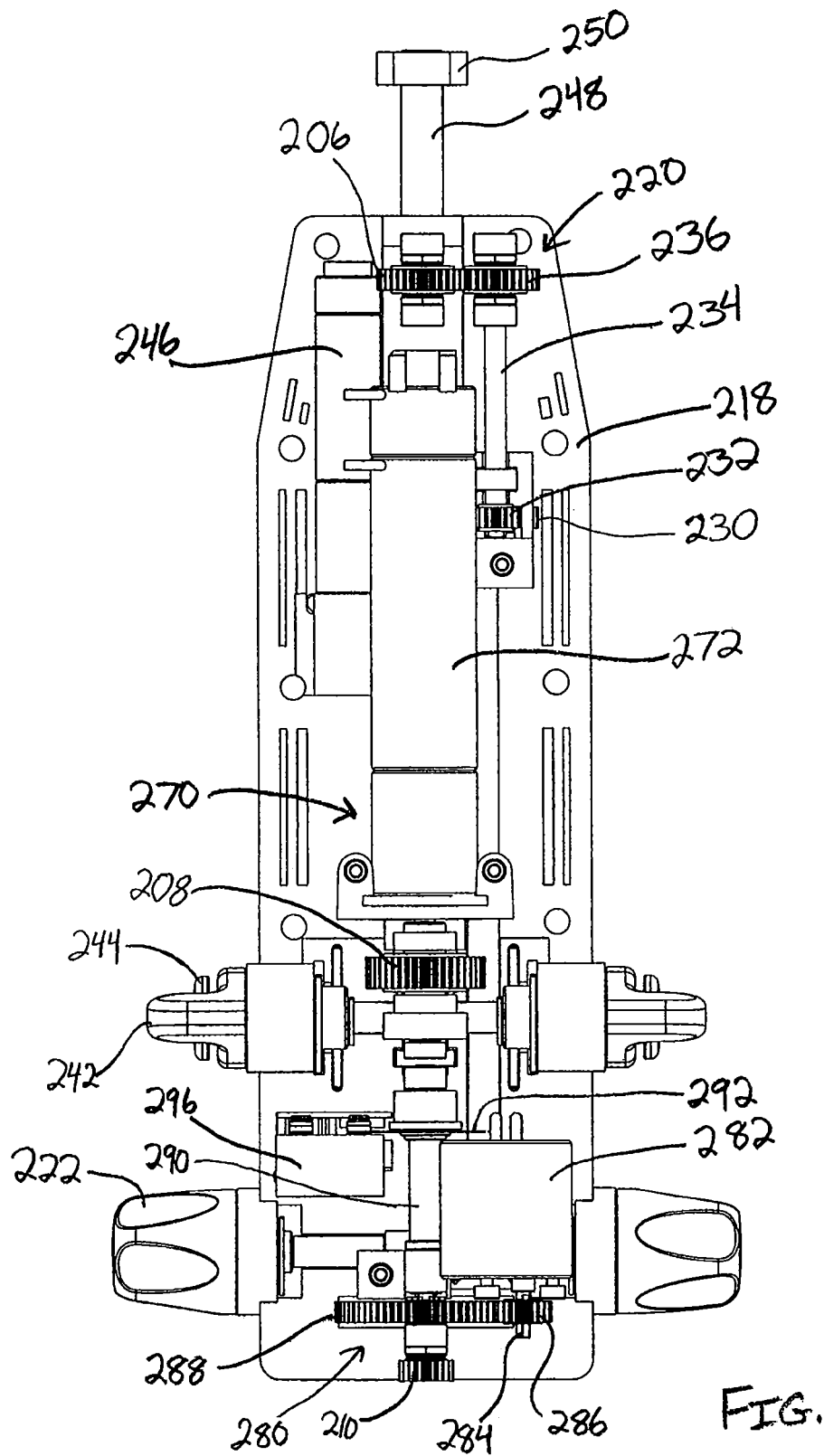
FIG. 24 depicts a top view of the holster of FIG. 23, with a top cover removed.
Figure 25:
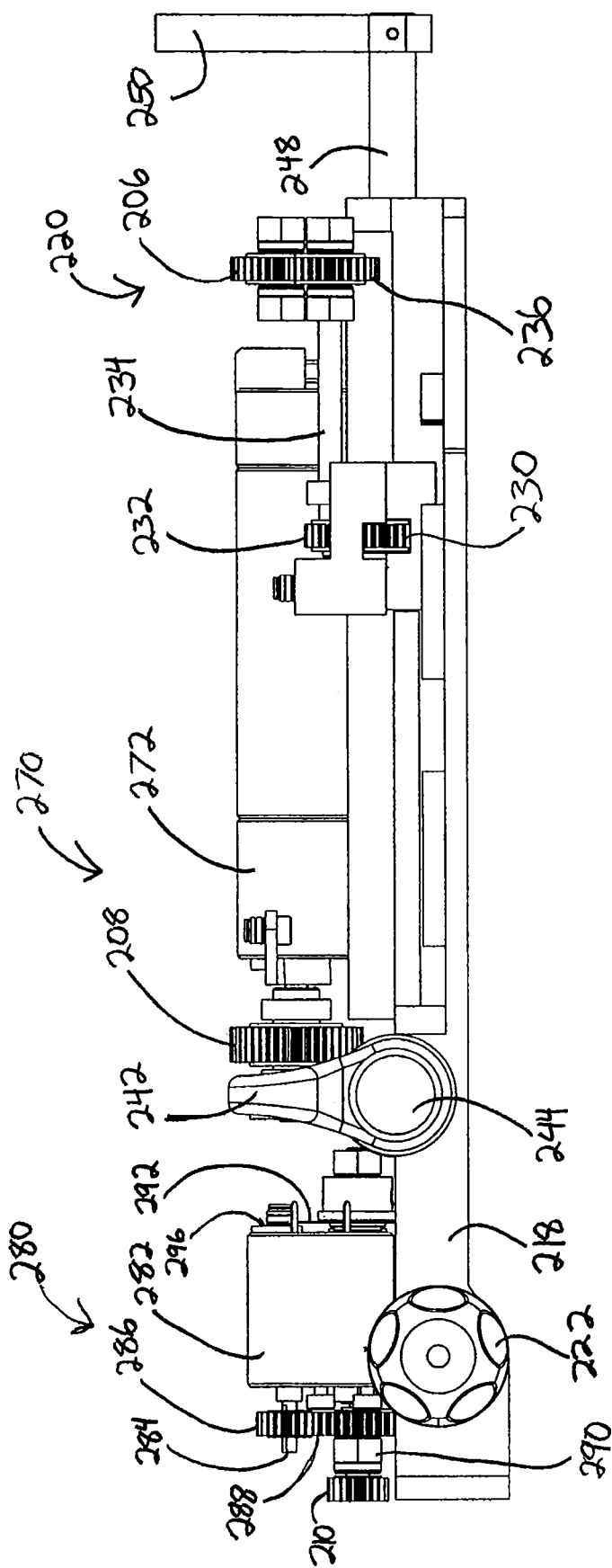
FIG. 25 depicts a side view of the holster of FIG. 23, with side panels removed.
Figure 26:
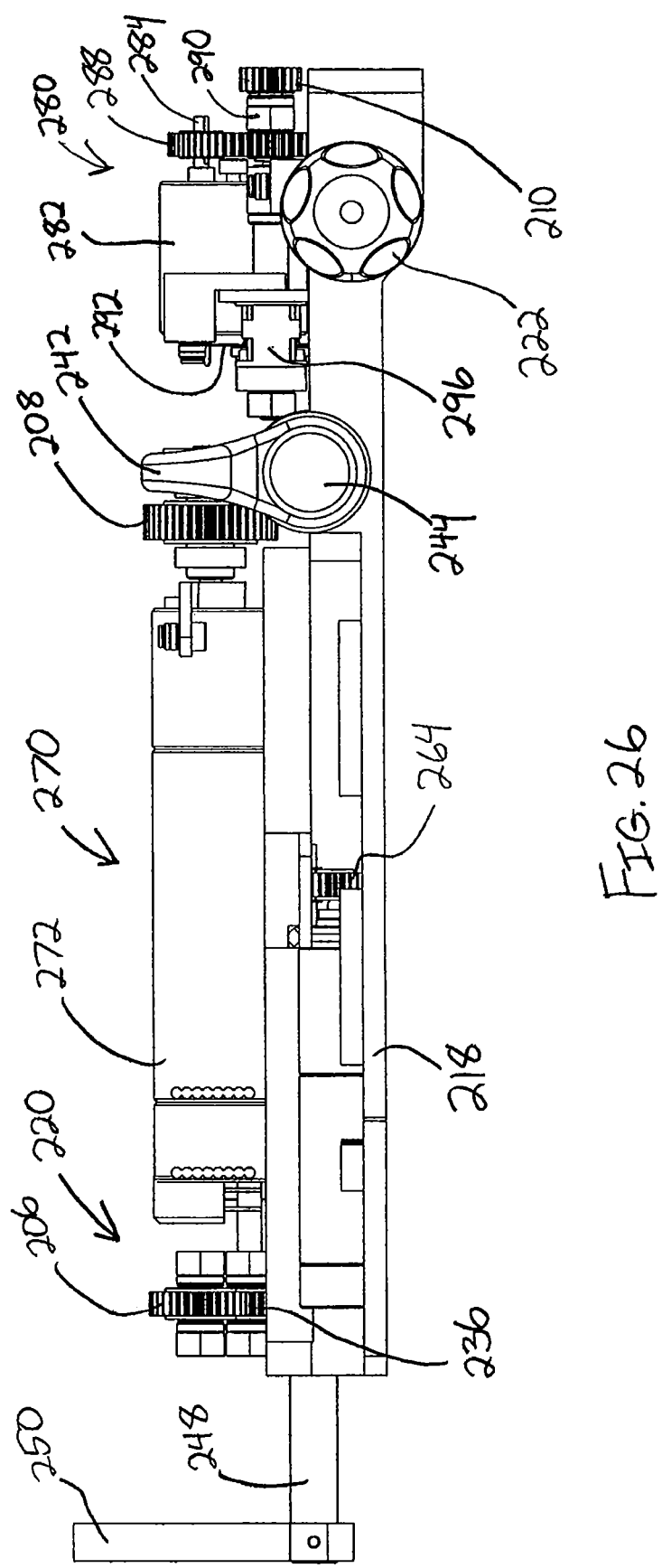
FIG. 26 depicts another side view of the holster of FIG. 23, with side panels removed.

As shown in FIGS. 21-22, an applier (90) may be coupled with biopsy probe (102) via opening (176) in cup (142) and passage (158) in manifold (144). In this example, applier (90) comprises a hollow shaft portion (92) and a luer lock portion (94). Shaft portion (92) is sized and configured such that, when applier (90) is inserted through opening (176) and through passage (158), shaft portion (92) creates a seal with cutter lumen (52) (e.g., through engagement with the inner surface of cutter lumen (52)). Shaft portion (92) and luer lock portion (94) may thereby be placed in fluid communication with cutter lumen (52). By way of example only, a syringe (not shown) or other device may be coupled with luer lock portion (94). A therapeutic agent may thus be injected from such a syringe, through applier (90), through cutter lumen (52), through outer cannula (12), and out through aperture (16) to reach a biopsy site. Such injections may be made before or after tissue samples (4) are acquired using biopsy device (100), and may be made while needle portion (10) remains inserted in the patient. Other suitable ways in which an applier (90) may be used, as well as alternative ways in which an applier (90) may be configured, will be apparent to those of ordinary skill in the art in view of the teachings herein. By way of example only, applier

(90) may alternatively be inserted directly into cutter lumen (52) with tissue sample holder (140) being removed from biopsy probe (102).

II. Exemplary Holster for Stereotactic Use

As shown in FIGS. 23-32, a holster (202) comprises a top cover (204), through which a portion of each of gears (206, 208, 210) is exposed, side panels (214, 216), and a base member (218). As described above, boss (212) is provided on top cover (204), and is configured to disengage pawl portion (182) from gear (170) when biopsy probe (102) is coupled with holster (202). Holster (202) of this example further comprises a needle rotation mechanism (220), a needle firing mechanism (240), a cutter drive mechanism (270), and a tissue holder rotation mechanism (280). In addition, a user interface (800) is provided on each side panel (214, 216). Each of these merely exemplary components will be described in greater detail below.

As noted above, holster (202) of the present example is configured to be coupled with a biopsy probe (102), such as biopsy probe (102) described above, to provide a biopsy device (100). In addition, holster (202) is configured to be mounted to a table, fixture, or other device, such as for use in a stereotactic or X-ray setting. However, it will be appreciated in view of the disclosure herein that holster (202) may be used in a variety of other settings and combinations.

A. Exemplary Needle Rotation Mechanism

Figure 27:
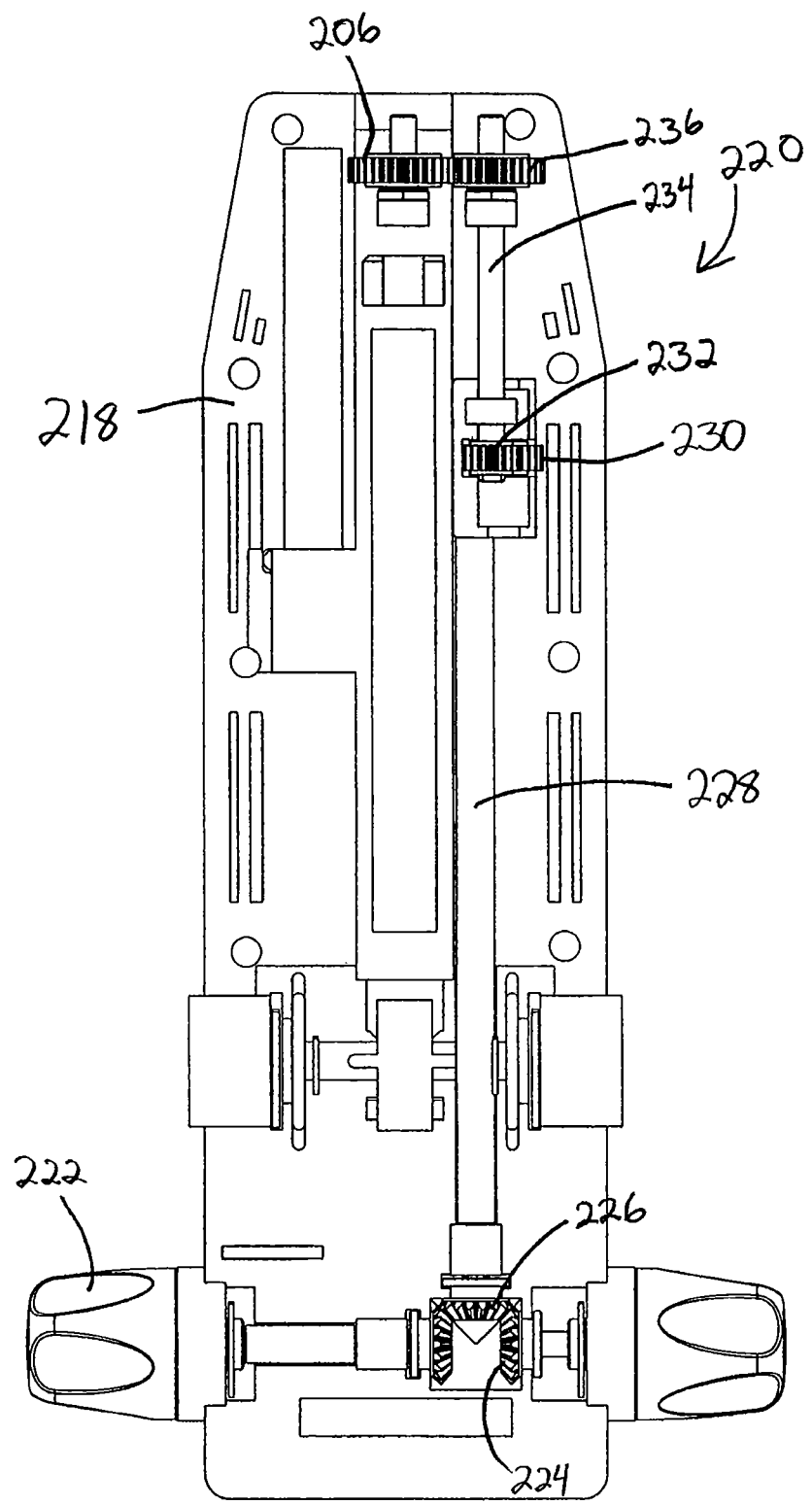
FIG. 27 depicts a partial view of the holster of FIG. 23, showing an exemplary needle rotation mechanism.

In the present example, and as shown in FIG. 27, needle rotation mechanism (220) comprises a pair of knobs (222), each of which has a respective gear (224) in beveled engagement with a gear (226) on the proximal end of an elongate shaft (228). Another gear (not shown), which is provided on the distal end of shaft (228), is engaged with gear (230). Gear (230) is engaged with yet another gear (232) on the proximal end of yet another shaft (234). The distal end of shaft (234) has another gear (236), which is engaged with gear (206) described above. It will therefore be appreciated in view of the disclosure herein that rotation of one or both of knobs (222) will result in rotation of gear (206), with such rotation being communicated via gears (224, 226, 230, 236) and shafts (228, 234). Furthermore, as also noted above, when biopsy probe (102) is coupled with holster (202), gear (206) will mesh with gear (74). Thus, when biopsy probe (102) is coupled with holster (202), rotation of one or both of knobs (222) will cause needle portion (10) of biopsy probe (102) to rotate. Of course, a variety of alternative mechanisms, structures, or configurations may be used as a substitute or supplement for needle rotation mechanism (220). By way of example only, a motor (not shown) may be used to effect rotation of needle portion (10). In other versions, needle rotation mechanism (220) may simply be omitted altogether.

B. Exemplary Needle Firing Mechanism

Figure 28:
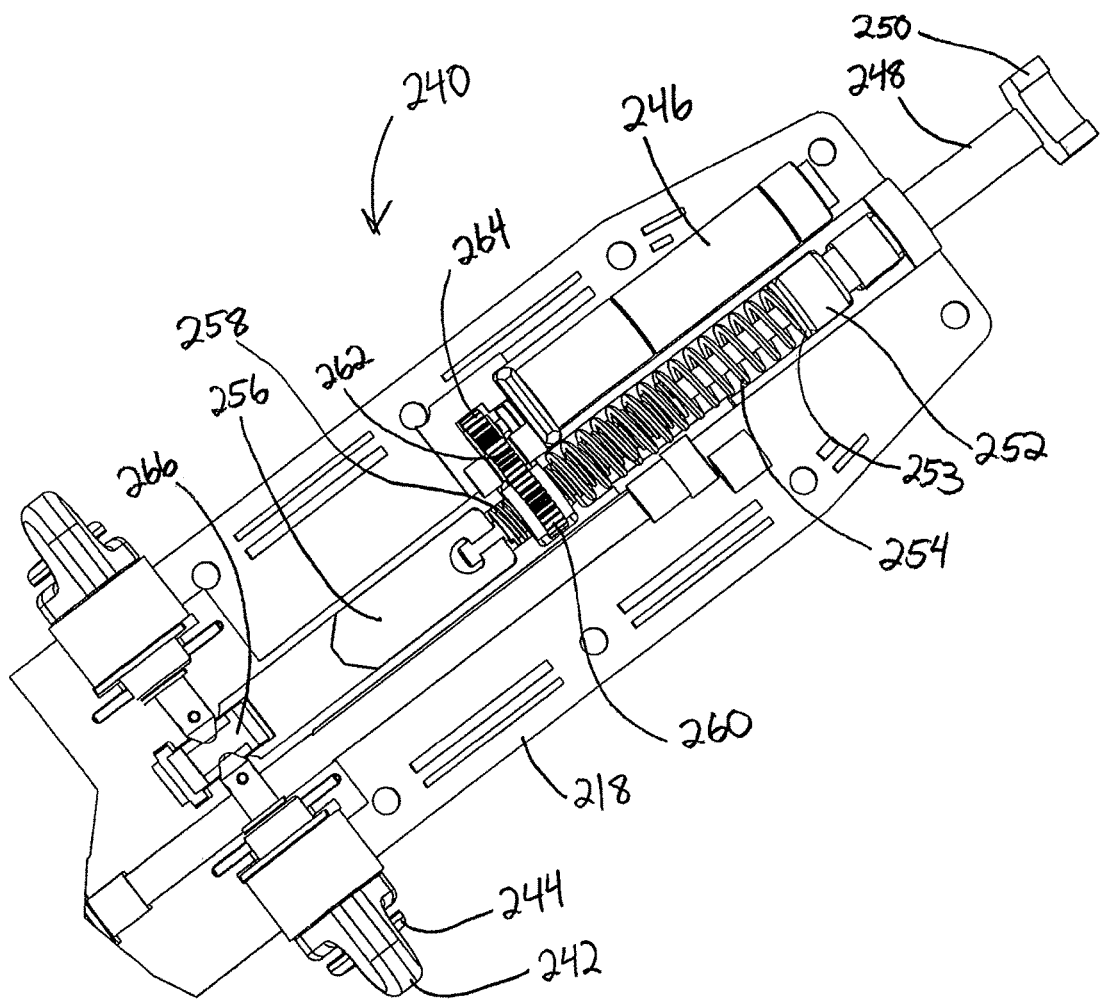
FIG. 28 depicts a partial view of the holster of FIG. 23, showing an exemplary needle firing mechanism.
Figure 29:
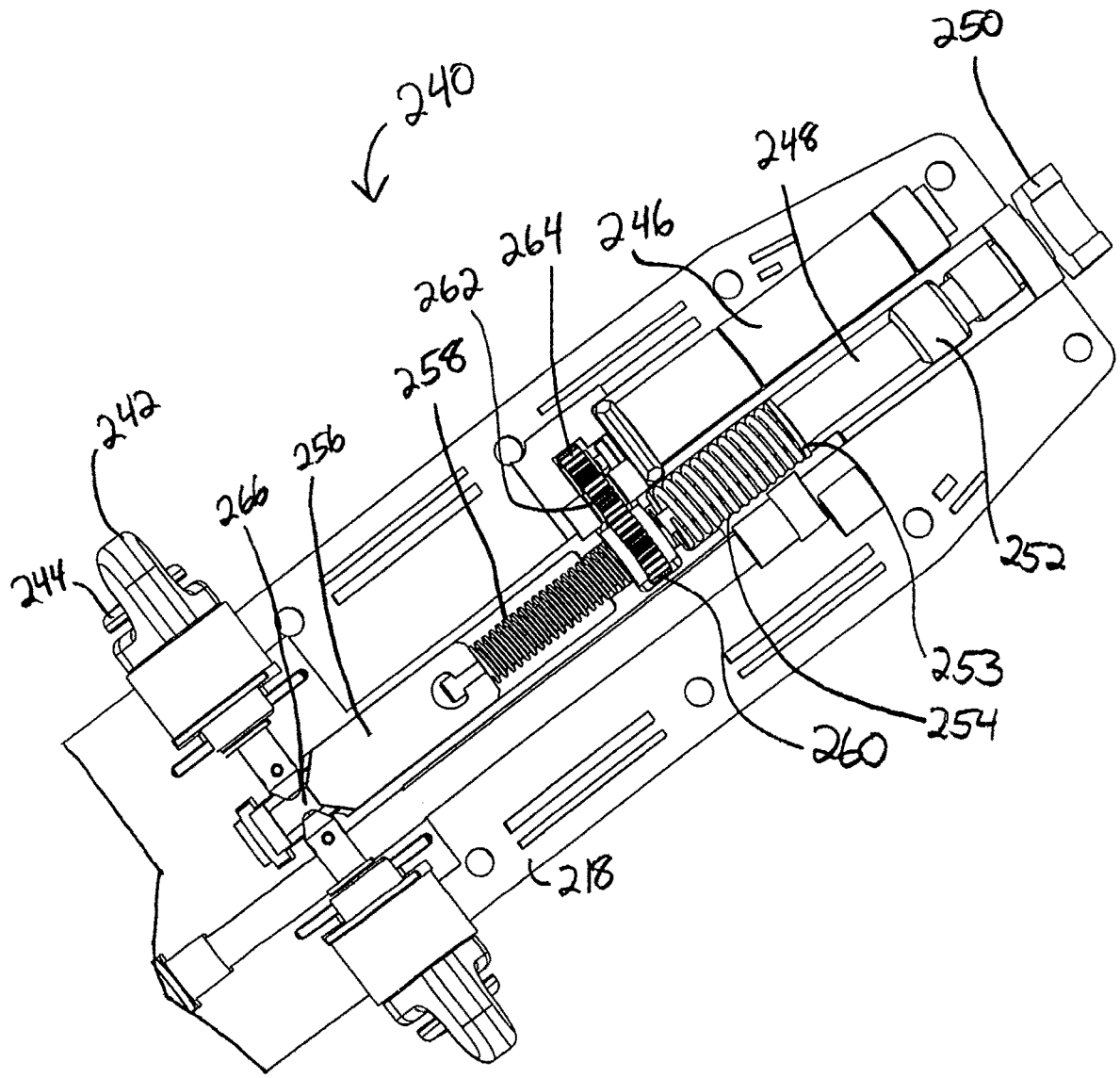
FIG. 29 depicts a partial view of the holster of FIG. 23, showing an exemplary needle firing mechanism in a cocked configuration.

As shown in FIGS. 28-29, needle firing mechanism (240) of the present example comprises a pair of triggers (242), buttons (244), a motor (246), a firing rod (248), and a fork (250). Fork (250) is configured to engage sleeve portion (64) of needle hub (60) when biopsy probe (102) is coupled with holster (202). For instance, fork (250) may engage sleeve portion (64) between thumbwheel (62) and annular projection (66). In the present example, engagement between fork (250) and sleeve portion (64) is such that sleeve portion (64) (and therefore, needle portion (10)) will translate longitudinally with fork (250). Fork (250) is coupled with firing rod (248), such that fork (250) will translate longitudinally with firing rod (248).

A damper (252) with a washer (253) is provided about firing rod (248). A coil spring (254) is also provided about firing rod (248). In particular, coil spring (254) is engaged with both washer (253) and a portion of base member (218). Coil spring (254) is biased to urge damper (252), washer (253), and firing rod (248) distally. It will be appreciated, however, that like other components described herein, coil spring (254) is merely exemplary, and a variety of alternative components (resilient or otherwise) may be used in addition to or in lieu of coil spring (254).

A sled (256) and a screw gear (258) are also coupled with firing rod (248). In particular, sled (256) is coupled with the proximal end of firing rod (248), and is configured to longitudinally translate unitarily with firing rod (248). Similarly, screw gear (258) is configured to longitudinally translate with firing rod (248) (through at least some range of motion), while being prevented from rotating about firing rod (248). An outer gear (260) is engaged with screw gear (258). In particular, the interior (not shown) of outer gear (260) is engaged with the threads of screw gear (258); such that when outer gear (260) rotates relative to screw gear (258), such rotation causes screw gear (258) to longitudinally translate relative to outer gear (260). Outer gear (260) is in communication with another gear (262), which is itself in communication with a gear (264) that is coupled with motor (246). Accordingly, when motor (246) is activated to rotate, such rotation will cause screw gear (258), firing rod (248), and sled (256) to longitudinally translate. In other words, rotation of motor (246) will be communicated to outer gear (260) via gears (262, 264), and such rotation will be converted to longitudinal motion due to the configuration and engagement of outer gear (260) and screw gear (258). Of course, all of these components are merely illustrative, and any other suitable components, configurations, or techniques may be used to cause longitudinal translation of firing rod (248).

Triggers (242) of the present example are each configured to partially rotate forward and rearward, while buttons (244) are configured to be pressed inward. In addition, a plurality of switches (not shown) may be communicatively coupled with triggers (242) and/or buttons (244), such that the switches are selectively activated by a user when triggers (242) are moved forward or rearward and/or when buttons (244) are depressed. One or more resilient members (e.g., a spring, etc.) may be included to bias each trigger (242) to a centered or substantially vertical orientation. One or more resilient members (e.g., a spring, etc.) may also be included to bias each button (244) to an outward position. Triggers (242) and buttons (244) are also sealed in the present example to prevent ingress of fluid into holster (202), though like other features, this is merely optional.

In the present example, triggers (242) are further configured such that, when one or both of triggers (242) are moved rearward, such movement activates a switch that is in communication with motor (246). Such activation causes motor (246) to rotate, which in turn causes firing rod (248) to longitudinally translate proximally as described above. As will be described in greater detail below, such rearward movement of trigger (242) may thus cause motor (246) to arm or "cock" the needle firing mechanism (240).

Needle firing mechanism (240) of the present example further comprises a catch (266), which is configured to selectively engage sled (256). In particular, as firing rod (248) and sled (256) are longitudinally translated proximally (e.g., by rotation of motor (246)), sled (256) approaches catch (266). When catch (266) and sled (256) engage, catch (266) is configured to hold sled (256) (and therefore, firing rod (248)) in place. Catch (266) may maintain such position of sled (256) even after motor (246) has stopped rotating, and even with spring (254) urging sled (256) and firing rod (248) toward a distal position. When these components are in these proximal positions and configurations, needle firing mechanism (240) may be said to be in a "cocked" configuration. A merely exemplary cocked configuration of needle firing mechanism (240) is shown in FIG. 29.

It will be appreciated in view of the teachings herein that, with needle firing mechanism (240) in such a cocked configuration, fork (250) and needle portion (10) will be at a proximal, ready-to-fire position. One or more components of biopsy device (100) may be configured to provide an audio and/or visual indication that the needle firing mechanism (240) is fully cocked. For instance, biopsy device (100) may produce a distinct clicking sound, beep, or other audible signal; and/or a graphical user interface may provide some visual indication that the needle firing mechanism (240) is cocked.

In addition, holster (202) may further include one or more sensors (not shown) or other feature(s) configured to sense or detect when needle firing mechanism (240) has been cocked and/or when needle firing mechanism (240) has been fired. For instance, biopsy system (2) may be configured such that one or more functions of biopsy system (2) are essentially disabled while needle firing mechanism (240) is cocked, until needle firing mechanism (240) is fired. By way of example only, biopsy system (2) may prevent initiation of a "sample" cycle (described below), initiation of a "clear probe" cycle (described below), or other functions while needle firing mechanism (240) is cocked. Such functions may be again permitted after needle firing mechanism (240) has been fired and after needle (10) has reached a fully fired position. Alternatively, cocking of needle firing mechanism (240) may have no affect or other affects on one or more functions of biopsy system (2).

In one variation, after sled (256) has been moved into engagement with catch (266) to cock needle firing mechanism (240), motor (246) may reverse its rotation. In this variation, a proximal portion of firing rod (248) may have a longitudinal slot or recess (not shown) formed transversely through or in firing rod (248). Screw gear (258) may have an internal pin or other feature (not shown) that is configured to engage such a slot or other feature of firing rod (248), such that the pin or other feature of screw gear (258) is further configured to both prevent screw gear (258) from rotating about firing rod (248) and permit screw gear (258) to translate through some range of motion relative to firing rod (248). For instance, before needle firing mechanism (240) is cocked, such a pin or other feature of screw gear (258) may be positioned at or near the proximal end of a longitudinal slot or recess of firing rod (248); such that as motor (246) is activated to translate screw gear (258) proximally to cock needle firing mechanism (240), the pin or other feature engages firing rod (248) to urge firing rod (248) proximally with screw gear (258). Then, after sled (256) has been moved proximally into engagement with catch (266), motor (246) may reverse its rotation. Such reversal of motor (246) rotation may translate screw gear (258) distally. The configuration of the slot or other feature of firing rod (248) and the configuration of the pin or other feature of screw gear (258) may permit such distal translation of screw gear (258) relative to firing rod (248), leaving firing rod in a proximal cocked position. Furthermore, when needle portion (10) is fired as described below, the configuration of the slot or other feature of firing rod (248) and the configuration of the pin or other feature of screw gear (258) may permit firing rod (248) to translate distally relative to screw gear (258) with relative ease during such firing. Other suitable relationships between firing rod (248) and screw gear (258) may be used, including but not limited to a variation described below.

When a user is ready to fire needle portion (10), the user may push and hold one or both of triggers (242) forward, and may push one or both buttons (244) in while one or both of triggers (242) are held forward. Such actuation of trigger(s) (242) and button(s) (244) may cause catch (266) to release sled (256). Suitable structures and configurations that may be used to cause actuation of trigger(s) (242) and button(s) (244) to result in catch (266) releasing sled (256) will be apparent to those of ordinary skill in the art in view of the teachings herein. With sled (256) being so released, the resilience of spring (254) may urge damper (252) and washer (253) (and therefore, firing rod (248), fork (250), and needle portion (10)) distally, thereby firing needle portion (10). Such distal motion of needle portion (10) may be relatively sudden, and may be performed with a force sufficient to penetrate tissue with tip (14) of needle portion (10).

In another variation, motor (246) does not reverse its rotation to advance screw gear (258) back to a distal position before needle portion (10) is fired. For instance, screw gear (258) may be unitarily secured to firing rod (248), and may be unable to translate longitudinally in either direction through any range of motion relative to firing rod (248). In this variation, as needle portion (10) is fired, gears (260, 262, 264) may be configured to rotate freely, thereby providing negligible resistance to distal motion of firing rod (248). Alternatively, a clutch mechanism (not shown) may be provided to disengage one or more of gears (260, 262, 264) during firing of needle portion (10). Other ways in which a needle firing mechanism (240) may be configured or operated will be apparent to those of ordinary skill in the art in view of the teachings herein.

In the present example, triggers (242) and buttons (244) are configured such that pushing or actuation of buttons (244) will have no firing effect unless triggers (242) are held forward. Similarly, holding of triggers (242) will not cause firing of needle portion (10) until buttons (244) are also pressed while triggers (242) are held forward. Suitable structures and configurations for providing such interdependence of triggers (242) and buttons (244) will be apparent to those of ordinary skill in the art. For instance, buttons (244) may rotate with triggers (242), such that buttons (244) rotate forward with triggers (242). In such versions, buttons (244) and catch (266) may be configured such that actuation of buttons (244) will not cause catch (266) to release sled (256) unless buttons (244) are rotated forward. In addition or in the alternative to buttons (244) rotating with triggers (242), triggers (242) may be configured to lock catch (266) in place (e.g., even with buttons (244) being actuated) until triggers (242) are rotated forward, such that forward rotation of triggers (242) will permit catch (266) to be released when buttons (244) are actuated. Other ways in which triggers (242) and buttons (244) may be provided as interdependent for purposes of firing (or for other purposes) will be apparent to those of ordinary skill in the art in view of the teachings herein.

C. Exemplary Cutter Drive Mechanism

Figure 30:
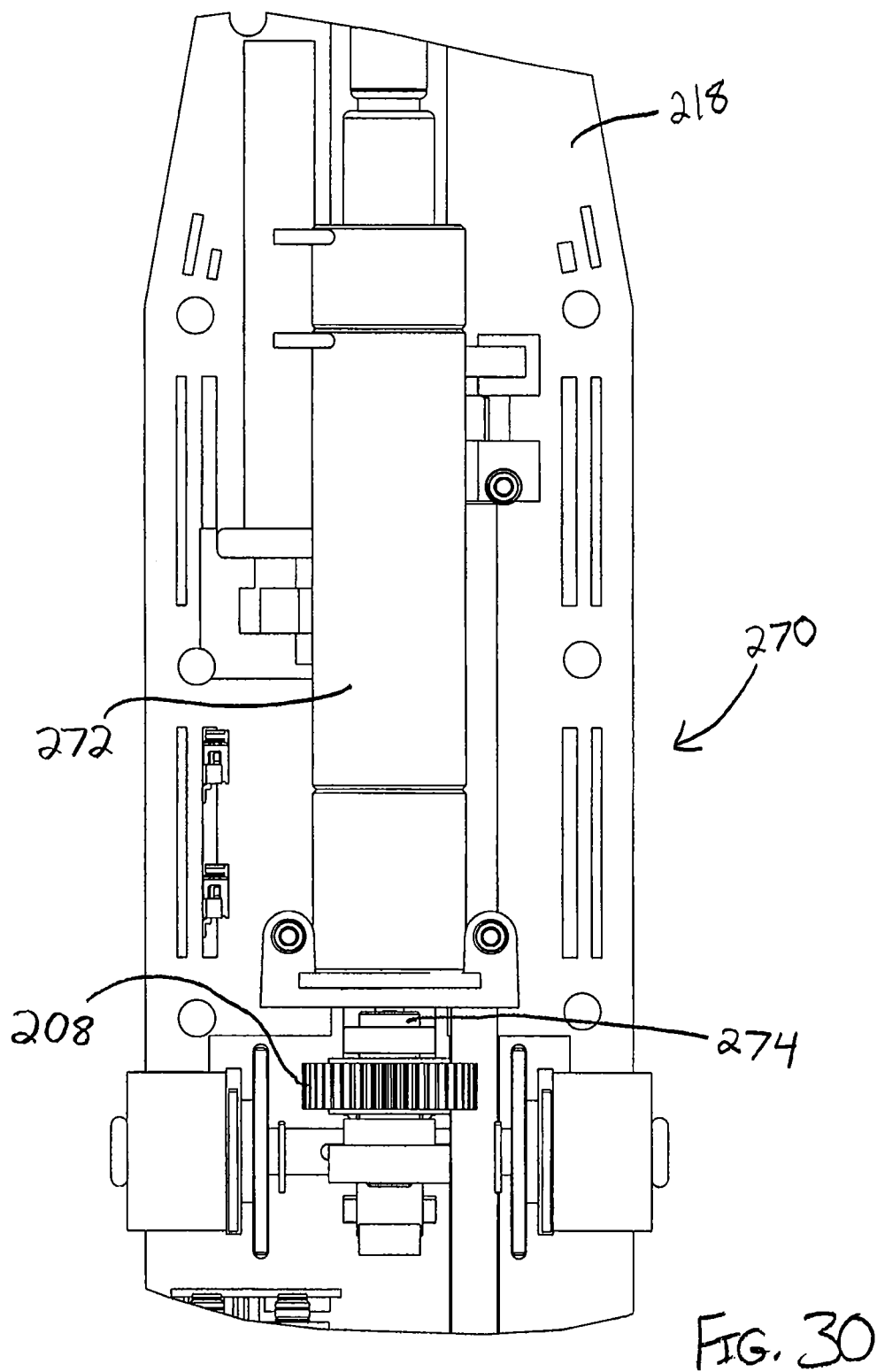
FIG. 30 depicts a partial view of the holster of FIG. 23, showing an exemplary cutter drive mechanism.

As shown in FIG. 30, cutter drive mechanism (270) of the present example comprises a motor (272) with a shaft (274) extending therefrom. Gear (208) is mounted to shaft (274), and is configured to rotate unitarily therewith. As noted above, a portion of gear (208) is exposed through top cover (204), such that gear (208) meshes with gear (138) of cutter rotation and translation mechanism (120) when biopsy probe (102) is coupled with holster (202). Accordingly, when motor (272) is activated to rotate, such rotation may be communicated via shaft (274) and gears (208, 138), to effect simultaneous rotation and translation of cutter (50) as described above. Other ways in which a cutter drive mechanism (270) may be configured or operated will be apparent to those of ordinary skill in the art in view of the teachings herein.

D. Exemplary Tissue Holder Rotation Mechanism

Figure 31:
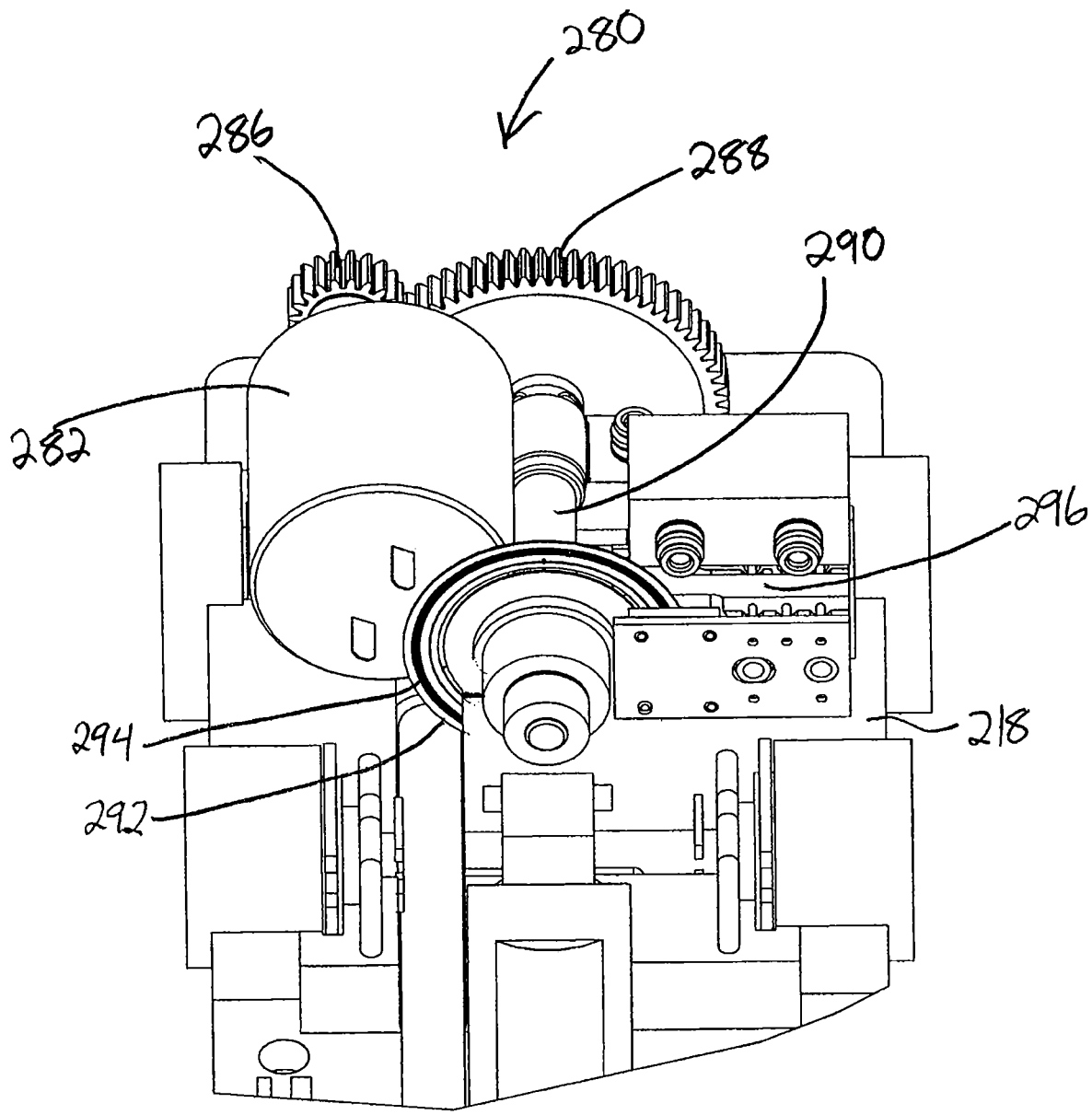
FIG. 31 depicts a partial view of the holster of FIG. 23, showing an exemplary tissue holder rotation mechanism.
Figure 32:
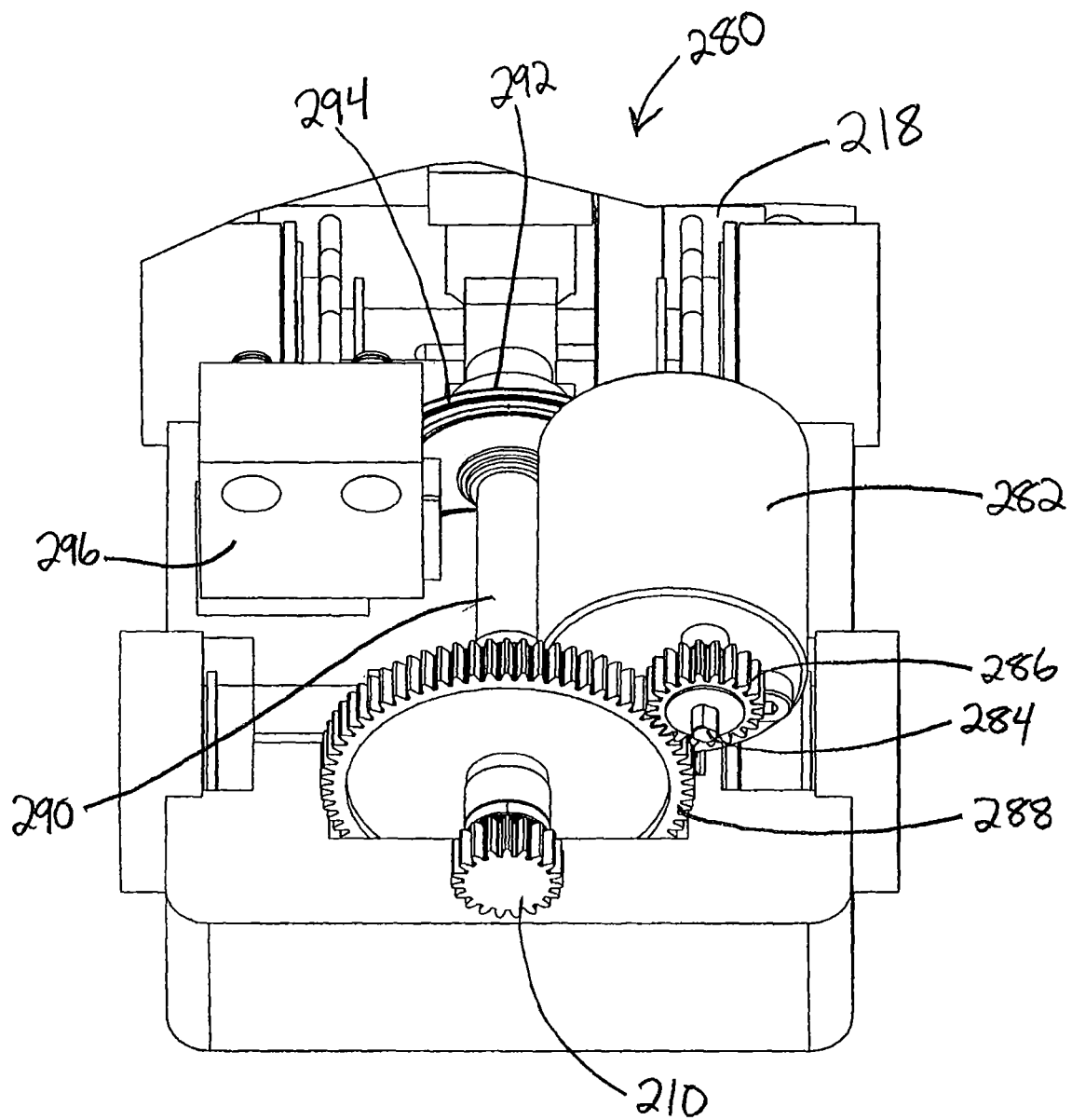
FIG. 32 depicts another partial view of the holster of FIG. 23, showing an exemplary tissue holder rotation mechanism.
Figure 33:
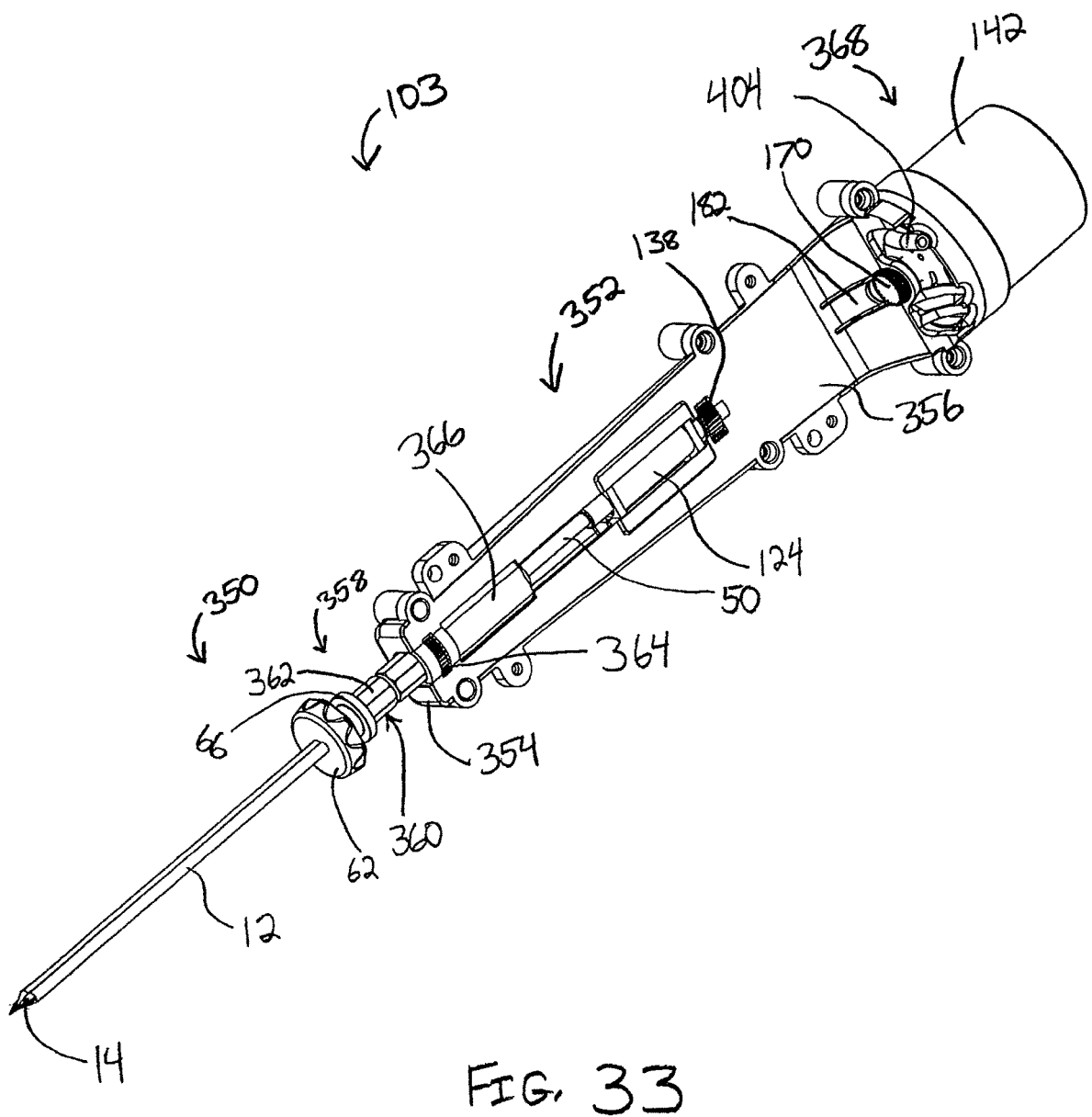
FIG. 33 depicts a bottom perspective view of the probe portion of the biopsy device of FIG. 4.

As shown in FIGS. 31-32, tissue holder rotation mechanism (280) of the present example comprises a motor (282) having a shaft (284) with a gear (286) mounted thereto, such that gear (286) rotates unitarily with shaft (284). Gear (286) is configured to mesh with gear (288), which is mounted to shaft (290). Gear (210), which has been noted above, is also mounted to shaft (290), at the proximal end of shaft (290). In particular, gear (210) is configured to mesh with gear (170) of tissue sample holder (140) when biopsy probe (102) is coupled with holster (202). Accordingly, when motor (282) is activated to rotate, such rotation may be communicated via shafts (284, 290) and gears (286, 288, 210, 170), to effect rotation of manifold (144) as described above.

In addition, an encoder wheel (292) is coupled with shaft (290), and is configured to rotate unitarily therewith. Encoder wheel (292) has a plurality of slots (294) formed therethrough. Slots (294) fan radially outward, and are angularly spaced apart relative one another. Of course, slots (294) may have any other suitable configuration. A sensor (296) is positioned adjacent to encoder wheel (292). In particular, sensor (296) is positioned such that slots (294) successively pass before sensor (296) as encoder wheel (292) rotates with shaft (290). Sensor (296) may therefore be used to count the passage of slots (294), which may be translated into data indicative of the rotational position of manifold (144). In other words, since encoder wheel (292) and manifold (144) rotate concomitantly when biopsy probe (102) is coupled with holster (202) in the present example, the passage of slots (294) past sensor (296) during rotation of shaft (290) may be indicative of manifold (144) rotation, and therefore of manifold (144) position. It will be appreciated that information indicative of manifold position (144) may be further indicative of which particular chamber (166) is aligned with cutter lumen (52). Suitable uses for such information will be apparent to those of ordinary skill in the art in view of the teachings herein.

Suitable devices that may be used for sensor (296) will also be apparent to those of ordinary skill in the art in view of the teachings herein. Similarly, suitable substitutes for encoder wheel (292) and sensor (296) will be apparent to those of ordinary skill in the art, including but not limited to combinations of magnets and hall effect sensors, light sources and photosensors, etc. Furthermore, other ways in which a tissue holder rotation mechanism (280) may be configured or operated will be apparent to those of ordinary skill in the art in view of the teachings herein.

III. Exemplary Probe for Ultrasound Use

As shown in FIGS. 33-37, an alternative biopsy probe (103) comprises a needle portion (350) and a body portion (352). Body portion (352) comprises a cover member (354) and a base member (356). A tissue sample holder (368) is removably secured to base member (356), though tissue sample holder (368) may alternatively be secured to cover member (354) or some other component. As will be described in greater detail below, a pair of tubes (402, 404) are coupled with probe (103). As will also be described in greater detail below, and as noted above, biopsy probe (103) is configured to be coupled with a holster (302) to provide a biopsy device (101).

A. Exemplary Needle

In the present example, needle portion (350) comprises an outer cannula (12) having a tissue piercing tip (14) and a transverse tissue receiving aperture (16) located proximally from the tissue piercing tip (14). In this example, these components are essentially the same as the components bearing the same names and item numbers described above, so they will not be described in greater detail here. In other words, the features, properties, and components of outer cannula (12), tip (14), and aperture (16) as described above (including cannula lumen (20), vacuum lumen (40), wall (30), transverse openings (32), etc.) may be the same for needle portion (350) as they were described above with respect to needle portion (10). Of course, they may alternatively be varied in any suitable way, as desired.

Similarly, cutter (50) in probe (103) may have the same relationship with needle portion (350) as the relationship described above between cutter (50) and needle portion (10); as well as all the same features, properties, and components as cutter (50) described above in the context of probe (102). Such aspects of cutter (50) will also therefore not be repeated here.

B. Exemplary Needle Hub

Figure 36:
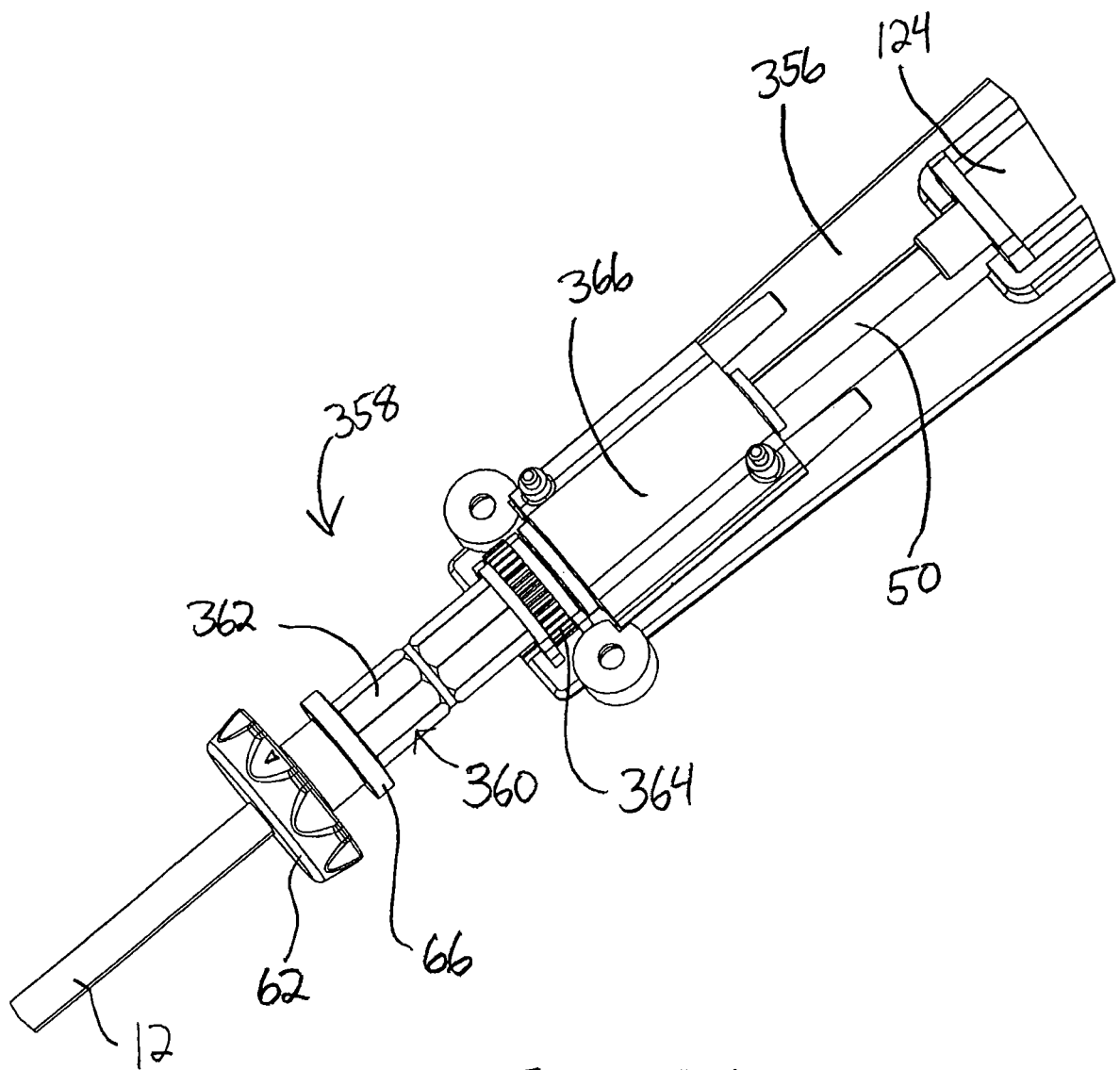
FIG. 36 depicts a partial perspective view of the probe portion of FIG. 33, showing a needle hub assembly.
Figure 37:
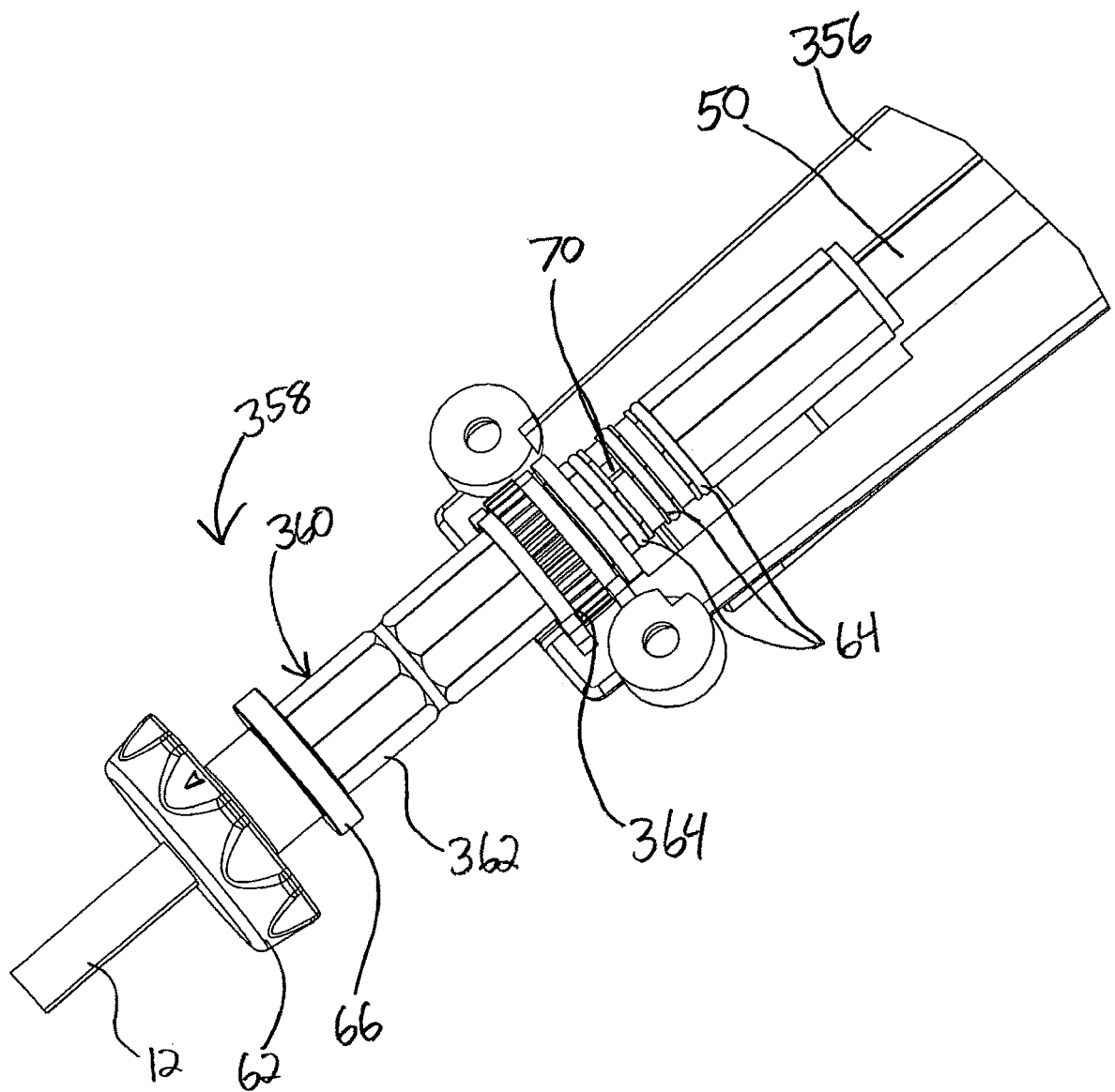
FIG. 37 depicts a partial perspective view of the probe portion of FIG. 33, showing a needle hub assembly with a needle manifold removed.

As shown in FIGS. 36-37, a needle hub (358) is secured to outer cannula (12) of probe (103), and comprises a thumbwheel (62) and a sleeve portion (360) extending proximally from thumbwheel (62). Needle hub (358) of the present example is overmolded about a proximal portion of outer cannula (12), though needle hub (358) may be formed and/or secured relative to outer cannula (12) using any other suitable techniques (e.g., set screws, etc.). Furthermore, while needle hub (358) of the present example is formed of a plastic material, any other suitable material or combination of materials may be used.

Sleeve portion (360) of the present example comprises an annular projection (66), a plurality of flats (362), and a transverse opening (70), which is formed near the proximal end of sleeve portion (360). A pair of o-rings (72) are positioned such that one o-ring (72) is proximal to transverse opening (70) and another o-ring (72) is distal to transverse opening (70). As will be described in greater detail below, transverse opening (70) is in fluid communication with the interior defined by needle hub (60), as well as with vacuum lumen (40) of outer cannula (12). In the present example, another transverse opening (70) is formed through sleeve portion (360), also between o-rings (72), and opposite to the other transverse opening (70). Other suitable configurations for sleeve portion (360) will be apparent to those of ordinary skill in the art in view of the teachings herein.

Thumbwheel (62) of sleeve portion (360) is essentially the same as, and may be operated in a manner similar to, thumbwheel (62) of sleeve portion (64) of probe (102) described above. Thumbwheel (62) will therefore not be discussed in any greater detail here. Of course, thumbwheel (62) may alternatively be varied in any suitable way, as desired, if not omitted altogether, in the case of either probe (102, 103).

In the present example, an exposed gear (364) is slid onto sleeve portion (360). In particular, the interior of gear (364) is configured to mate with flats (362) of sleeve portion (360), such that gear (364) rotates unitarily with sleeve portion (360). With sleeve portion (360) being unitarily engaged with outer cannula (12), rotation of gear (364) will further cause rotation of cannula (12) for reorienting aperture (16).

Gear (364) is exposed through base member (356), and is further configured to engage with a complimentary exposed gear (not shown) of a holster (not shown). In particular, gear (364) is configured to mesh with a complimentary exposed gear such that the complimentary gear can impart rotation to gear (364), thereby rotating outer cannula (12). However, in the present example, gear (364) is not engaged with a complimentary gear when probe (103) is coupled with holster (302). It will therefore be appreciated that, like other components and features described herein, gear (364) and flats (362) may simply be omitted if desired.

C. Exemplary Needle Manifold

Figure 34:
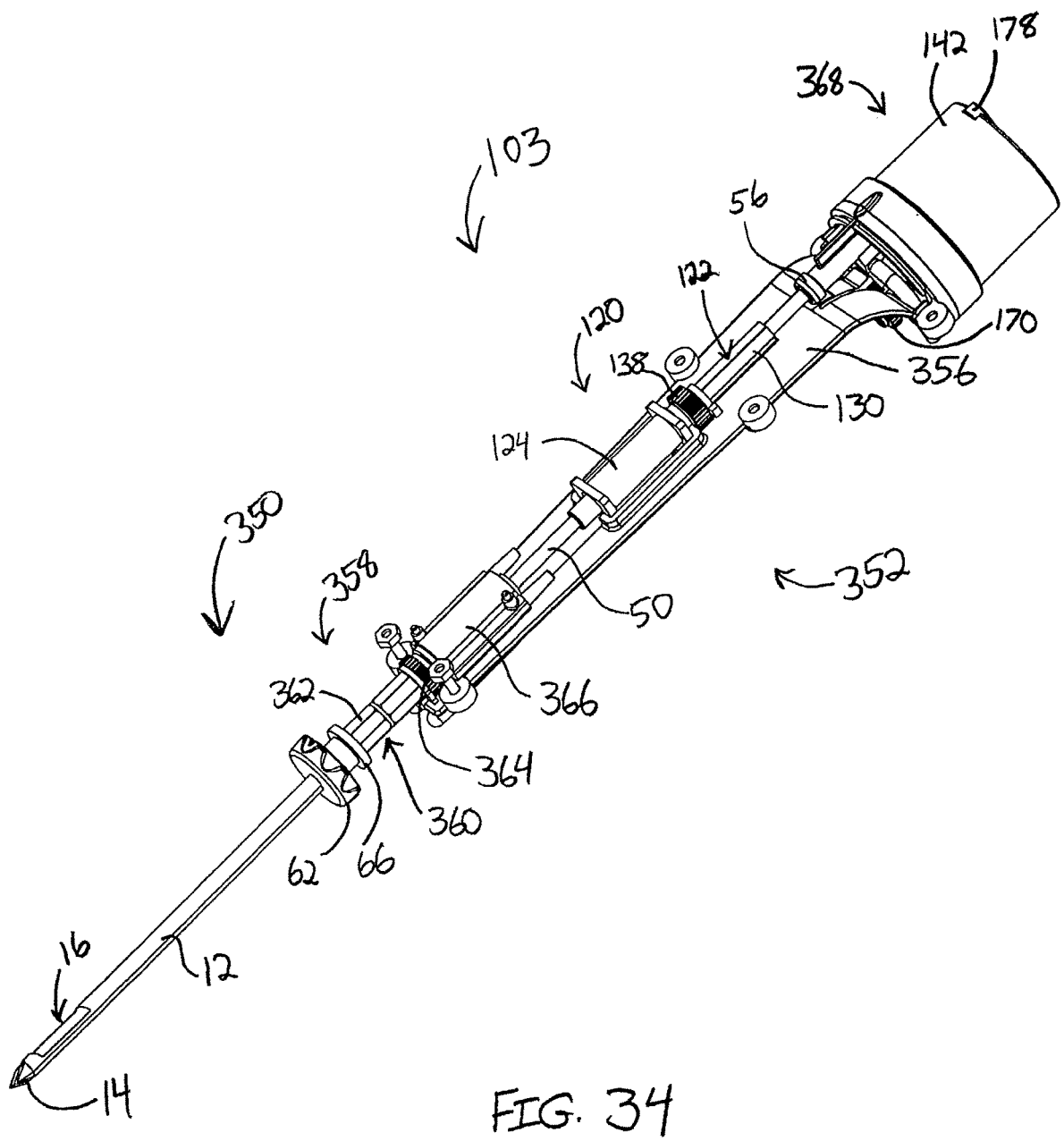
FIG. 34 depicts a top perspective view of the probe portion of FIG. 33, with a top cover removed.
Figure 35:
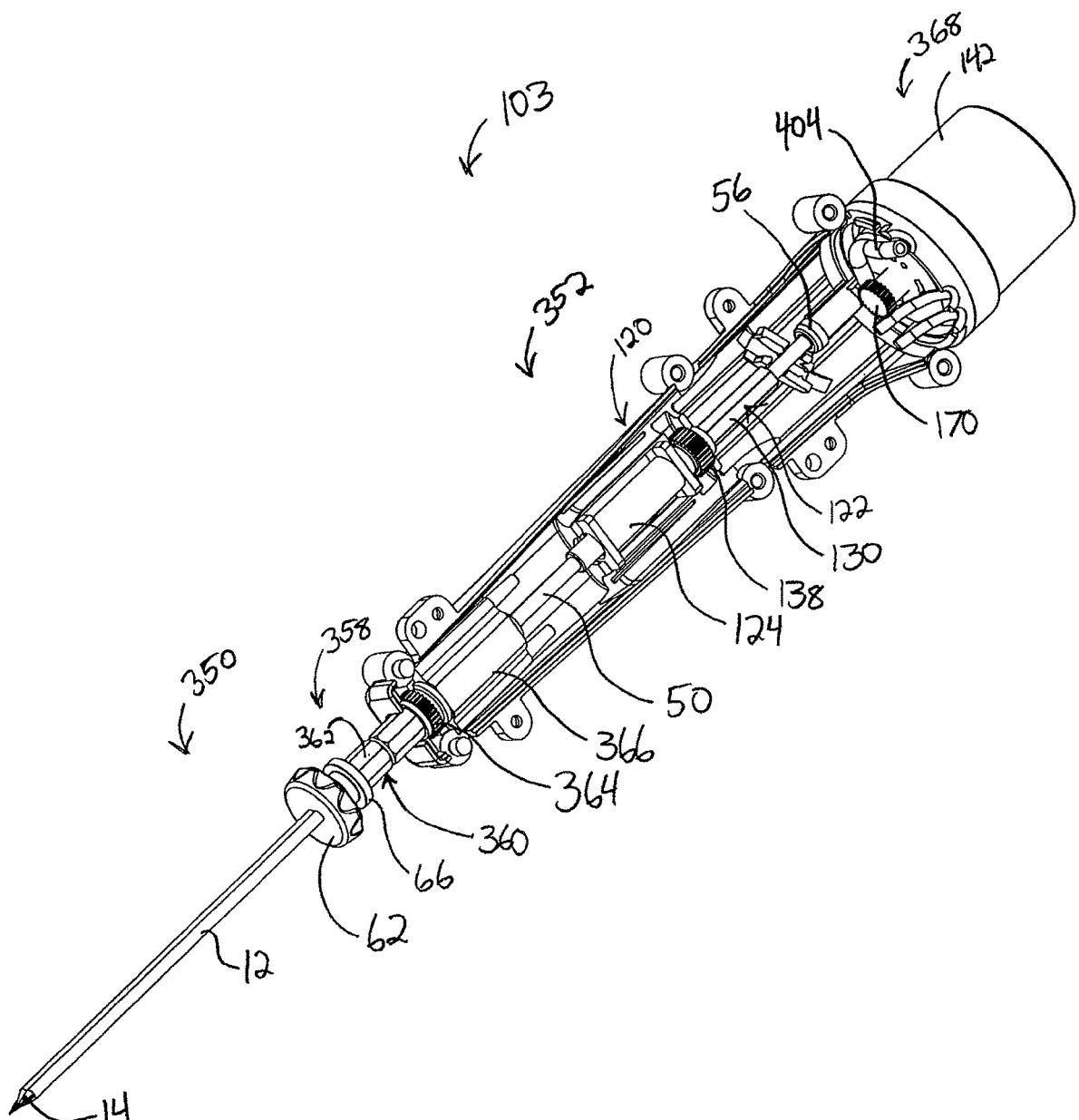
FIG. 35 depicts a bottom perspective view of the probe portion of FIG. 33, with a base removed.

As shown in FIGS. 34-36, a needle manifold (366) is provided about sleeve portion (360). Needle manifold (366) is fixed relative to base member (356) in this example. Needle manifold (366) is in fluid communication with tube (402), such that tube (402) may communicate saline, a vacuum, and/or pressurized air, etc., to needle manifold (366) as will be described in greater detail below. Needle manifold (366) is further in fluid communication with the interior of sleeve portion (360), via transverse openings (70), one of which is shown in FIG. 37. O-rings (64) are configured to maintain a fluid seal between needle manifold (366) and sleeve portion (360), even as sleeve portion (360) rotates relative to needle manifold (366). A seal (not shown) is may also provided at the proximal end of sleeve portion (360), at the interface between sleeve portion (360) and cutter (50). Needle manifold (366), sleeve portion (360), and outer cannula (12) are thus configured and arranged such that saline, a vacuum, and/or pressurized air, etc. that is communicated via tube (402) to needle manifold (366) will be communicated to vacuum lumen (40) via transverse openings (70). Of course, any other suitable structures or arrangements may be used to communicate saline, a vacuum, and/or pressurized air, etc. from tube (402) to vacuum lumen (40).

D. Exemplary Cutter Rotation and Translation Mechanism

In the present example, and as shown in FIGS. 34-35, body portion (350) of probe (103) comprises a cutter rotation and translation mechanism (120), which is operable to rotate and translate cutter (50) within outer cannula (12). Cutter rotation and translation mechanism (120) in this example has essentially the same components, features, and operability of the cutter rotation and translation mechanism (120) described above with respect to probe (102). Cutter rotation and translation mechanism (120) will therefore not be discussed in any greater detail here. Of course, cutter rotation and translation mechanism (120) may alternatively be varied in any suitable way, as desired, in the case of either probe (102, 103).

E. Exemplary "Sharps Reduction" Variation

In addition, needle portion (350) and cutter (50) of biopsy probe (103) may be configured to be removable from biopsy probe (103) in essentially the same manner as described above with respect to removability of needle portion (10) from biopsy probe (102). For instance, body portion (352) may include a feature similar to release tab (118), or any other suitable feature, to provide, permit, or facilitate removability of needle portion (350) and cutter (50) from body portion (352).

F. Exemplary Tissue Sample Holder Manifold

Figure 38:
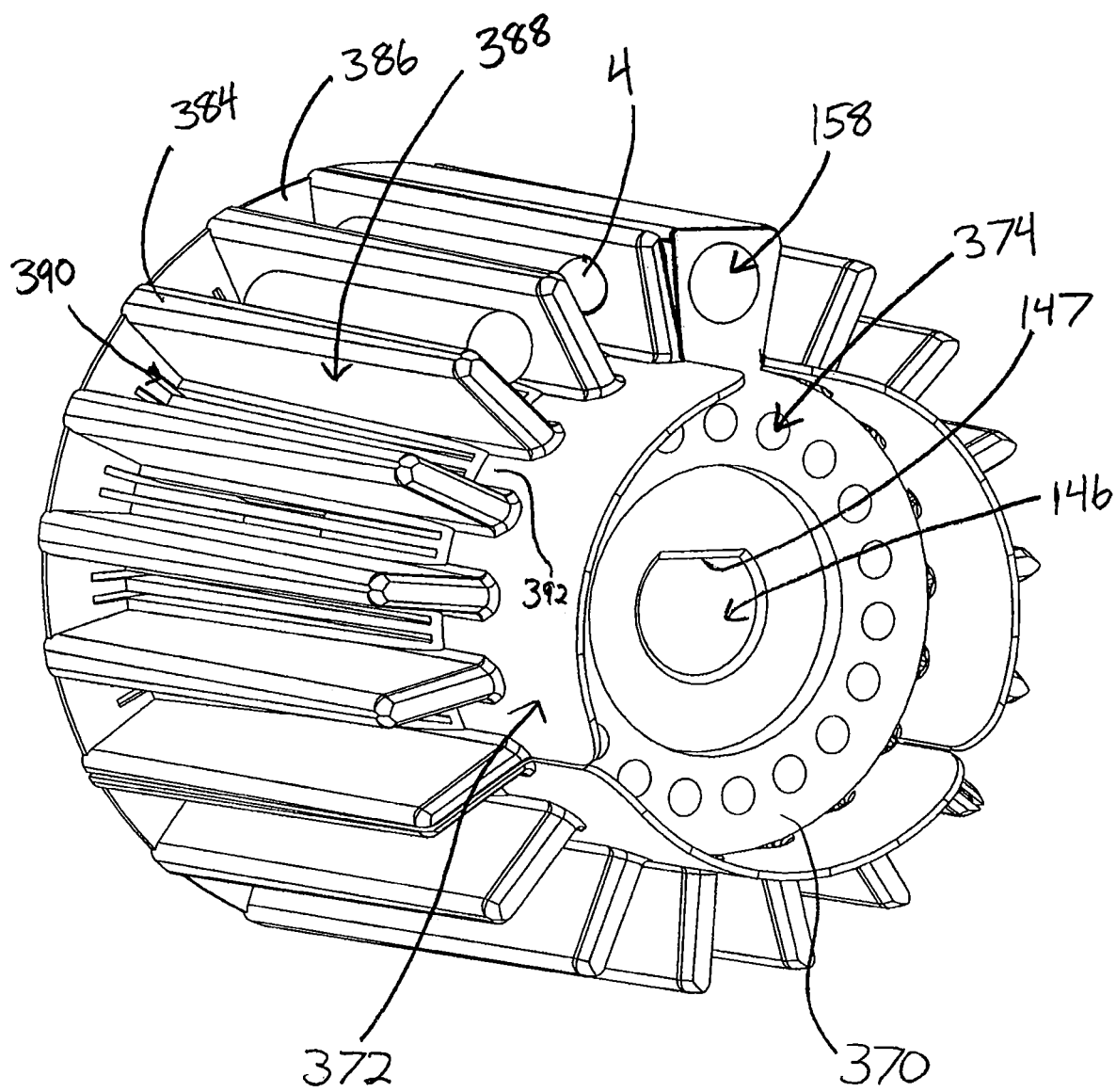
FIG. 38 depicts a front perspective view of an exemplary tissue sample holder, with a cup and other components removed.
Figure 39:
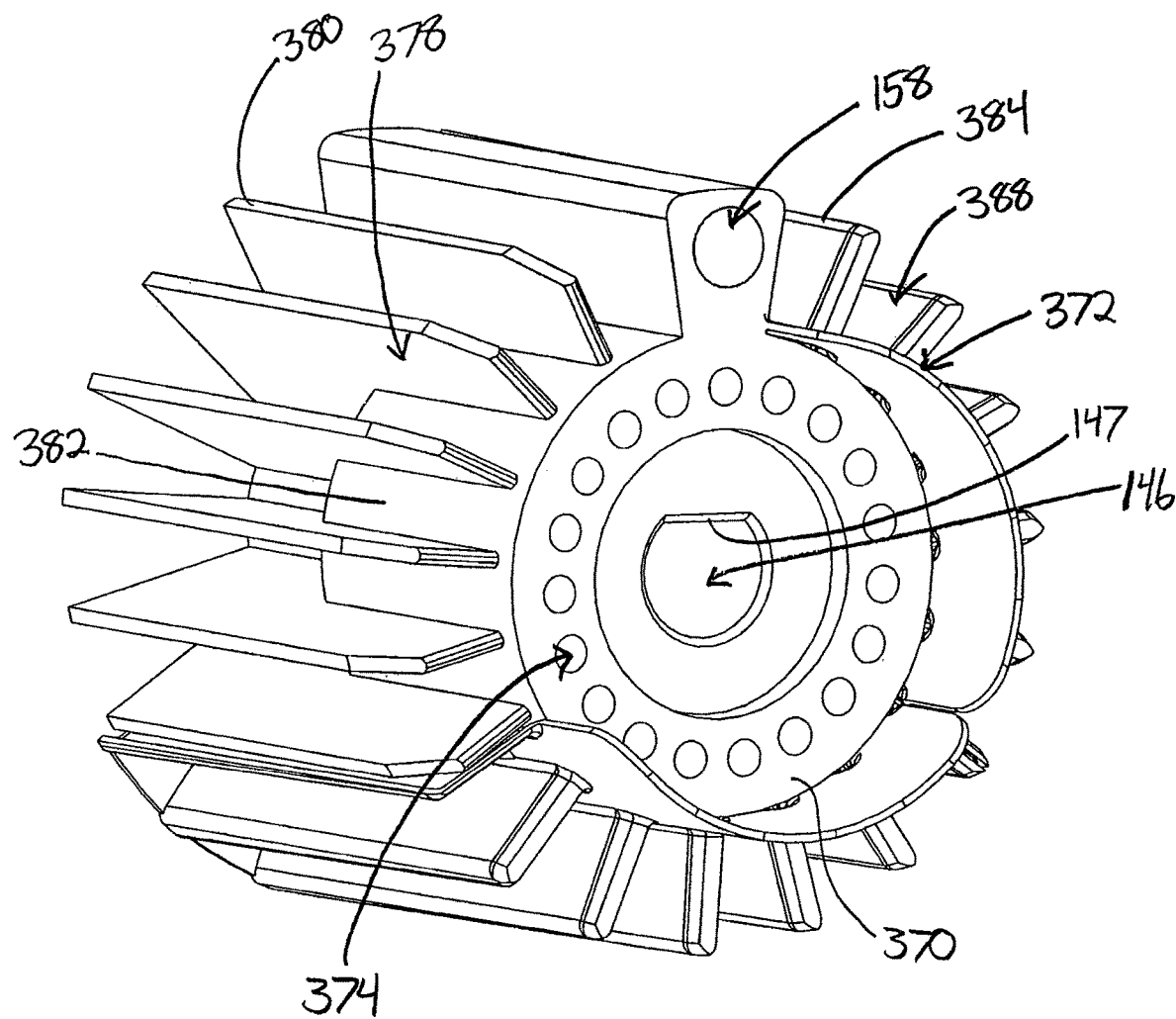
FIG. 39 depicts the tissue sample holder of FIG. 38, with a tissue sample tray removed.
Figure 40:
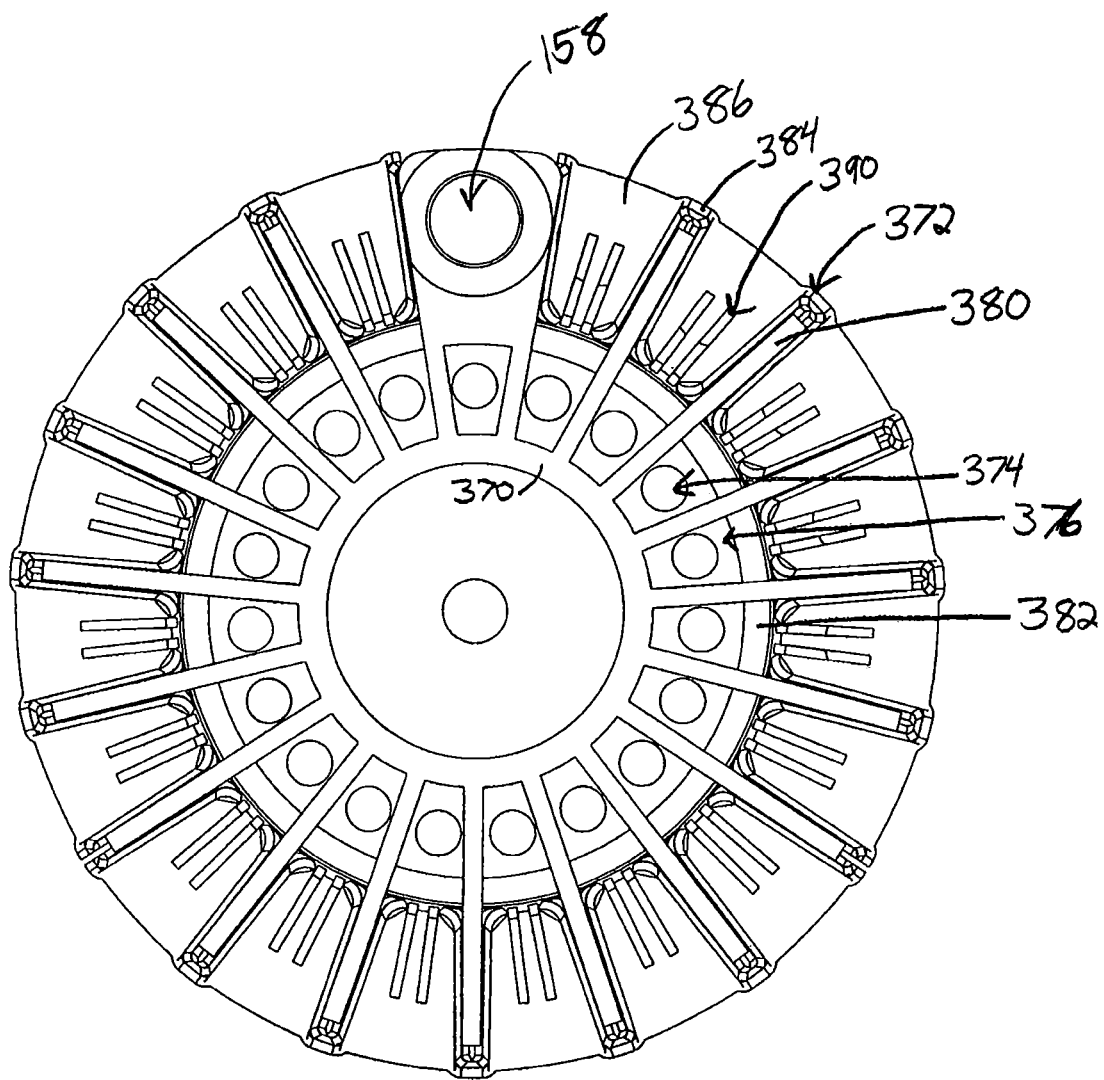
FIG. 40 depicts a rear view of the tissue sample holder of FIG. 38, with a cup and other components removed.

As shown in FIGS. 38-40, a tissue sample holder (368) is provided at the end of body portion (352) of probe (103). Tissue sample holder (368) comprises a cup (142), a manifold (370), and a plurality of trays (372). Manifold (370) includes a central recess (146), a plurality of openings (374), and a longitudinally extending sidewall (382). Sidewall (382) only extends for a portion of the length of manifold (370) in this example, though sidewall (382) may alternatively extend to any other degree as desired. Manifold (370) also includes a plurality of radially extending walls (380). Walls (380) and the interior surface of sidewall (382) define a plurality of longitudinal passages (376). Each longitudinal passage (376) is in fluid communication with a corresponding opening (374).

In addition, walls (380) and the exterior surface of sidewall (382) define a plurality of chambers (378). With sidewall (382) providing clearance (e.g., by not extending the full length of manifold (370)), each chamber (378) is in fluid communication with a corresponding longitudinal passage (376). Manifold (370) is thus configured such that each opening (374) is in fluid communication with a corresponding chamber (378). Of course, any other suitable structures or configurations for manifold (370) may be used. For instance, manifold (144) described above with respect to biopsy probe (102) may be used with biopsy probe (103) in lieu of manifold (370) being used with biopsy probe (103). Likewise, manifold (370) may be used with biopsy probe (102) in lieu of manifold (144) being used with biopsy probe (102).

G. Exemplary Tissue Sample Trays

Trays (372) of the present example are configured to be placed on manifold (370), and to receive tissue samples (4) as will be described in greater detail below. Each tray (372) has a plurality of base portions (382), a plurality of hollow wall portions (384), and a plurality of webs (386). Base portions (392), hollow wall portions (384), and webs (386) define chambers (388). By way of example only, each chamber (388) may be configured to receive a single tissue sample (4) captured by cutter (50). Alternatively, chambers (388) may be configured such that each chamber (388) may hold more than one tissue sample (4). As shown, the underside of each hollow wall portion (384) is configured to receive a wall (380) of manifold (370). As is also shown, each hollow wall portion (384) has a generally tapered configuration, though any other suitable configuration may be used.

In addition, trays (372) have a plurality of openings (390), extending longitudinally, formed through the base portion (392) within each chamber (388). Openings (390) continue, extending radially outwardly, through a portion of each web (386). Accordingly, with sidewall (382) not extending the full length of manifold (370), the openings (390) permit fluid communication between each longitudinal passage (376) and each corresponding chamber (388). In other words, each opening (374) is in fluid communication with a corresponding chamber (388).

Each tray (372) may further comprise one or more types of markings or other indicia to distinguish one chamber (388) from another chamber (388). Such markings or indicia may be similar to the same described above with respect to chambers (166) of trays (160). Accordingly, discussion of such markings or indicia will not be repeated here. Similarly, cup (142) of tissue sample holder (368) is essentially the same as cup (142) of tissue sample holder (140) described above. Discussion of cup (142) will therefore not be repeated here.

H. Exemplary Rotation and Alignment of Manifold

Manifold (370) of the present example is configured to rotate relative to base member (356), as will be described in greater detail below. Manifold (370) of the present example is further configured such that each opening (374) may be selectively aligned with a port (not shown) that is in fluid communication with tube (404). Such alignment of an opening (374) and such a port will place the aligned opening (374) in fluid communication with tube (404), such that induction of a vacuum within tube (404) will effect induction of a vacuum through opening (374), as well as within the chamber (388) associated with that opening (374). In addition, manifold (370) and trays (372) of the present example are configured such that each chamber (388) may be selectively placed in fluid communication with cutter lumen (52). It will therefore be appreciated that a vacuum in tube (406) may induce a vacuum in cutter lumen (52), with the vacuum being communicated via the above-noted port, an associated opening (374), an associated longitudinal passage (376), and an associated chamber (388). Of course, there are a variety of other ways in which a vacuum may be induced within a cutter lumen (52), and any other suitable structures or techniques may be used. Furthermore, pressurized air, a liquid (e.g., saline), or any other fluid may be communicated through the above-mentioned components in lieu of or in addition to a vacuum being induced therein.

A gear (170) is engaged with manifold (370) of the present example. In particular, gear (170) is inserted within central recess (146) of manifold (370). Gear (170) and central recess (146) of manifold (370) are essentially the same in configuration and in operation as gear (170) and central recess (146) described above with respect to manifold (144). For instance, gear (170) is configured to mesh with a complimentary gear (210) of holster (302), such that gear (210) may be used to impart rotation to gear (170). Such rotation may be used to selectively (e.g., consecutively) align chambers (388) with cutter lumen (52), to successively collect a discrete tissue sample (4) in each chamber (388) during use of biopsy device (101). Furthermore, such collection of tissue samples (4) may be performed without having to withdraw and re-insert needle portion (350) relative to patient during such a process.

I. Exemplary "Parking Pawl"

Body portion (352) of the present example further comprises a pawl portion (182) having teeth (not shown). Pawl portion (182) is resiliently urged for the teeth to engage with gear (170). Pawl portion (182) in this context is thus essentially the same in configuration and operability as pawl portion (182) discussed above in the context of engagement member (180) of probe (102). Accordingly, the similar details on configuration, function, operability, etc. will not be repeated here. However, it should be noted that in the present example, pawl portion (182) is integral with the remainder of base member (356), rather than being provided as part of a separate engagement member (180). Of course, body portion (352) may be modified such that pawl portion (182) is provided as part of a separate piece that is secured relative to base member (356). Similarly, base member (116) of probe (102) may be modified such that pawl portion (182) is formed as an integral piece of base member (116), in lieu of being part of a separate engagement member (180) that is secured relative to base member (116). Still other variations will be apparent to those of ordinary skill in the art in view of the teachings herein. In addition, it will be appreciated that a biopsy device (101) may lack a pawl portion (182) altogether, such that a manifold (370) may freely rotate when biopsy probe (103) is not coupled with a holster (302).

J. Exemplary Dedicated Chamber

As shown in FIGS. 38-40, tissue sample holder (368) of the present example has a passage (158) formed through manifold (370). Passage (158) of manifold (370) is essentially the same in configuration, function, operability, etc. as passage (158) of manifold (144) described above. Details of passage (158) will therefore not be repeated here. However, it will be noted that, like passage (158) of manifold (144), passage (158) of manifold (370) may be used to pass instruments such as biopsy site marker deployment devices, an applier (90), and/or other devices or liquids, etc., into and/or through cutter lumen (52). Similarly, biopsy probe (103) may be initially provided with passage (158) being aligned with cutter lumen (52) by default.

Cup (142) of tissue sample holder (368) further comprises an opening (176) and a hatch (178). Cup (142), opening (176), and hatch (178) of tissue sample holder (368) are essentially the same in configuration, function, operability, etc. as cup (142), opening (176), and hatch (178) of tissue sample holder (140). Accordingly, details of cup (142), opening (176), and hatch (178) will not be repeated here.

IV. Exemplary Holster for Ultrasound Use

As shown in FIGS. 41-45, an alternative holster (302) comprises a top housing member (304), through which a portion of each of gears (208, 210) is exposed, and a bottom housing member (306). Boss (212) is provided on top housing member (304), and is configured to disengage pawl portion (182) from gear (170) when biopsy probe (103) is coupled with holster (302). A plurality of hook members (305) extend from top housing member (304) for selectively securing probe (103) to holster (302), though other structures or techniques may be used. Holster (302) of this example further comprises a cutter drive mechanism (310) and a tissue holder rotation mechanism (320). Each of these merely exemplary components will be described in greater detail below. Holster (302) of the present example is configured to be coupled with a biopsy probe (103), such as biopsy probe (103) described above, to provide a biopsy device (101). In addition, holster (302) is configured to be handheld, such that biopsy device (101) may be manipulated and operated by a single hand of a user (e.g., using ultrasound guidance, etc.). However, it will be appreciated in view of the disclosure herein that holster (302) may be used in a variety of other settings and combinations. By way of example only, holster (302) may alternatively be coupled with biopsy probe (102) instead of biopsy probe (103). As another merely illustrative example, holster (302) may be coupled with a variation of biopsy probe (102) that has a modified needle hub (60) (e.g., a needle hub (60) that is shorter, not configured for firing needle portion (10), etc.)

A. Exemplary Cutter Drive Mechanism

Figure 44:
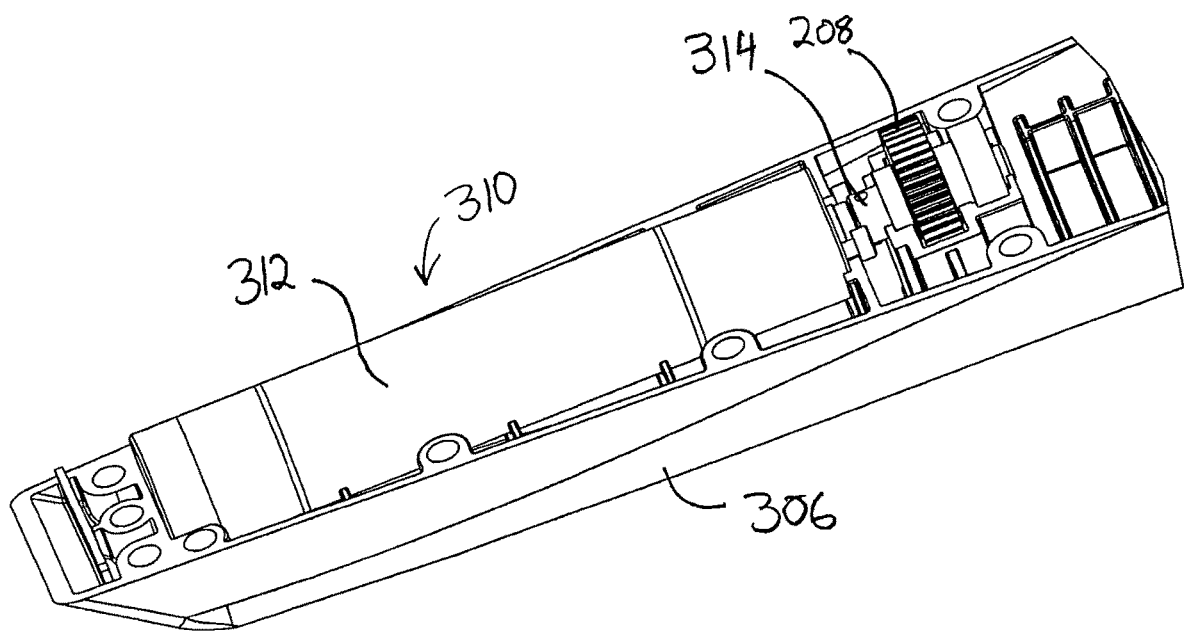
FIG. 44 depicts a partial view of the holster of FIG. 41, showing an exemplary cutter drive mechanism.

As shown in FIG. 44, cutter drive mechanism (310) of the present example comprises a motor (312) with a shaft (314) extending therefrom. Gear (208) is mounted to shaft (314), and is configured to rotate unitarily therewith. As noted above, a portion of gear (208) is exposed through top housing member (304), such that gear (208) meshes with gear (138) of cutter rotation and translation mechanism (120) when biopsy probe (103) is coupled with holster (302). Accordingly, when motor (312) is activated to rotate, such rotation may be communicated via shaft (314) and gears (208, 138), to effect simultaneous rotation and translation of cutter (50) as described above. Other ways in which a cutter drive mechanism (310) may be configured or operated will be apparent to those of ordinary skill in the art in view of the teachings herein.

B. Exemplary Tissue Holder Rotation Mechanism

Figure 45:
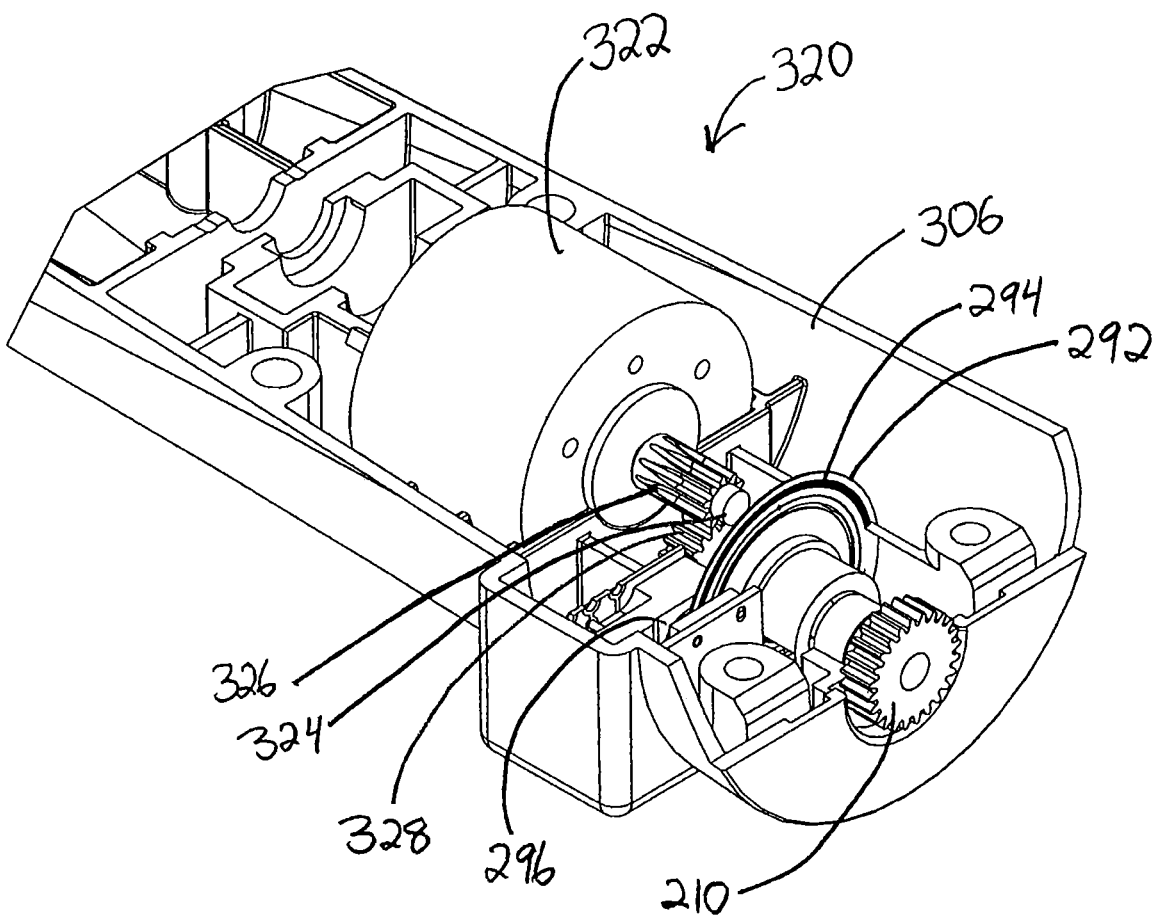
FIG. 45 depicts a partial view of the holster of FIG. 41, showing an exemplary tissue holder rotation mechanism.

As shown in FIG. 45, tissue holder rotation mechanism (320) of the present example comprises a motor (322) having a shaft (324) with a gear (326) mounted thereto, such that gear (326) rotates unitarily with shaft (324). Gear (326) is configured to mesh with gear (328), which is mounted to shaft (330). Gear (210), which has been noted above, is also mounted to shaft (330), at the proximal end of shaft (330).

In particular, gear (210) is configured to mesh with gear (170) of tissue sample holder (368) when biopsy probe (103) is coupled with holster (302). Accordingly, when motor (322) is activated to rotate, such rotation may be communicated via shafts (324, 330) and gears (326, 328, 210, 170), to effect rotation of manifold (370) as described above.

In addition, an encoder wheel (292) is coupled with shaft (330), and is configured to rotate unitarily therewith. Encoder wheel (292) has a plurality of slots (294) formed therethrough, similar to slots (294) noted above. A sensor (296) is positioned adjacent to encoder wheel (292). In particular, sensor (296) is positioned such that slots (294) successively pass before sensor (296) as encoder wheel (292) rotates with shaft (290). Sensor (296) may therefore be used to count the passage of slots (294), which may be translated into rotational position of manifold (366). In other words, since encoder wheel (292) and manifold (366) rotate concomitantly when biopsy probe (103) is coupled with holster (302) in the present example, the passage of slots (294) past sensor (296) during rotation of shaft (330) may be indicative of manifold (366) rotation, and therefore of manifold (366) position. It will be appreciated that such information may be further indicative of which particular chamber (388) is aligned with cutter lumen (52). Suitable uses for such information will be apparent to those of ordinary skill in the art in view of the teachings herein. Suitable devices that may be used for sensor (296) will also be apparent to those of ordinary skill in the art in view of the teachings herein. Furthermore, other ways in which a tissue holder rotation mechanism (320) may be configured or operated will be apparent to those of ordinary skill in the art in view of the teachings herein.

C. Exemplary Illumination Features

Figure 41:
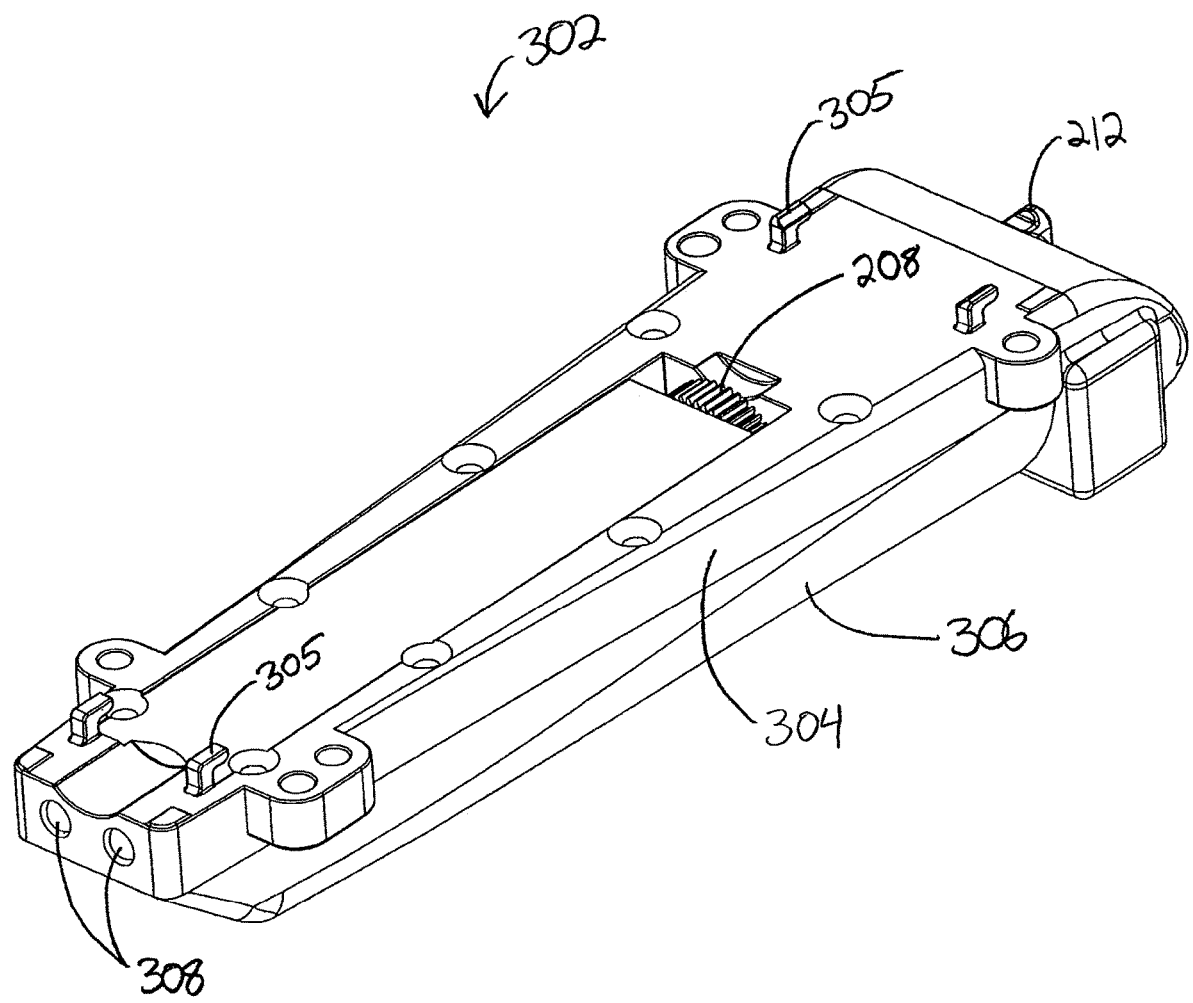
FIG. 41 depicts a front perspective view of a holster of the biopsy device of FIG. 4.
Figure 42:
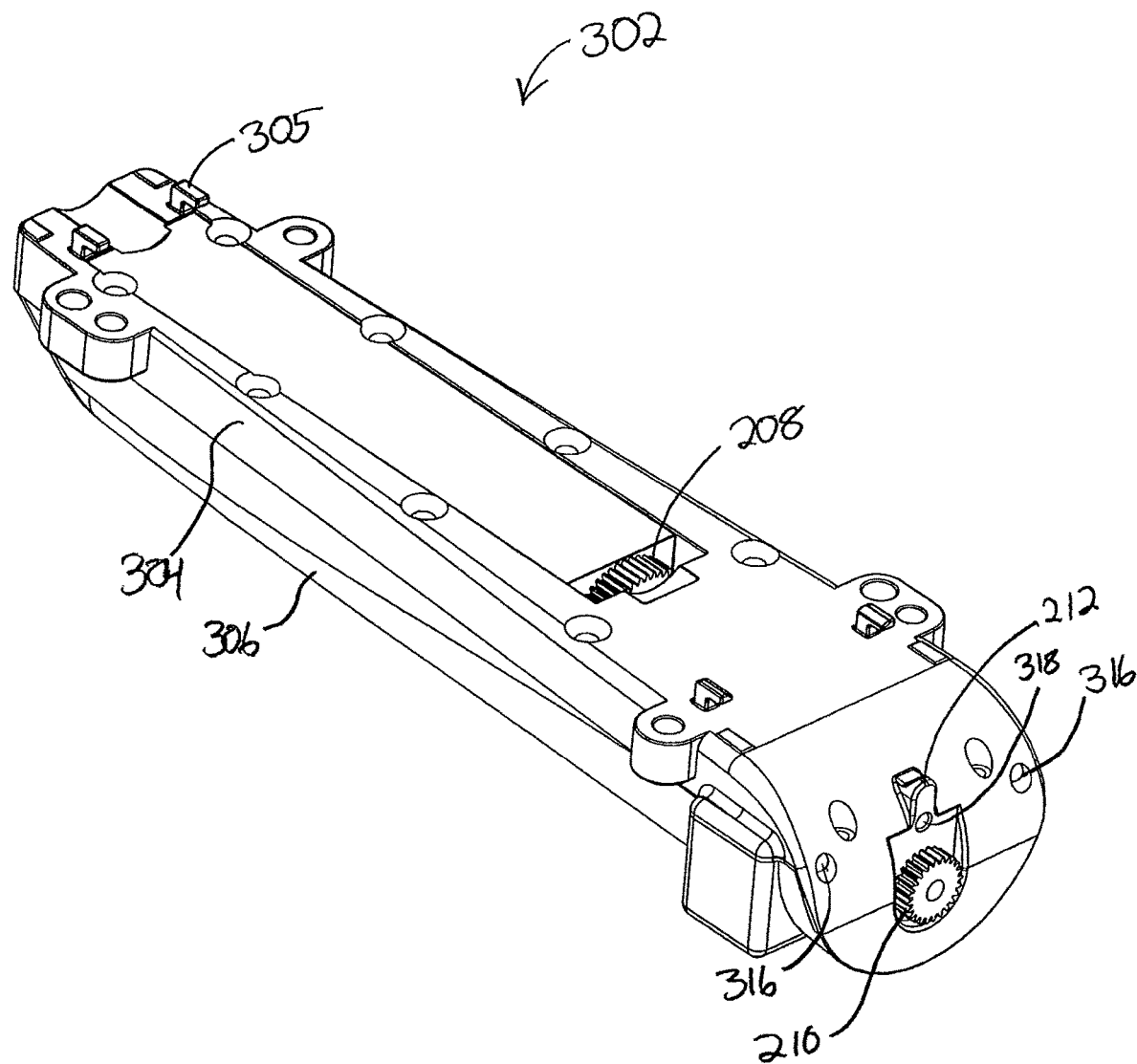
FIG. 42 depicts a rear perspective view of the holster of FIG. 41.
Figure 43:
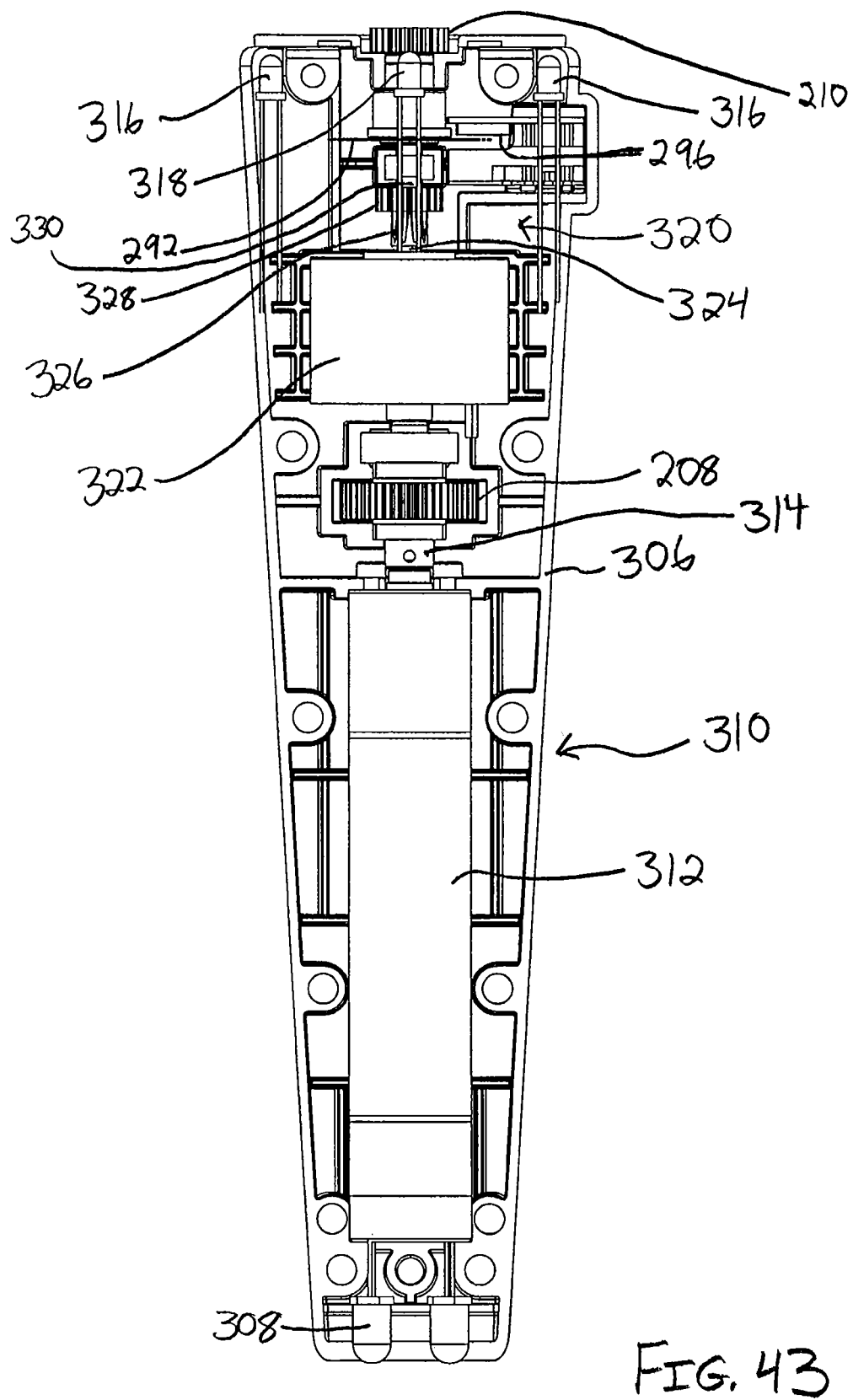
FIG. 43 depicts a top view of the holster of FIG. 41, with a top cover removed.

As shown in FIGS. 41-43, holster (302) of the present example further includes a plurality of LEDs (308, 316, 318). In particular, a pair of LEDs (308) are provided on the distal end of holster (302). The light emitted by LEDs (308) is viewable through openings formed in the distal end of top housing member (304). LEDs (308) are positioned and configured to act as "headlights" for biopsy device (101), such as by illuminating a site of a patient where needle portion (350) is to be inserted. LEDs (308) may be continuously activated, such as being activated while biopsy device (101) is activated. Alternatively, LEDs (308) may be selectively activated, such as by a switch (not shown) on holster (302), on probe (103), on vacuum control module (400), or otherwise. Other ways in which LEDs (308) may be activated, positioned, or otherwise operated or configured will be apparent to those of ordinary skill in the art in view of the teachings herein.

LEDs (316, 318) are provided on the proximal end of holster (302). The light emitted by LEDs (316, 318) is viewable through openings formed in the distal end of bottom housing member (306). As shown, LEDs (316) are each positioned on either side of LED (318), which is positioned between gear (210) and boss (212). LEDs (316) are configured to provide illumination of tissue sample holder (368). In particular, manifold (370) and other components are configured to permit illumination of tissue sample holder (368) by LEDs (316, 318) in this example. For instance, manifold (370), gear (170), shaft (172), and/or other components may be formed of a substantially transparent or substantially translucent material, including combinations of materials providing a combination of transparent and/or translucent properties. Cup (142) may also be substantially transparent or substantially translucent to permit a user to see at least some amount of light emitted by LEDs (316, 318). Suitable selections and arrangements of materials and components for permitting illumination of tissue sample holder (368) by LEDs (316, 318) will be apparent to those of ordinary skill in the art in view of the teachings herein.

It will also be appreciated that one or more of LEDs (316, 318) may be positioned to illuminate a particular chamber (388) within tissue sample holder (368), rather than illuminating the entire tissue sample holder (368). For instance, LEDs (316, 318) may be configured to illuminate an active chamber (388), such as the chamber (388) located in the nine o'clock, twelve o'clock, and/or three o'clock position. Furthermore, one or more of LEDs (308, 316, 318) may be configured to flash or change color to indicate an error condition (e.g., blocked cutter lumen (52), probe (103) insufficiently coupled with holster (302), leakage in a tube (402, 404, 408, 410), etc.). Other ways in which LEDs (316, 318) may be activated, positioned, or otherwise operated or configured will be apparent to those of ordinary skill in the art in view of the teachings herein.

It will also be appreciated that holster (202) may be modified to include any of LEDs (308, 316, 318). Similarly, manifold (144) and/or other components of probe (102) may be configured to permit manifold (144) to be illuminated by LEDs (316, 318); and cup (142) may be configured to permit a viewer to observe illumination of manifold (144) in biopsy device (100). Alternatively, any or all of LEDs (308, 316, 318) may simply be omitted from biopsy device (100, 101) altogether.

While LEDs (308, 316, 318) have been described in the present example as providing illumination, any other suitable source of light may be used, including but not limited to an incandescent bulb. Alternatively, a biopsy device (100, 101) may lack a source of light altogether.

V. Exemplary Vacuum Control Module and Canister

Figure 46:
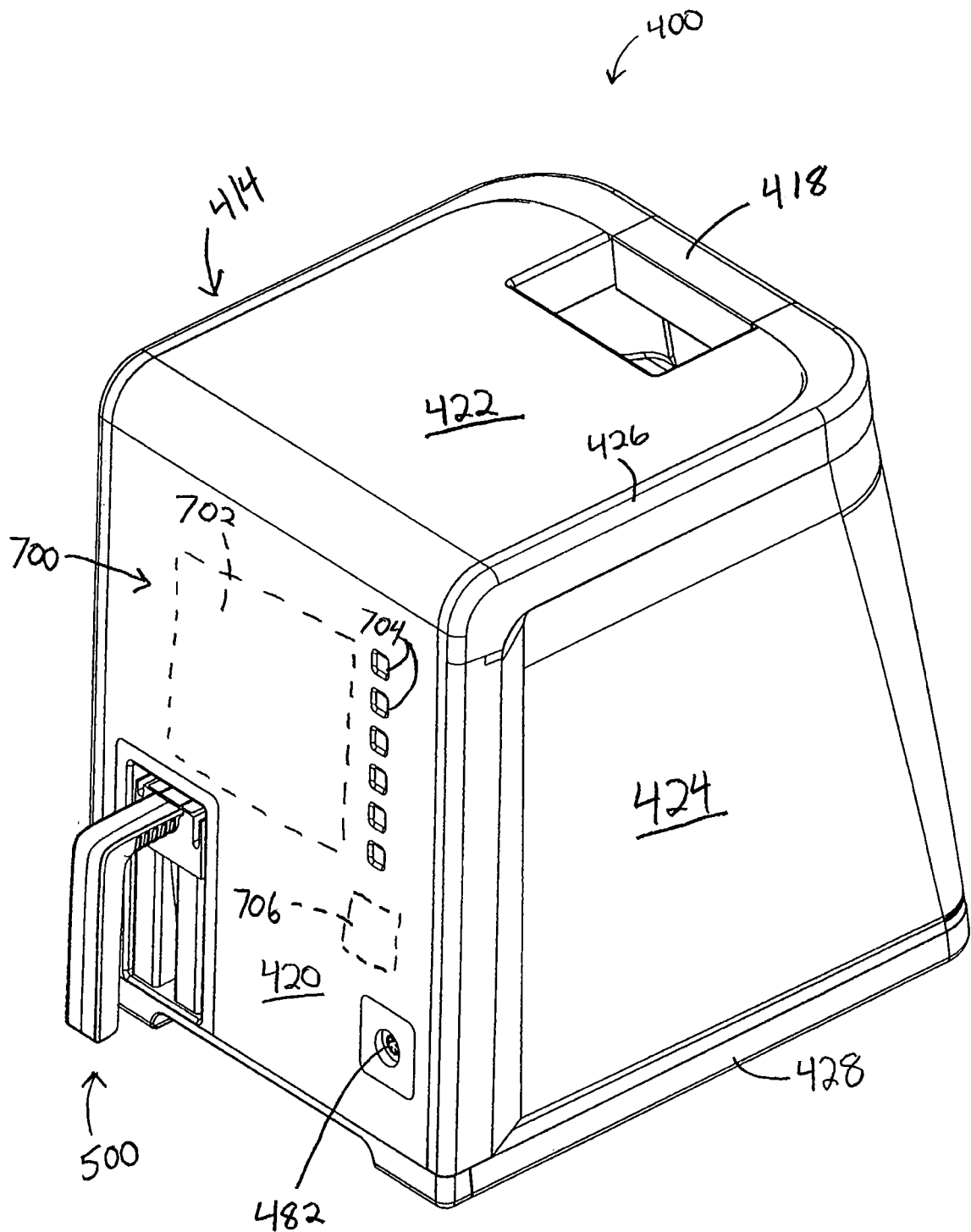
FIG. 46 depicts a perspective view of an exemplary vacuum control module and exemplary vacuum canister.
Figure 47:
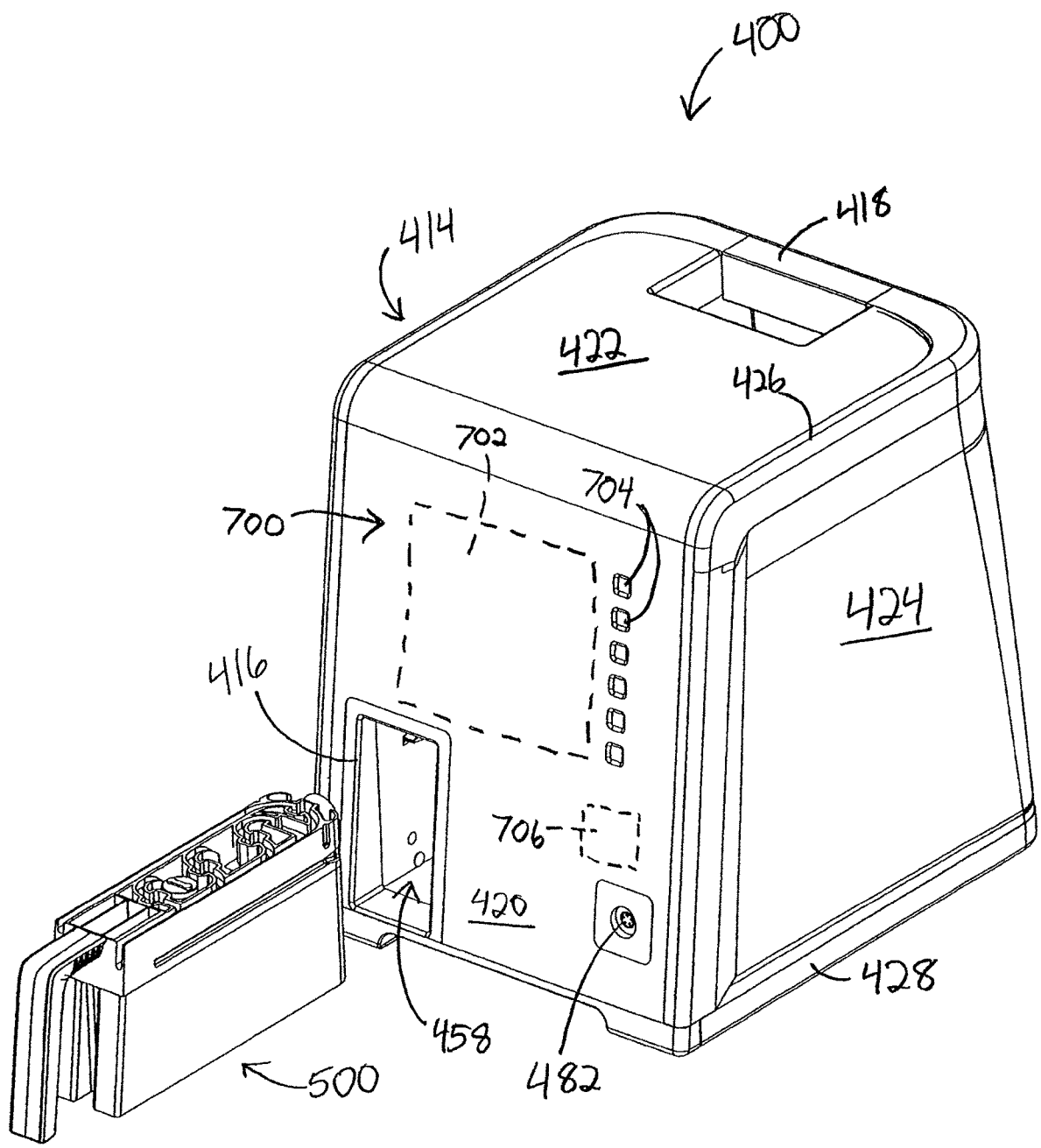
FIG. 47 depicts the vacuum control module of FIG. 46 with the vacuum canister of FIG. 46 separated therefrom.
Figure 48:
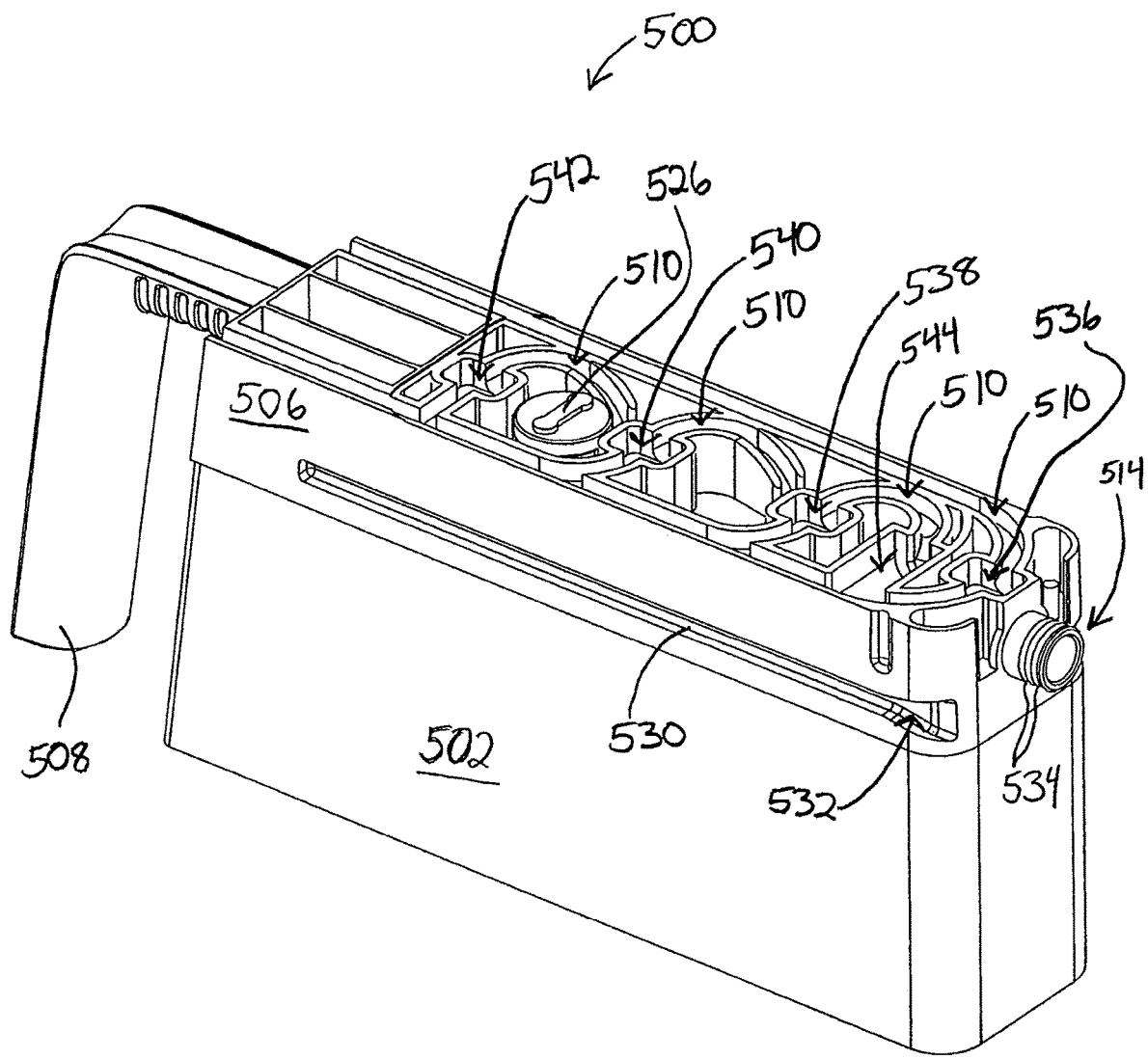
FIG. 48 depicts a perspective view of the vacuum canister of FIG. 46.
Figure 49:
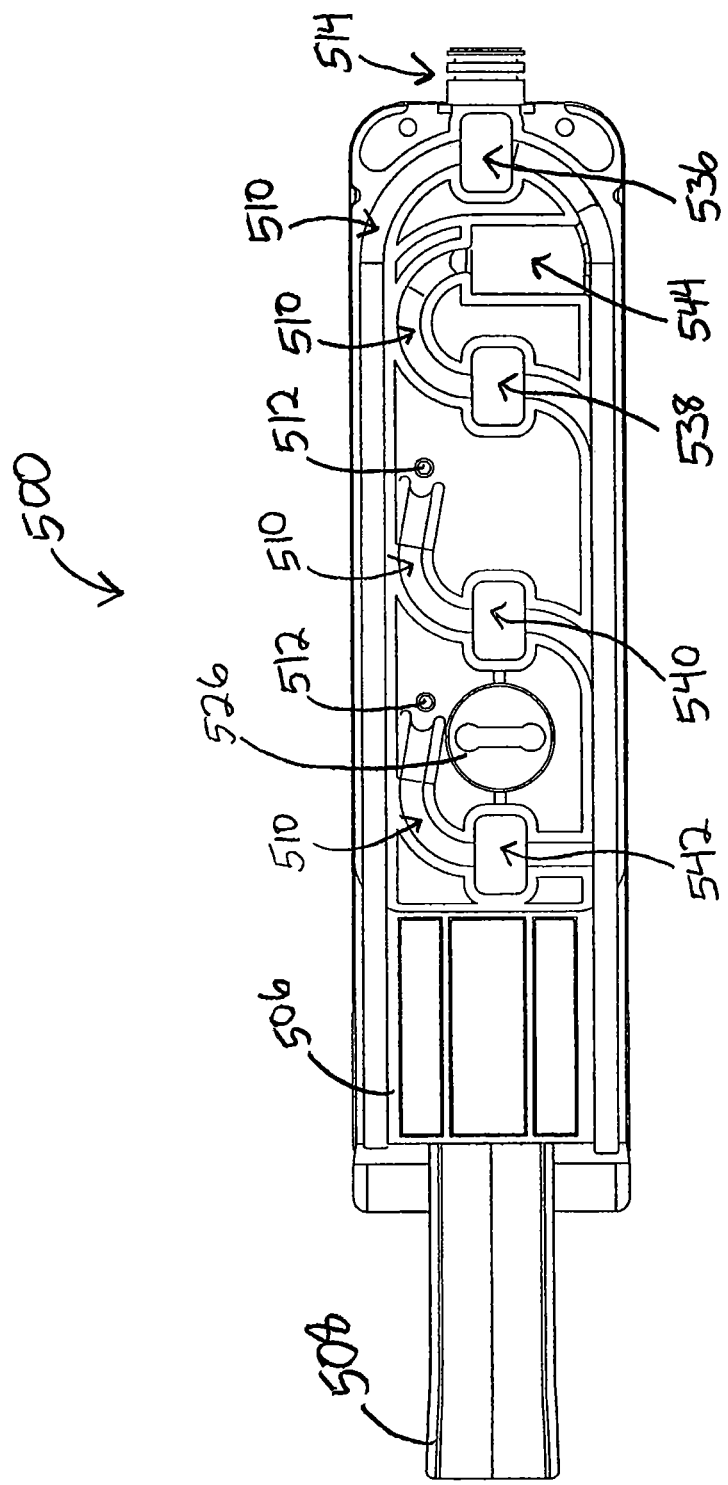
FIG. 49 depicts a top view of the vacuum canister of FIG. 46.

FIGS. 46-47 show an exemplary vacuum control module (400) and an exemplary vacuum canister (500). As shown, vacuum canister (500) is configured to be inserted into vacuum control module (400). As will be described in greater detail below, vacuum control module (400) is operable to induce a vacuum through vacuum canister (500), and such a vacuum may be communicated to biopsy probe (102, 103) as described above. Furthermore, vacuum canister (500) is operable to collect fluids that are communicated from biopsy probe (102, 103) during use of biopsy probe (102, 103). Vacuum canister (500) may thus be regarded as providing a fluid interface between biopsy probe (102, 103) and vacuum control module (400).

A. Exemplary Vacuum Canister

As shown in FIGS. 48-51, vacuum canister (500) comprises a base portion (502), a lid portion (506), and a handle (508). Handle (508) is configured to be gripped by a user when user inserts vacuum canister (500) into vacuum control module (400) or withdraws vacuum canister (500) from vacuum control module (400), as will be described in greater detail below. Base portion (502) is substantially hollow, and is configured to provide a reservoir (504) for collection of fluids (e.g., saline, blood, etc.) communicated from biopsy probe (102, 103).

Lid portion (506) of the present example has tracks (530) formed in its sides. Tracks (530) are configured to engage with rails (460) in the canister compartment (458) of vacuum control module (400), as will be described in greater detail below. Tracks (530) each have a flared portion (532) to provide guidance for tracks (530) to engage rails (460), to thereby facilitate insertion of vacuum canister (500) into canister compartment (458) of vacuum control module (400). In other embodiments, tracks (530) are provided on base portion (502). Alternatively, tracks (530) may be substituted or supplemented with any other suitable structures in any other suitable location(s), or may be simply omitted altogether.

In the present example, lid portion (506) has a plurality of trenches (510) formed therein. As will be described below, trenches (510) are configured to receive tubes (402, 404, 408, 410). A plurality of top ports (512) are formed on lid portion (506), and each top port (512) is configured have one of tubes (402, 404) coupled therewith. In particular, each top port (512) is configured to provide a path for fluid communication from a connected tube (402, 404) to the reservoir (504) defined by base portion (502). Lid portion (506) further comprises a vacuum port (514), which is configured to be placed in fluid communication with a vacuum source (412) in vacuum control module (400), as will be described in greater detail below. Vacuum port (514) includes a pair of o-rings (534) configured to provide a seal when engaged with a complimentary vacuum port (462) as will be described in greater detail below. It will be appreciated in view of the teachings herein that, when vacuum source (412) is used to generate a vacuum, such a vacuum may be communicated to tubes (402, 404) via vacuum port (514), reservoir (504), and top ports (512). The vacuum may be further communicated to biopsy probe (102, 103) via tubes (402, 404). Lid portion (506) also includes a vent recess (544), configured for venting the open end of a vent tube (410) into. Such venting will be described in greater detail below.

Lid portion (506) also has a cap (526) that is removably secured to an access port (528). Cap (526) is configured to provide a seal of access port (528) during use of biopsy system (2). After biopsy system (2) has been used, and liquid is present in reservoir (504), cap (526) may be removed to gain access to reservoir (504). Of course, like other components mentioned herein, cap (526) and access port (528) are merely optional, and may be varied, substituted, supplemented, or simply omitted altogether as desired.

Figure 51:
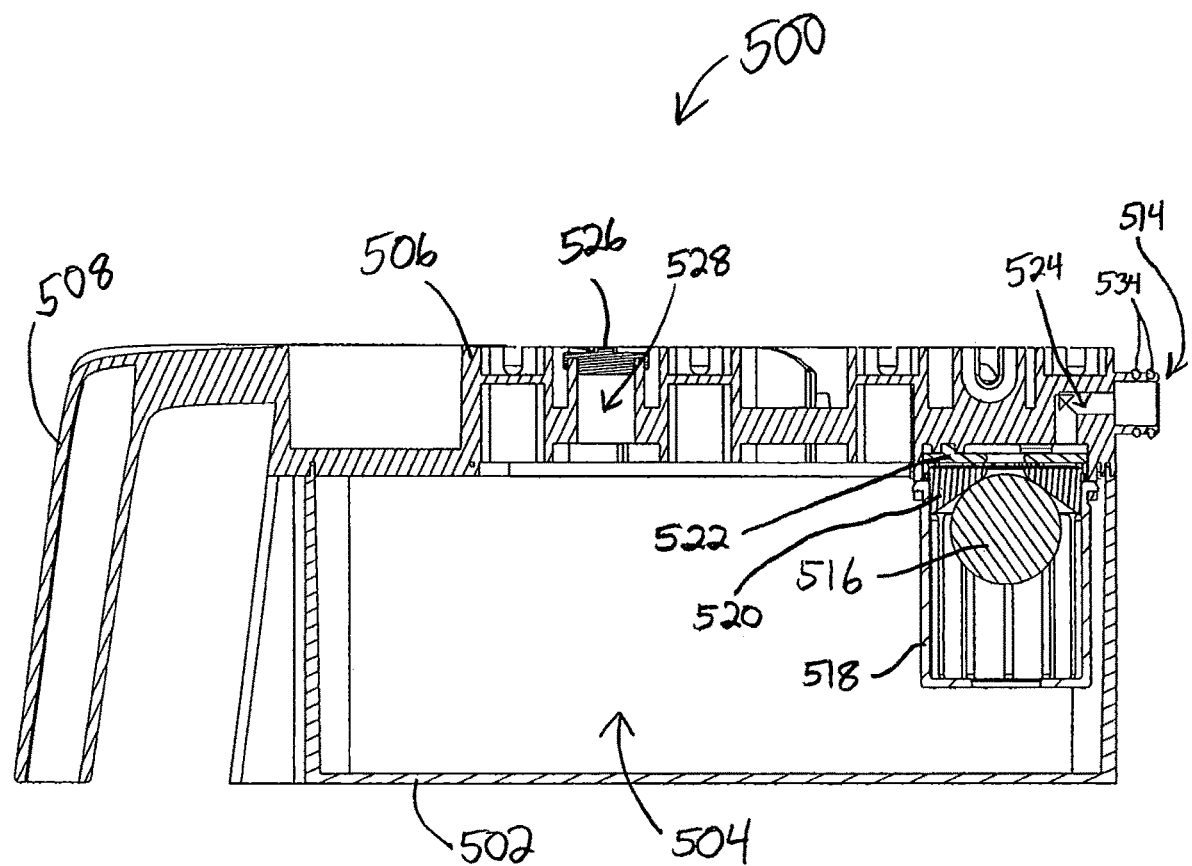
FIG. 51 depicts a cross-sectional view of the canister of FIG. 46, taken along a longitudinal plane.
Figure 52:
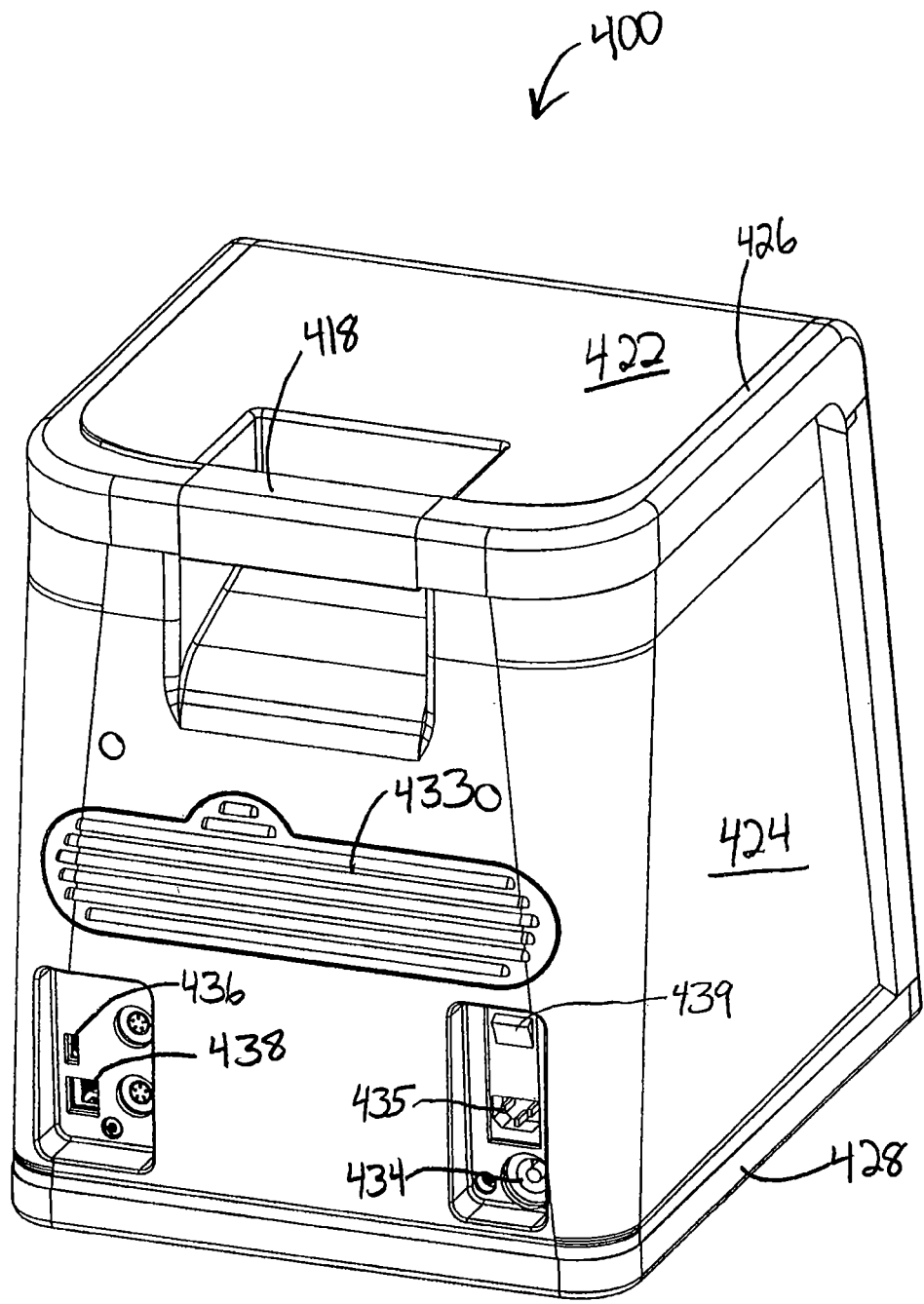
FIG. 52 depicts a rear perspective view of the vacuum control module of FIG. 46.

As best seen in FIG. 51, a float (516) is provided in a cage (518), which extends from the bottom of lid portion (506) into reservoir (504). While float (516) is shown as having a spherical shape, any other suitable shape may be used. An elastomeric funnel member (520) is partially disposed in and engaged with cage (518). In addition, a hydrophobic filter (522) is provided between the bottom of lid portion (506) and funnel member (520). A conduit (524) is formed in lid portion (506), providing fluid communication from vacuum port (514) to filter (522) and funnel member (520), and therefore, to reservoir (504). Filter (522) is configured to prevent communication of liquids (e.g., saline, blood, etc.) from reservoir (504) through conduit (524) and vacuum port (514); while permitting a vacuum to be communicated or induced therethrough.

Float (516) has properties (e.g., density) such that it will float in a liquid but will not be drawn upward when a vacuum is induced within reservoir (504). In other words, when vacuum source (412) is activated to induce a vacuum through vacuum port (514), float (516) will not necessarily be drawn up against funnel member (520). The vacuum may therefore be communicated "around" float (516) and through funnel member (520). However, as reservoir (504) fills with liquid, float (516) will begin to float up toward funnel member (520). Eventually, liquid drawn into reservoir (504) via tubes (402, 404) and top ports (512) may reach a level within reservoir (504) to a point where float (516) engages funnel member (520) in a manner sufficient to prevent fluid from passing between float (516) and funnel member (520). Furthermore, such engagement between float (516) and funnel member (520) may prevent a vacuum from being communicated to reservoir (504) by vacuum port (514). Such blockage of vacuum communication may be sensed within biopsy system (2), and may trigger some sort of notification that vacuum canister (500) is substantially full of liquid. For instance, a vacuum blockage may affect an automatic shutoff of vacuum source (412). A vacuum blockage may also trigger a visual indication on a graphical user interface and/or an audible signal.

Those of ordinary skill in the art will appreciate in view of the teachings herein that filter (522), float (516), cage (518), and funnel member (520) are all merely exemplary. Indeed, any other suitable devices or structures may be used in addition to or in lieu of such components. Alternatively, such components may be simply omitted altogether. In other words, the inventors contemplate that a variety of other configurations for vacuum canister (500) may be used, and that, like every other component of biopsy system (2) described herein, vacuum canister (500) need not be limited to the particular construction that is explicitly described herein.

B. Exemplary Tube Connection and Configuration

Figure 50:
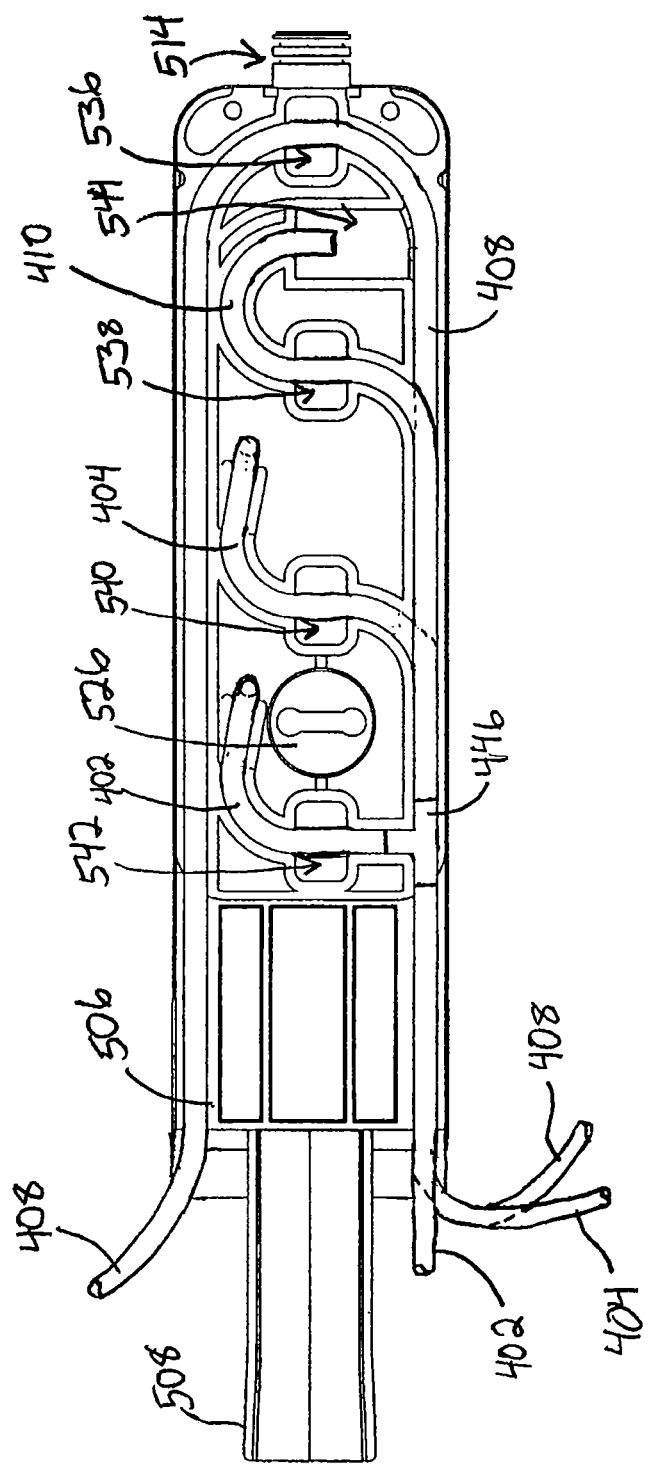
FIG. 50 depicts a top view of the vacuum canister of FIG. 46, with tubes engaged with a top portion of the canister.

FIG. 50 shows an example of tubes (402, 404, 408, 410) being provided in trenches (510). Trenches (510) may include one or more features configured to retain tubes (402, 404, 408, 410) within trenches (510). For instance, inwardly-directed ribs or protrusions may be provided near the tops of trenches (510). Alternatively, the sidewalls of trenches (510) may provide an interference fit; or may be slanted, such that the tops of the sidewalls of trenches (510) provide less clearance than the bottoms of the sidewalls. Alternatively, an adhesive may be used to secure tubes (402, 404, 408, 410) within trenches (510). As yet another variation, one or more caps, clasps, or other members may be secured over portions of tubes (402, 404, 408, 410) to secure tubes (402, 404, 408, 410) within trenches (510). Other ways in which tubes (402, 404, 408, 410) may be secured or retained within trenches (510) will be apparent to those of ordinary skill in the art.

A plurality of top ports (512) are formed on lid portion (506), and each top port (512) is configured have one of tubes (402, 404) coupled therewith. In particular, each top port (512) is configured to provide a path for fluid communication from a connected tube (402, 404) to the reservoir (504) defined by base portion (502). In one embodiment, canister (500) is pre-packaged with tubes (402, 404, 408, 410) already positioned in trenches (510), in addition to having tubes (402, 404) coupled with probe (102, 103) prior to product packaging. In other embodiments, canister (500) and/or probe (102, 103) may be packaged without some or all of tubes (402, 404, 408, 410) already connected. However, in some embodiments where canister (500) and probe (102, 103) come with tubes (402, 404, 408, 410) pre-connected, aside from inserting canister (500) in canister compartment (458) as described below, a user may have connection of tube (408) with a saline bag (444) as the only fluid connection that the user needs to make. Of course, in embodiments where saline is not used, fluid communication for biopsy system (2) may be ready for use as soon as the user inserts canister (500) into canister compartment (458).

As is shown in FIG. 1, tube (408) is fed into tube (402). As is shown in FIGS. 1 and 50, tube (410) is also fed into tube (402). In particular, a connector (446) connects vent tube (410) with tube (402); and a connector (448) connects saline tube (408) with tube (402). As shown, connector (446)

is provided adjacent to canister (500), while connector (448) is provided near biopsy probe (102, 103). In the present example, connectors (446, 448) simply provide a constantly open conduit between tubes (410, 402) and tubes (408, 402), respectively. In other embodiments, connectors (446, 448) may have any other suitable components (e.g., valve, etc.). It will be appreciated in view of the disclosure herein that the configuration of tubes (402, 408, 410) and connectors (446, 448) permits any of a vacuum, vent, or saline to be communicated through tube (402). An exemplary determination of which of these will be communicated through tube (402) will be described in greater detail below.

C. Exemplary Vacuum Control Module

As shown in FIGS. 46-47 and 52-58, the vacuum control module (400) of the present example comprises an outer casing (414), a vacuum canister slot (416), a handle portion (418), and a user interface (700). Outer casing (414) includes a face portion (420), behind which resides a display screen (702), capacitive switches (704), and a speaker (706). Face portion (420) is configured such that display screen (702) can be viewed therethrough; such that capacitive switches (704) may be activated therethrough; and such that sounds coming from speaker (706) can be heard therethrough. As will be described in greater detail below, display screen (702), switches (704), and speaker (706) may be regarded as collectively forming user interface (700). Outer casing (414) further comprises a top cover (422), a wraparound cover (424), and trim pieces (426).

Outer casing (414) is configured such that outer casing (414) is relatively easy to clean. For instance, surface transitions (e.g., between face portion (420), top cover (422), a wraparound cover (424), and trim pieces (426), etc.) are reduced. Furthermore, with capacitive switches (704) being provided behind face portion (420) in lieu of conventional push buttons or other mechanical input components, fluid ingress and dirt capture areas are reduced if not eliminated.

Figure 53:
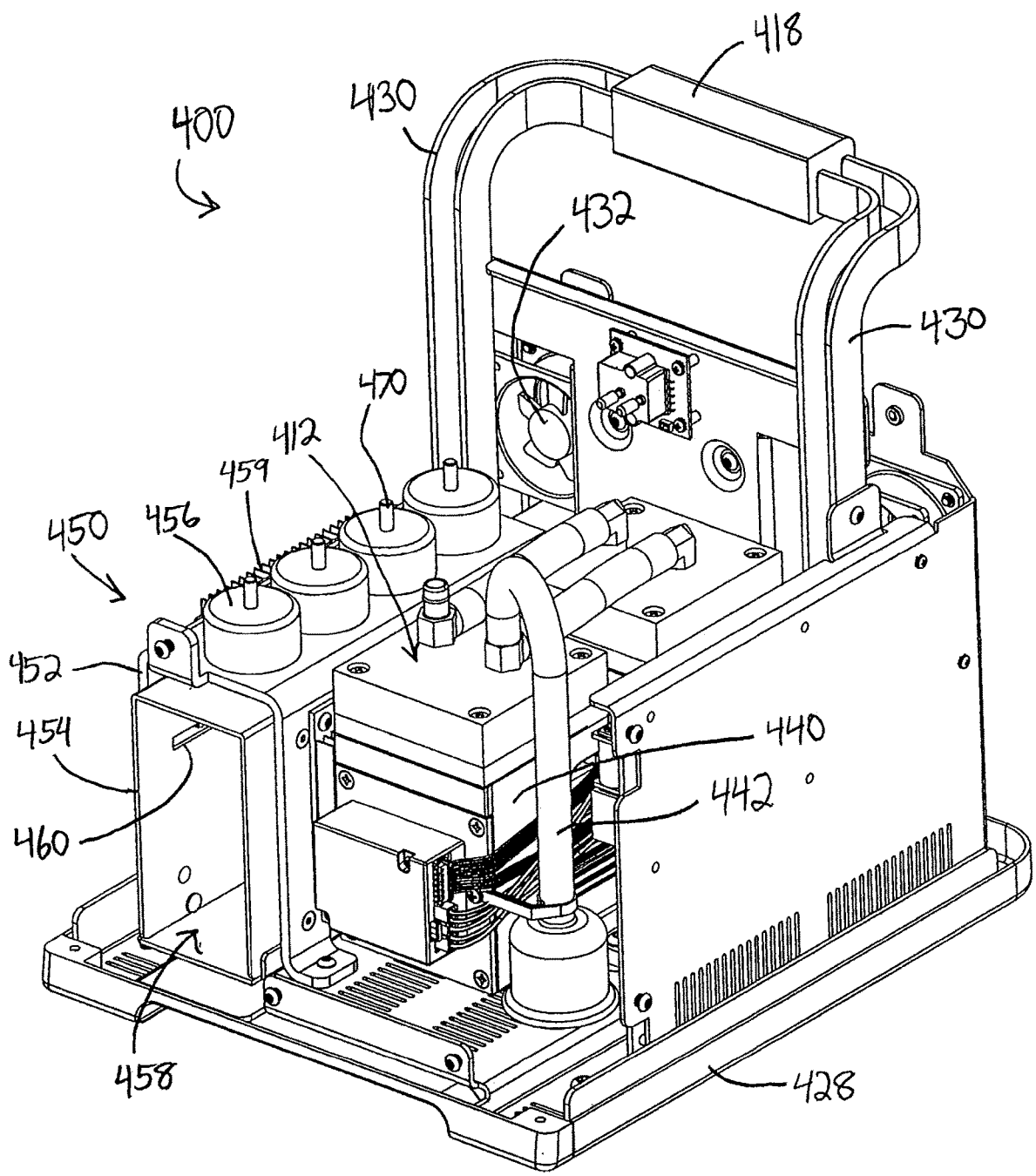
FIG. 53 depicts the vacuum control module of FIG. 46, with an outer casing removed.
Figure 54:
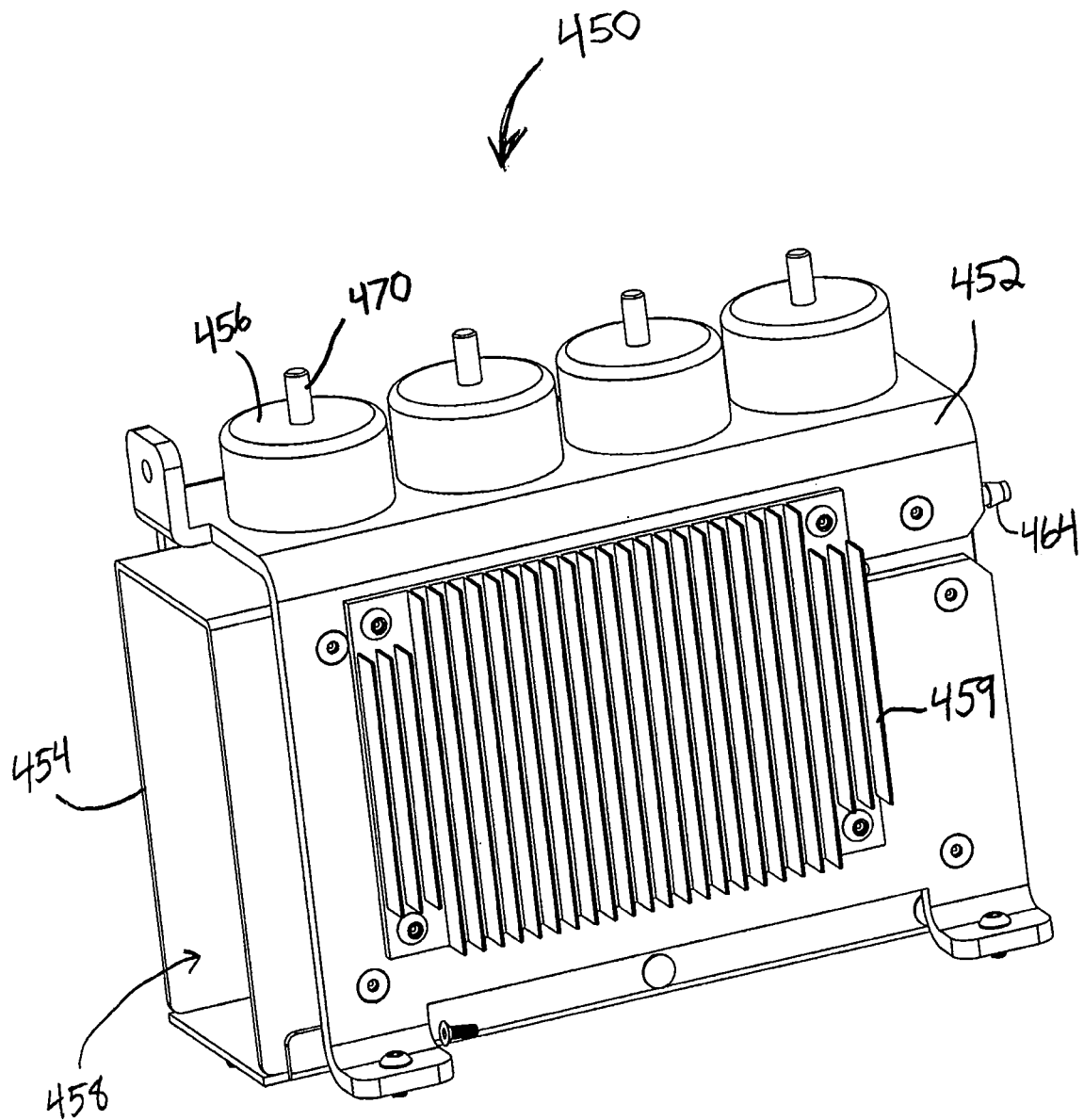
FIG. 54 depicts a perspective view of a vacuum canister port assembly of the vacuum control module of FIG. 46.
Figure 55:
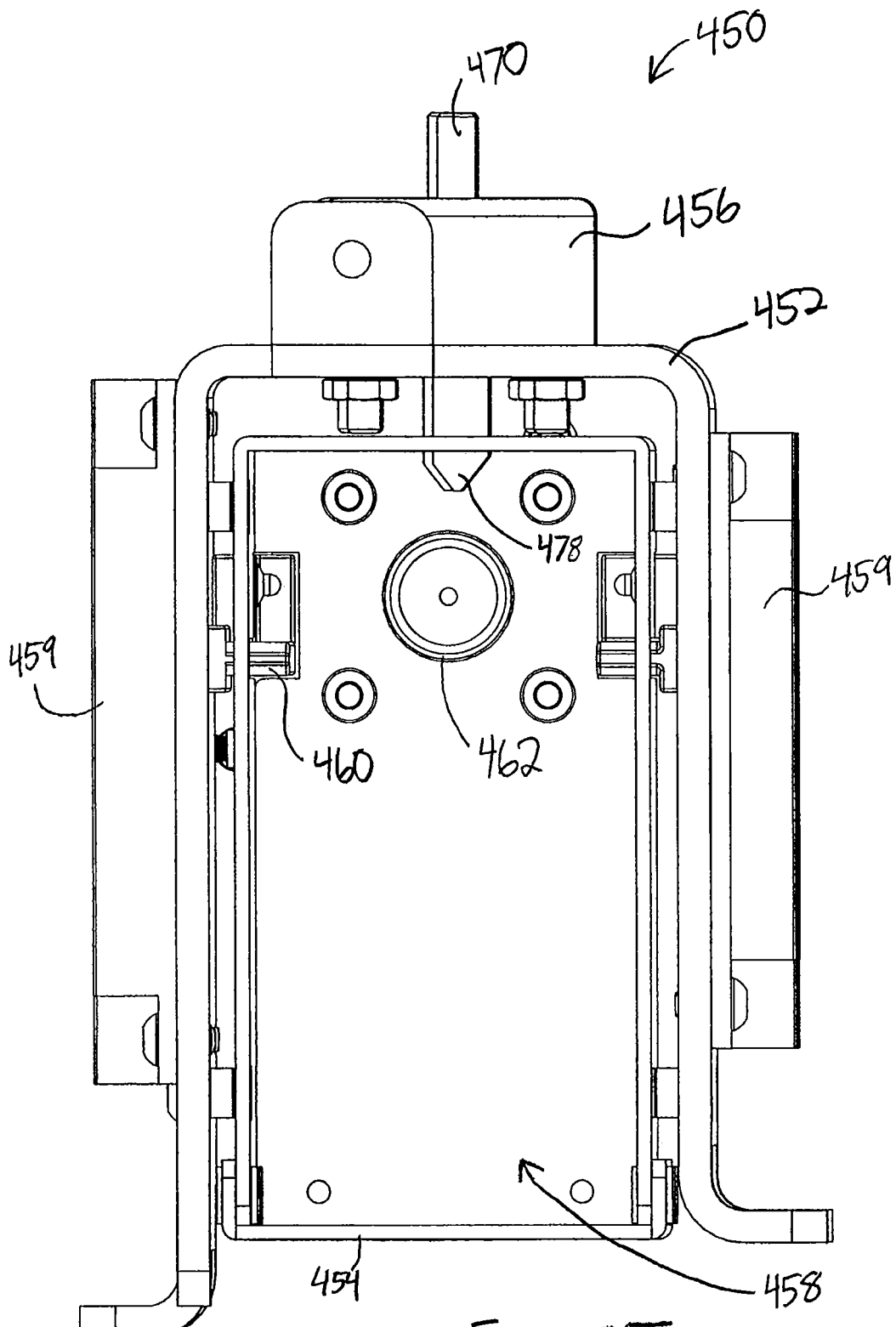
FIG. 55 depicts a front view of the vacuum canister port assembly of FIG. 54.
Figure 56:
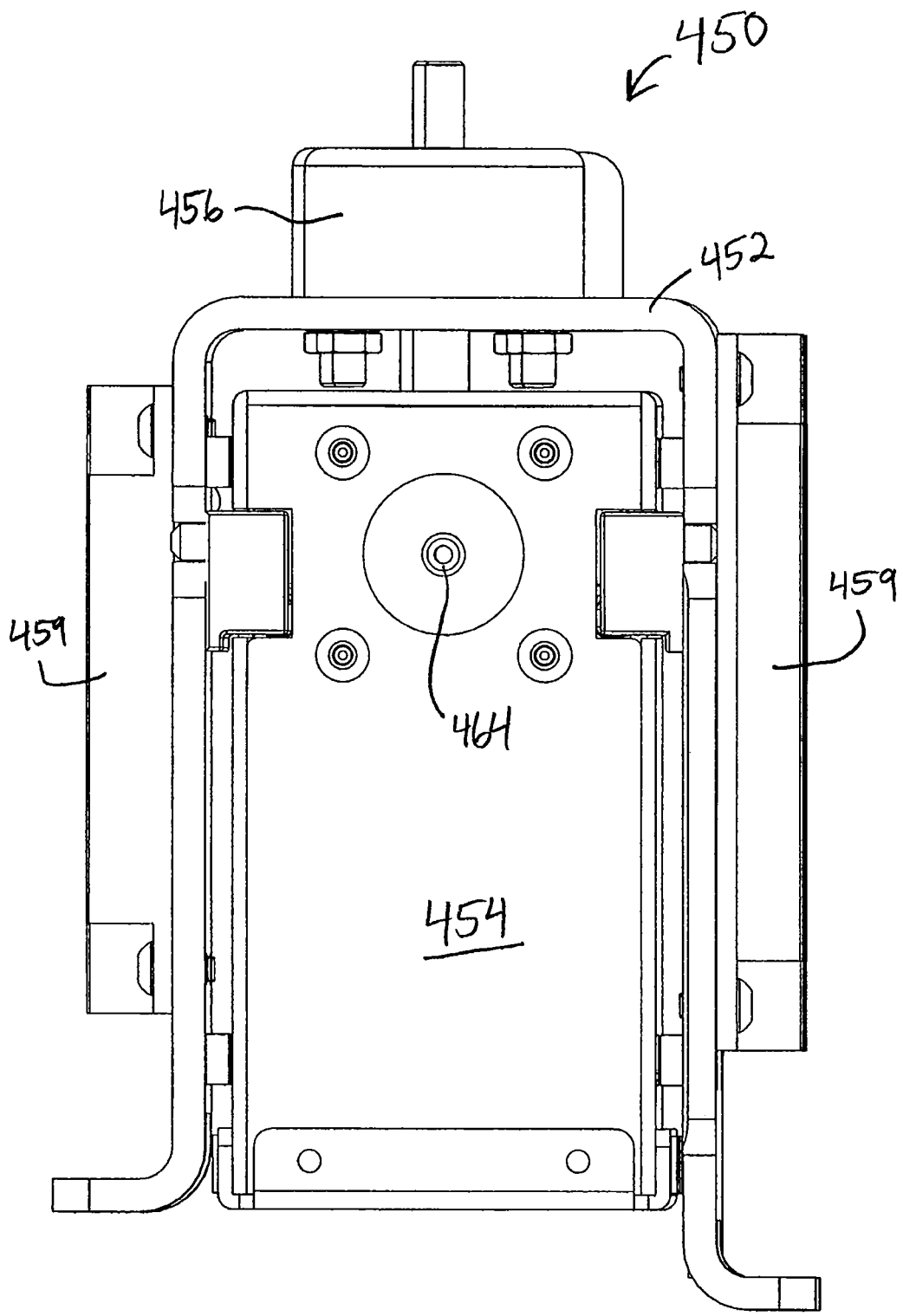
FIG. 56 depicts a rear view of the vacuum canister port assembly of FIG. 54.
Figure 57:
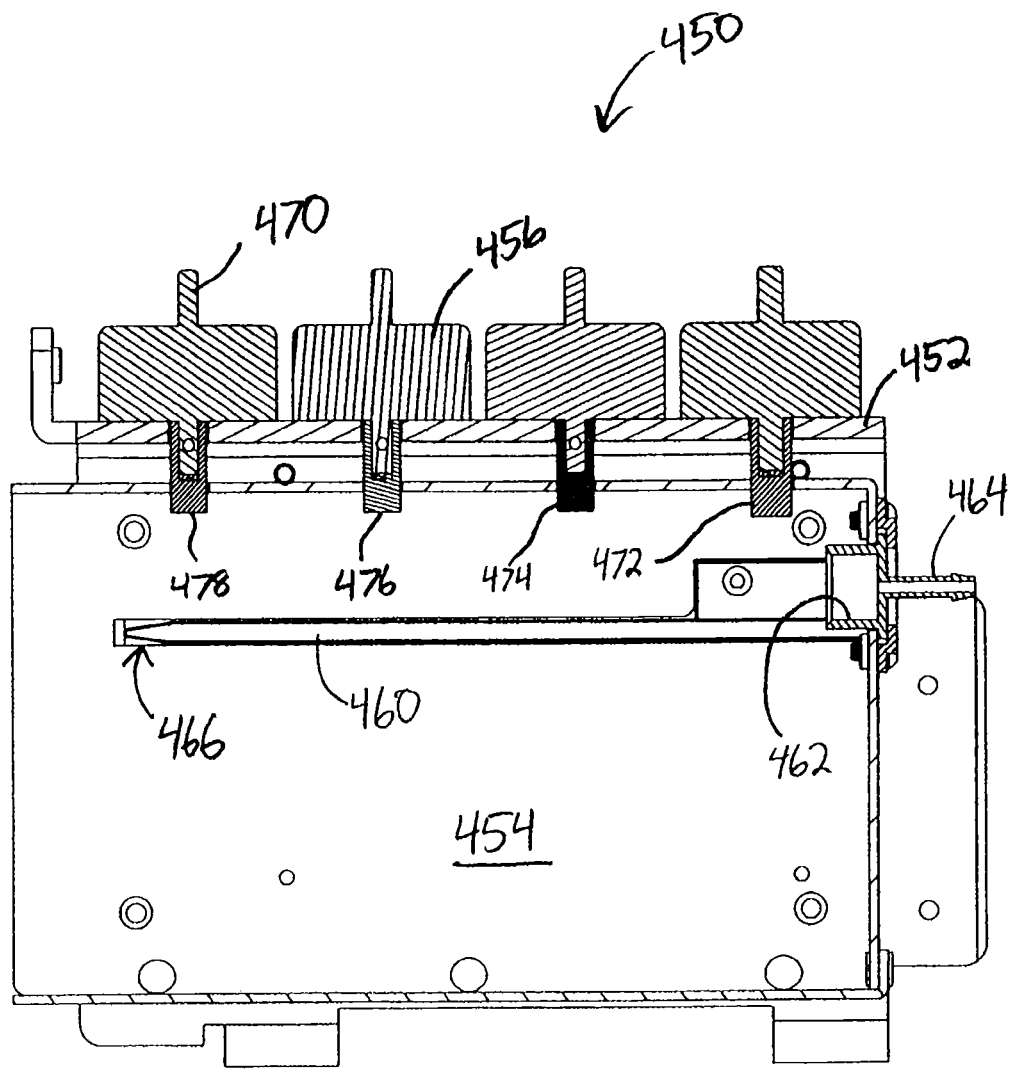
FIG. 57 depicts a cross-sectional view of the vacuum canister port assembly of FIG. 54.
Figure 58:
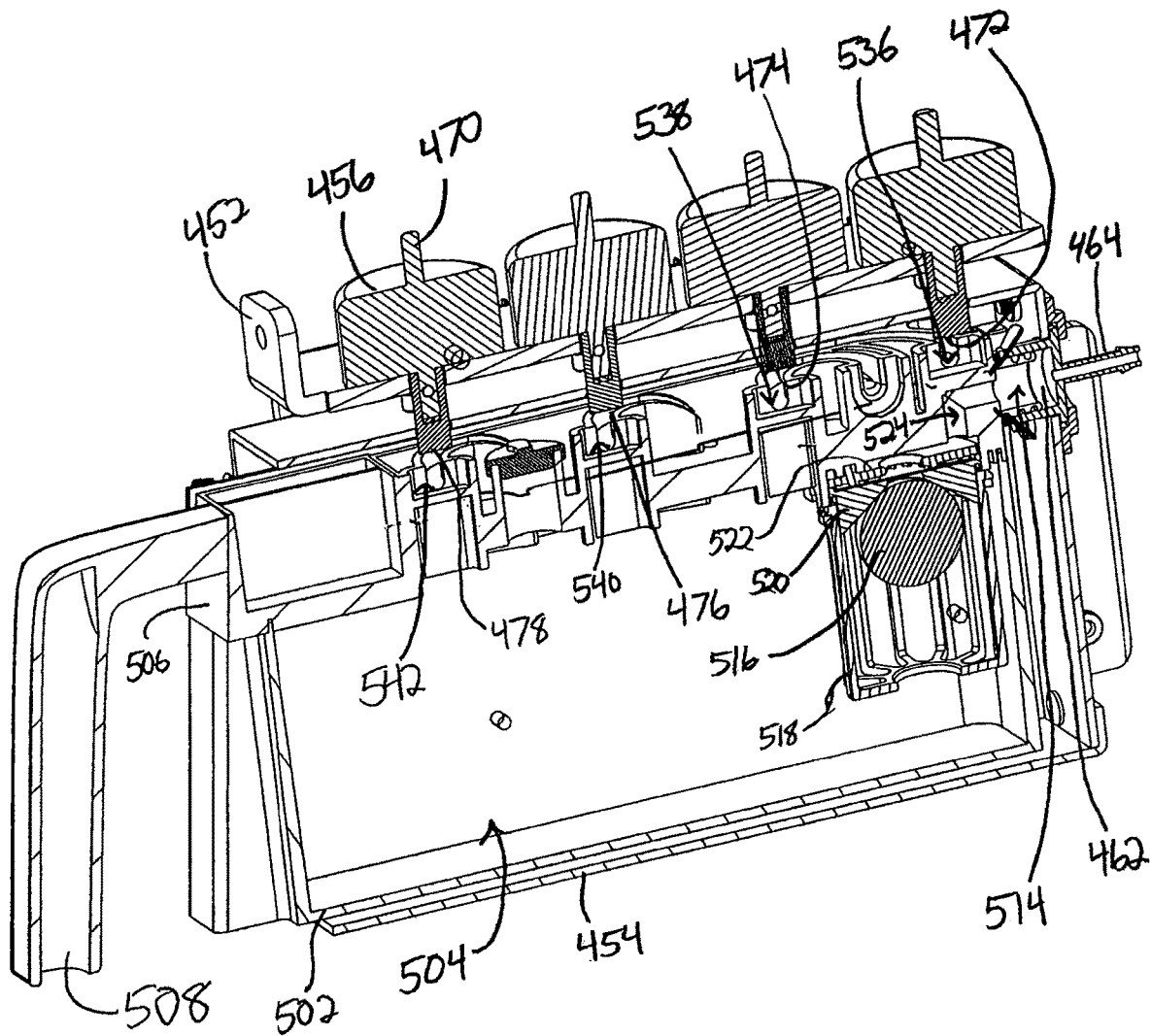
FIG. 58 depicts a cross-sectional view of the vacuum canister port assembly of FIG. 54 with the vacuum canister of FIG. 46 inserted therein.

As shown in FIG. 53, vacuum control module (400) of the present example further comprises a base portion (428), which has a pair of upright members (430) extending upwardly therefrom and inwardly toward each other, meeting at handle portion (418). Accordingly, base portion (428), upright members (430), and handle portion (418) are configured such that when a user carries vacuum control module (400) by handle portion (418), the weight of vacuum control module (400) is borne by base portion (428) and upright members (430). In one embodiment, upright members (430) and handle portion are collectively formed by a unitary metal member fixedly secured to base member (428), such as via screws, bolts, welds, or using other components or techniques. Handle portion (418) may further comprise a plastic overmold formed about such a unitary metal member. Of course, as with other components described herein, upright members (430) and handle portion (418) may be formed in a variety of alternative ways using a variety of alternative structures and techniques.

With handle portion (418), vacuum control module (400) may be provided as a substantially portable unit. For instance, vacuum control module (400) may have a size and weight (e.g., less than 10 kg) such that a single user may pick up and carry control module (400), by handle portion (418) or otherwise, with relative ease. Vacuum control module (400) may also be used with or without a cart. For instance, portability of vacuum control module (400) may permit it to simply be set on a tabletop or other location. Such portability may be desirable in MRI suite settings or in other settings.

Vacuum control module (400) of the present example also includes fans (432) and a vent (433), though these components may be varied or omitted. Vacuum control module (400) also includes a ground lug (434), a USB port (436), and an Ethernet port (438). In addition, vacuum control module (400) includes a cord socket (435) for connecting vacuum control module (400) to an AC outlet using a conventional cord, and a power switch (439). It will be appreciated by those of ordinary skill in the art in view of the teachings herein that USB port (436) and/or Ethernet port (438) may be used to couple vacuum control module (400) with a variety of other devices, including but not limited to a local or remote desktop or laptop computer, the internet, a local area network, any other network, a storage device, or a device associated with one or more particular imaging modalities (e.g., a pod or cart associated with Magnetic Resonance Imaging, etc.). Such ports (436, 438) may permit data and/or commands to be communicated from vacuum control module (400) to an external device. In addition or in the alternative, ports (436, 438) may permit data and/or commands to be communicated from an external device to vacuum control module (400). Other ways in which ports (436; 438) may be used will be apparent to those of ordinary skill in the art in view of the teachings herein. Similarly, it will be appreciated that ports (436, 438) may be substituted, supplemented, varied, or omitted as desired.

As also shown in FIG. 53, a vacuum pump (440) is provided in vacuum control module (400). A muffler assembly (442) connected to vacuum pump (440) to reduce noise generated by vacuum pump (440). Vacuum pump (440) and muffler assembly (442) thus collectively provide a vacuum source (412) in the present example, though any other suitable components may be used. For instance, muffler assembly (442) is merely optional. Vacuum pump (440) and muffler assembly (442) are fixedly secured relative to base portion (428), such as via screws, bolts, welds, or using other components or techniques. One or more rubber feet (not shown) or similar components may be positioned between vacuum pump (440) and base portion (428) to absorb vibration generated by vacuum pump, such as to further reduce noise. Other ways in which noise from vacuum pump (440) may be reduced will be apparent to those of ordinary skill in the art in view of the teachings herein.

In the present example, saline is provided for biopsy system (2) by a conventional saline bag (444), which is separate from vacuum control module (400). For instance, saline bag (444) may be coupled with tube (408) using any suitable conventional fitting. In other embodiments, saline is provided from within vacuum control module (400). For instance, vacuum control module (400) may include a feature (not shown) that is operable to receive a conventional saline bag (444), with a port (not shown) for placing tube (408) in fluid communication with saline bag (444). Vacuum control module (400) may alternatively include some other type of reservoir within casing (414) for providing saline. In other embodiments, saline is not used at all with biopsy system (2). It will also be appreciated that vacuum control module (400) may also include a source of pressurized air, such as a pump or charged canister, etc. Such pressurized air may be communicated to a biopsy device (100, 101) for any suitable purpose, including but not limited to communicating pressurized air through one or more lumens (20, 40, 52), activating a component (e.g., pneumatic motor or actuator, etc.) within biopsy device (100, 101), or for any other purpose. Still other components that may be incorporated into or otherwise associated with vacuum control module (400) will be apparent to those of ordinary skill in the art in view of the teachings herein.

D. Exemplary Vacuum Canister Port in Control Module

As shown in FIGS. 53-58, vacuum control module (400) of the present example further comprises a vacuum canister port assembly (450). Vacuum canister port assembly (450) comprises a bracket (452), an inner casing (454), and a plurality of solenoids (456). Bracket (452) is configured to be fixedly secured relative to base portion (428), such as via screws, bolts, welds, or using other components or techniques. Heat sinks (459) are secured to bracket (452), as are solenoids (456) and inner casing (454).

Inner casing (454) defines a canister compartment (458), which is configured to receive vacuum canister (500) as noted above. In particular, rails (460) extend inwardly from the interior of bracket (452), through the sidewalls of inner casing (454), and into canister compartment (458). As described above, rails (460) are configured to engage tracks (530) on vacuum canister (500), to guide vacuum canister (500) as vacuum canister (500) is inserted into canister compartment (458). Each rail (460) has a tapered portion (460) to facilitate engagement with tracks (530) in the present example, though tapered portions (460) are merely optional. It will be appreciated in view of the disclosure herein that rails (460) may alternatively extend inwardly only from the sidewalls of inner casing (454) rather than from bracket (452). Alternatively, rails (460) may be otherwise configured or positioned, or may be omitted altogether.

E. Exemplary Vacuum Canister Quick-Connect

Inner casing (454) of the present example also includes a vacuum port (462). A port coupler (464) is provided on the exterior of inner casing (454), opposite to vacuum port (462), and is in fluid communication with vacuum port (462). Port coupler (464) is configured to be connected with a tube, hose, or other structure for fluidly coupling port coupler (464) with vacuum pump (440). In other words, vacuum pump (440) may be placed in fluid communication with vacuum port (462) via a tube (not shown) connected with port coupler (464), such that vacuum pump (440) may draw a vacuum through vacuum port (462). Vacuum port (462) is configured to engage with vacuum port (514) of vacuum canister (500) when vacuum canister (500) is inserted into canister compartment (458). In particular, vacuum port (462) provides a female-shaped compliment to male-shaped vacuum port (514). O-rings (534) on vacuum port (514) are configured to provide sealed engagement between vacuum port (462) and vacuum port (514). Of course, the male-female arrangement between vacuum ports (462, 514) may be reversed, or some other relationship between vacuum ports (462, 514) may be provided. Furthermore, other variations may be used where o-rings (534) are substituted, supplemented, or omitted altogether.

F. Exemplary Pinching Valve System

Solenoids (456) each include a respective rod (470). Each rod (470) has a corresponding engagement tip (472, 474, 476, 478) secured unitarily thereto. Each solenoid (456) is operable to selectively move its rod (470) with tip (472, 474, 476, 478) upward or downward when solenoid (456) is activated, the upward or downward movement being dependent on the signal communicated to each solenoid (456). Rods (470) are positioned such that, when vacuum canister (500) is inserted in canister compartment (458), tips (472, 474, 476, 478) may be selectively engaged with tubes (402, 404, 408, 410) through selective activation of solenoids (456). In particular, when vacuum canister (500) is inserted into canister compartment (458) of vacuum control module (400), tip (472) is positioned to selectively engage saline tube (408), tip (474) is positioned to selectively engage vent tube (410), tip (476) is positioned to selectively engage axial vacuum tube (404), and tip (478) is positioned to selectively engage lateral vacuum tube (402).

Recesses (536, 538, 540, 542) are formed in lid portion (506) of vacuum canister (500), and are configured to provide sufficient clearance for tips (472, 474, 476, 478) to fully engage tubes (402, 404, 408, 410). Such engagement may include tips (472, 474, 476, 478) pinching tubes (402, 404, 408, 410) against lid portion (506) (e.g., using lid portion (506) as an engagement surface), to thereby prevent fluid communication through tubes (402, 404, 408, 410).

In the present example, recess (536) is configured to permit tip (472) to fully engage saline tube (408), recess (538) is configured to permit tip (474) to fully engage vent tube (410), recess (540) is configured to permit tip (476) to fully engage axial vacuum tube (404), and recess (542) is configured to permit tip (478) to fully engage lateral vacuum tube (402). Such full engagement of tips (472, 474, 476, 478) with tubes (402, 404, 408, 410) will serve to prevent fluid from being communicated through fully engaged tubes (402, 404, 408, 410) in this example. In other words, solenoids (456), rods (470), and tips (472, 474, 476, 478) may be used to serve a valving function with respect to tubes (402, 404, 408, 410), such that selective activation of solenoids (456) may permit or prevent communication of fluid through tubes (402, 404, 408, 410). Suitable combinations of permitting/preventing fluid communication through tubes (402, 404, 408, 410) during use of biopsy system (2) will be described in greater detail below.

In some variations, each solenoid (456) is engaged with one or more resilient members (e.g., springs, etc.). For instance, such resilient members may be located at the bottom of solenoids (456), and may be used to control tolerance stack-up and match the force profile of solenoids (456) to the force profile of tubes (402, 404, 408, 410). Of course, such resilient members may be located elsewhere and may perform other functions in addition to or in lieu of those mentioned above. Similarly, other components may be used to control tolerance stack-up and match force profiles. Alternatively, such resilient members or other components may be simply omitted altogether.

While fluid control is provided by solenoids (456), rods (470), and tips (472, 474, 476, 478) in the present example, it will be appreciated that fluid control may be provided in a variety of alternative ways. For instance, alternative valving devices or systems may be provided within vacuum control module (400). Alternatively, all or some valving functions may be performed within biopsy device (100, 102). For instance, a constant vacuum may be communicated to biopsy device (101, 102), and a valving member within biopsy device (101, 102) may be operable to selectively communicate such a vacuum to vacuum lumen (40) and/or cutter lumen (52). In other embodiments, one or more of motors within biopsy device (100, 101) may be used to control a vacuum pump that is located within biopsy device (100, 101) to provide a vacuum. Such a vacuum motor may be dedicated to controlling such a pump, or a preexisting motor (246, 272, 282, 312, 322) may be used to control such a pump. Still other ways in which communication of fluid (e.g., saline, vacuum, venting, etc.), through tubes (402, 404, 408, 410) or otherwise within biopsy system (2), may be selectively controlled or provided will be apparent to those of ordinary skill in the art in view of the teachings herein.

G. Exemplary Crushable Tubing

Figure 59:
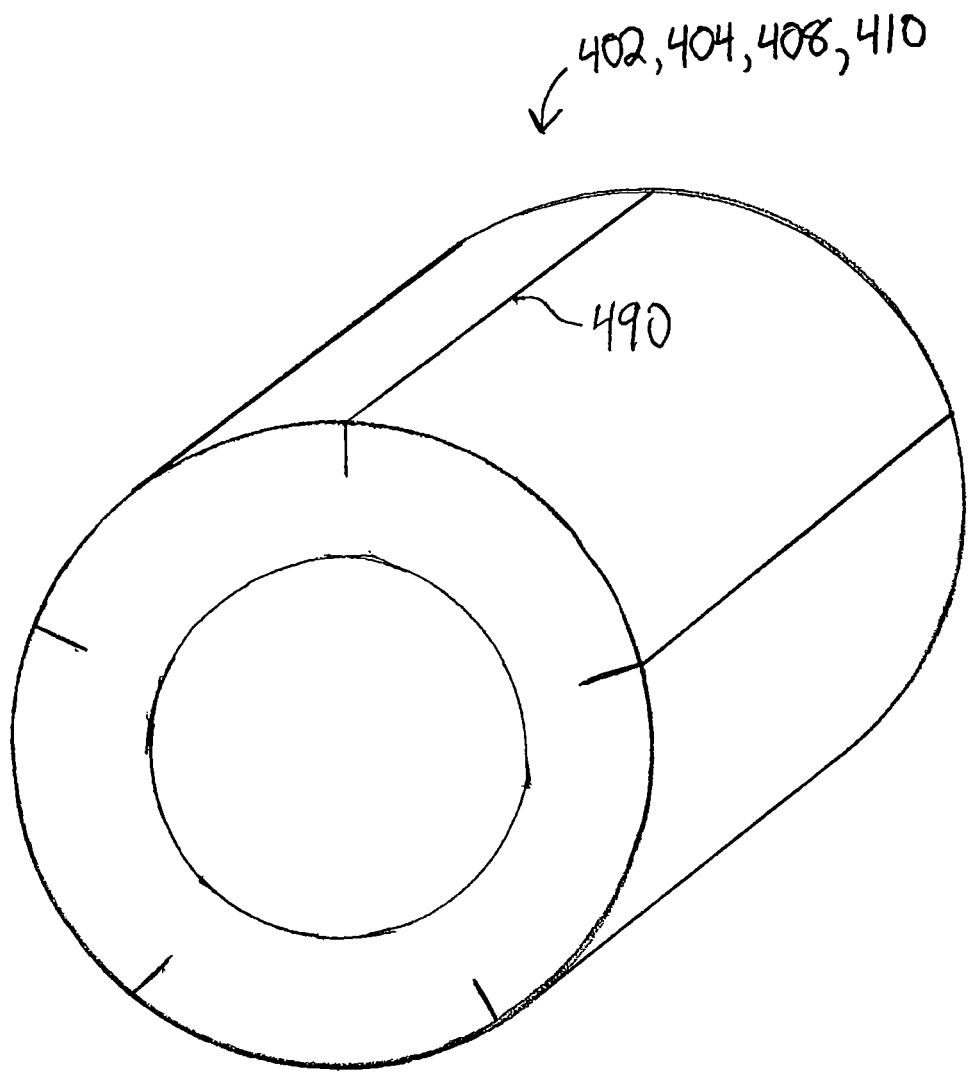
FIG. 59 depicts a perspective, cross-sectional view of an exemplary tube.

In some embodiments, and as shown in FIG. 59, tubes (402, 404, 408, 410) are formed with a plurality of longitudinal slits (490). In the present example, slits (490) extend along the full length of each of tubes (402, 404, 408, 410). In other embodiments, slits (490) are provided only along the portions of the lengths of tubes (402, 404, 408, 410) where tubes (402, 404, 408, 410) will be selectively engaged by tips (472, 474, 476, 478). With tubes (402, 404, 408, 410) being formed of a low durometer polymer with slits (490), tubes (402, 404, 408, 410) have a relatively low resistance to being crushed by tips (472, 474, 476, 478) in a manner sufficient for fluid communication to be stopped in a tube (402, 404, 408, 410) that is being crushed by a tip (472, 474, 476, 478). However, tubes (402, 404, 408, 410) still have sufficient strength to refrain from collapsing when a vacuum is induced within tubes (402, 404, 408, 410), despite having slits (490). Tubes (402, 404, 408, 410) may also have sufficient thickness to provide resistance to kinking.

It will be appreciated in view of the teachings herein that slits (490) may be formed in tubes (402, 404, 408, 410) using a variety of techniques. For instance, when tubes (402, 404, 408, 410) are formed using a thermoplastics extrusion process, cold knives may be provided at the exit of an extrusion die to cut the material while it is still hot. Alternatively, when tubes (402, 404, 408, 410) are formed using a thermoset extrusion process, hot knives may be provided at the exit of an extrusion guide to cut the material while it is still green. Alternatively, slits (490) may be formed by cutting downstream of a curing oven or cooling bath. Other ways in which slits (490) may be formed will be apparent to those of ordinary skill in the art in view of the teachings herein. It will also be appreciated that slits (490) may have any other suitable configuration (e.g., number of slits (490), depth of slits (490), length of slits (490), selection of which tubes (402, 404, 408, 410) have slits (490), etc.). Of course, slits (490) may simply be omitted altogether.

Furthermore, one or more of tubes (402, 404, 408, 410) may be colored or translucent, such as to conceal blood that may be communicated therethrough.

H. Exemplary Motor Control

Vacuum control module (400) of the present example also includes a controller (480) operable to control motors (246, 272, 282, 312, 322) in holsters (202, 302). For instance, a single controller (480) may coordinate between motor functions on different motors (246, 272, 282, 312, 322) that are within the same biopsy system (2). Vacuum control module (400) includes a port (482) for providing communication of motor control signals and power to motors (246, 272, 282, 312, 322) via a cable (484). In other embodiments, motor control signals are provided wirelessly. While holster (202) of the present example has three motors (246, 272, 282) and holster (302) of the present example has two motors (312, 322), the same controller (480) and port (482) may be used to control each holster (202, 302). Alternatively, each holster (202, 302) may have a respective dedicated port on vacuum control module (400).

Motors (246, 272, 282, 312, 322) may include any suitable combination of brushed or brushless technology. For instance, one or more of motors (246, 272, 282, 312, 322) may be a brushless motor that uses optical commutation. In some embodiments, the use of optical commutation may provide a degree of immunity to high ambient magnetic fields, such as those that may be found in an MRI suite. A merely illustrative example of a motor using optical commutation is disclosed in U.S. Pat. No. 5,424,625, entitled "Repulsion Motor," issued Jun. 13, 1995, the disclosure of which is incorporated by reference herein. Another merely illustrative example of a motor using optical commutation is disclosed in U.S. Pat. No. 7,053,586, entitled "Brushless Repulsion Motor Speed Control System," issued May 30, 2006, the disclosure of which is incorporated by reference herein.

By way of example only, one or more of motors (246, 272, 282, 312, 322) may include an OPTEK OPR5005 reflective miniature surface mount optical source/detector sensor pair. Suitable sensors may include those that are transmissive and/or those that are reflective. Furthermore, the light that is used may be coherent (e.g., LASER) or non-coherent (e.g., generated by an LED). Either visible or invisible light spectra may be used. In the present example, a reflective infrared (IR) sensor comprising an IR photodiode and an IR phototransistor is used. The optosensors are arrayed around the motor shaft in 120° increments in a circular array on a printed circuit board and in angular alignment with the phase coils of the motor. A flag or optical interrupter that is aligned with magnets on the rotor is affixed to the motor shaft that transmissive/non-reflective for half of its perimeter and reflective/non-transmissive over the other half. When the phase coils are properly aligned with the optical sensors and the optical flag is properly alighted with the magnetic poles on the rotor, a 60° position sensing of the rotor is possible, just as it is with hall effect sensors. In addition, the logic level output from the optical sensors may be made identical to that of the hall effect sensors, allowing interchangeability of sensing types with control hardware such as controller (480). Other suitable constructions for motors (246, 272, 282, 312, 322), including those using optical commutation or otherwise, will be apparent to those of ordinary skill in the art in view of the teachings herein.

Controller (480) of the present example comprises a Magellan 4 axis chipset from Performance Motion Devices, Inc. of Lincoln, Mass. In one embodiment, controller (480) is configured to use hall effect signals for position-based control of any one of motors (246, 272, 282, 312, 322). For instance, as noted above, motors (282, 322) of the present example are operationally coupled with encoder wheels (292) and sensors (296). Such a configuration may provide a three channel (A, B, and Index pulse) quadrature encoder which, in combination with controller (480), permits repeatability of positioning manifold (144, 366) within approximately 0.1 degree.

In some embodiments hall effect sensors are used to provide both commutation and position control of at least one of motors (246, 272, 282, 312, 322). Controller (480) is configured to provide a multiplexing scheme with signals provided by such hall effect sensors and those provided by the sensor (296), whereby sixteen differential signals are multiplexed onto either four or six differential lines that are coupled with port (482) and effectively continued through cable (484). Of course, any other suitable multiplexing scheme may be used, to the extent that any is used at all. Still other suitable configurations for and methods of operating through controller (480) will be apparent to those of ordinary skill in the art in view of the teachings herein.

VI. Exemplary Modes of Operation

It will be appreciated in view of the disclosure herein that there are a variety of methods by which biopsy system (2) may be operated. For instance, regardless of the structures or techniques that are used to selectively control communication of fluid (e.g., saline, vacuum, venting, etc.), through tubes (402, 404, 408, 410) or otherwise within biopsy system (2), there are a variety of timing algorithms that may be used. Such timing algorithms may vary based on an operational mode selected by a user. Furthermore, there may be overlap among operational modes (e.g., biopsy system (2) may be in more than one operational mode at a given moment, etc.). In addition to fluid communication timing algorithms being varied based on a selected mode of operation, other operational aspects of biopsy system (2) may vary based on a selected operational mode. For instance, operation of tissue sample holder (140, 368) may vary based on a selected operational mode, as may operation of cutter (50) and other components of biopsy system (2). Several merely exemplary operational modes will be described in greater detail below, while others will be apparent to those of ordinary skill in the art in view of the teachings herein.

A. Exemplary Presentation of Captured Tissue Samples

Figure 60:
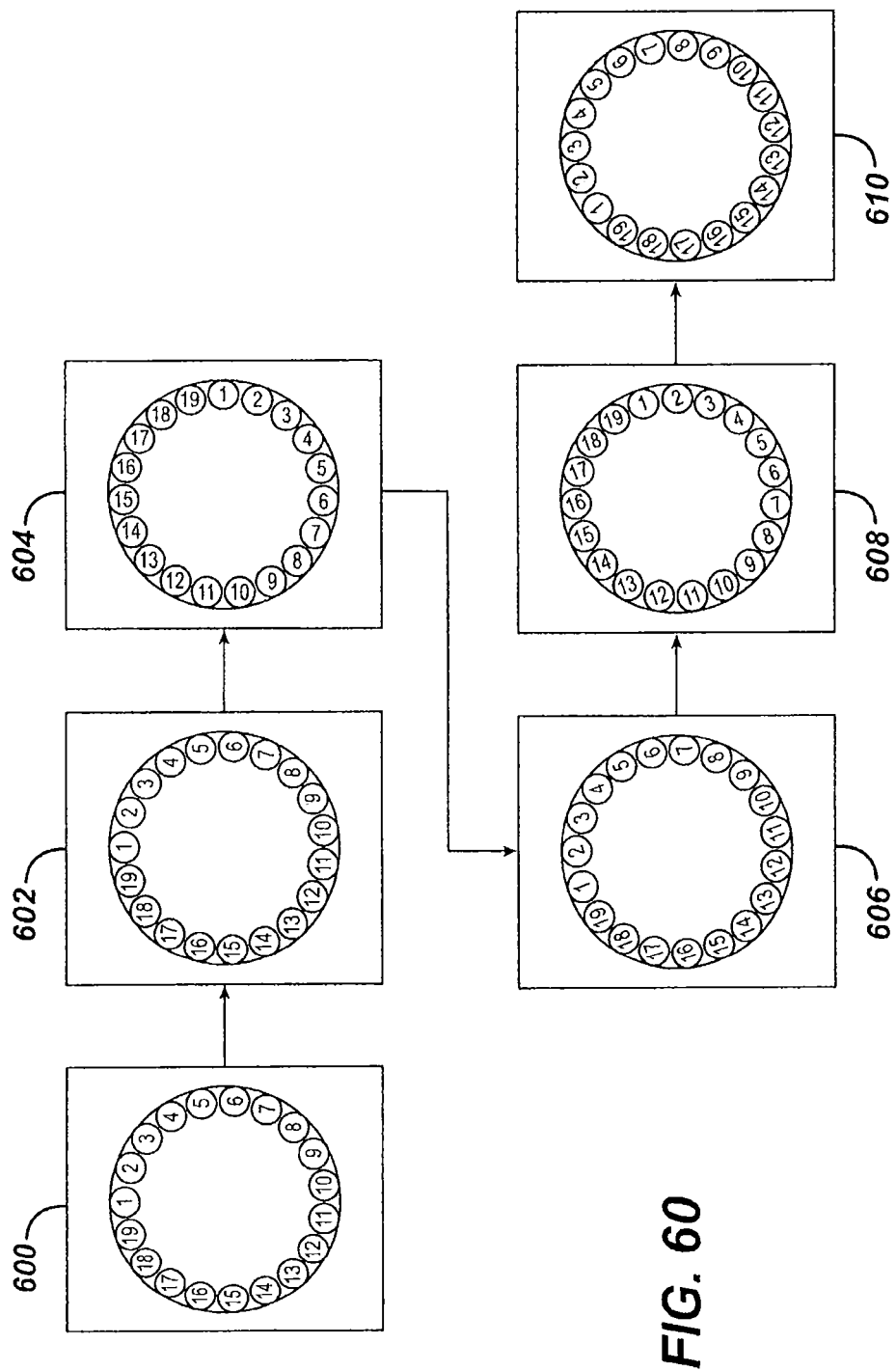
FIG. 60 depicts a schematic flow diagram showing an exemplary rotation sequence of a tissue sample holder.

One merely exemplary operational mode may include a "view sample" mode. In this mode, manifold (144, 366) may be configured to rotate after a tissue sample (4) is acquired, to present the tissue sample (4) to the operator for viewing before the user acquires the next tissue sample. In particular, and as shown in FIG. 60, a tissue sample (4) is drawn into the chamber (166, 388) that is in the twelve o'clock position when the tissue sample (4) is initially acquired. Manifold (144, 366) is then rotated until the tissue sample (4) is at the three o'clock position, thereby permitting a user to easily view the tissue sample (4) from the side of biopsy device (100, 101). Such rotation may occur substantially immediately after tissue sample (4) is drawn into chamber (166, 388). Alternatively, biopsy system (2) may "wait" to see if any user inputs occur within a certain time period (e.g., 2 seconds) after tissue sample (4) has been acquired, then rotate the tissue sample (4) to the three o'clock position only if no user inputs have occurred within that time period.

The rotational position of manifold (144, 366) may be maintained such that tissue sample (4) is kept at the three o'clock position until some other user input is provided. For instance, if a user provides input indicating a desire to obtain another tissue sample (4), biopsy system (2) may rotate manifold (144, 366) to align the next available chamber (166, 388) (e.g., a chamber (166, 388) that is immediately adjacent to the chamber (166, 388) in which the most recently acquired tissue sample (4) resides) with cutter lumen (52). After the next available chamber (166, 388) has been aligned with cutter lumen (52), cutter (50) may be activated to obtain another tissue sample (4), and an axial vacuum may be used to draw this next tissue sample (4) into the next available chamber (166, 388). If a "clear probe" or "aspirate" user input is provided, manifold (144, 366) may be rotated to re-align the chamber (166, 388) in which tissue sample (4) resides with cutter lumen (52), and then the "clear probe" or "aspirate" control may be carried out as described below. Similarly, if a "smart vac" cycle is initiated, which will be described in greater detail below, then manifold (144, 366) may be rotated to re-align the chamber (166, 388) in which tissue sample (4) resides with cutter lumen (52), such that the "smart vac" cycle may be carried out.

An illustration of the rotation sequence of the present example is provided in FIG. 60. As shown in block (600) tissue sample holder (140, 368) is initially configured such that a first chamber (166, 388) is at the twelve o'clock position. Then, as shown in block (602), a tissue sample (4) is communicated to the first chamber (166, 388). With the "view sample" mode activated, manifold (144, 366) then rotates such that the first chamber (166, 388) is at the three o'clock position, as shown in block (604). As shown in block (606), upon receiving user input to initiate another sampling cycle, manifold (144, 366) is rotated to place a second chamber (166, 388) at the twelve o'clock position, such that a tissue sample (4) is then communicated via cutter lumen (52) into the second chamber (166, 388). As shown in block (608), manifold (144, 366) then rotates such that the second chamber (166, 388) is at the three o'clock position to present the second tissue sample (4) to the user. As shown in block (610), the process of the present example repeats for tissue sample (4) acquisition in a third chamber (166, 388). This process may be repeated until all chambers (166, 388) within tissue sample holder (140, 368) are full.

As an alternative to waiting for a user input, tissue sample (4) may be kept in the three o'clock position for a certain time period (e.g., 5 seconds), with the manifold (144, 366) being automatically rotated to align the next available chamber (166, 388) with cutter lumen (52), regardless of whether a user has provided an input. As another non-limiting variation, biopsy system (2) may keep tissue sample (4) in the three o'clock position only for such a time period, unless the user has provided some type of input before the expiration of that time period, which would cause manifold (144, 366) to be rotated as noted above. Still other ways in which timing and/or user inputs may be used to determine the duration for which a tissue sample (4) is kept in the three o'clock position will be apparent to those of ordinary skill in the art in view of the teachings herein. It will also be appreciated that such rotational control of manifold (144, 366) may be carried out at least in part by controller (480), in combination with feedback from encoder wheel (292) and sensor (296), or using any other suitable components.

Biopsy system (2) may also be configured to permit a user to select the nine o'clock position (or any other position) for presentation of tissue sample (4) in lieu of the three o'clock position noted above. Biopsy system (2) may also permit a user to disable the "view sample" mode, such that the only rotation of manifold (144, 366) between acquisition of tissue samples (4) is to align a next available chamber (166, 388) with cutter lumen. Other variations of biopsy system (2) may lack a "view sample" mode or similar mode, as well as components that might be used for such a mode, altogether.

B. Exemplary "Sample" Cycle

Figure 61:
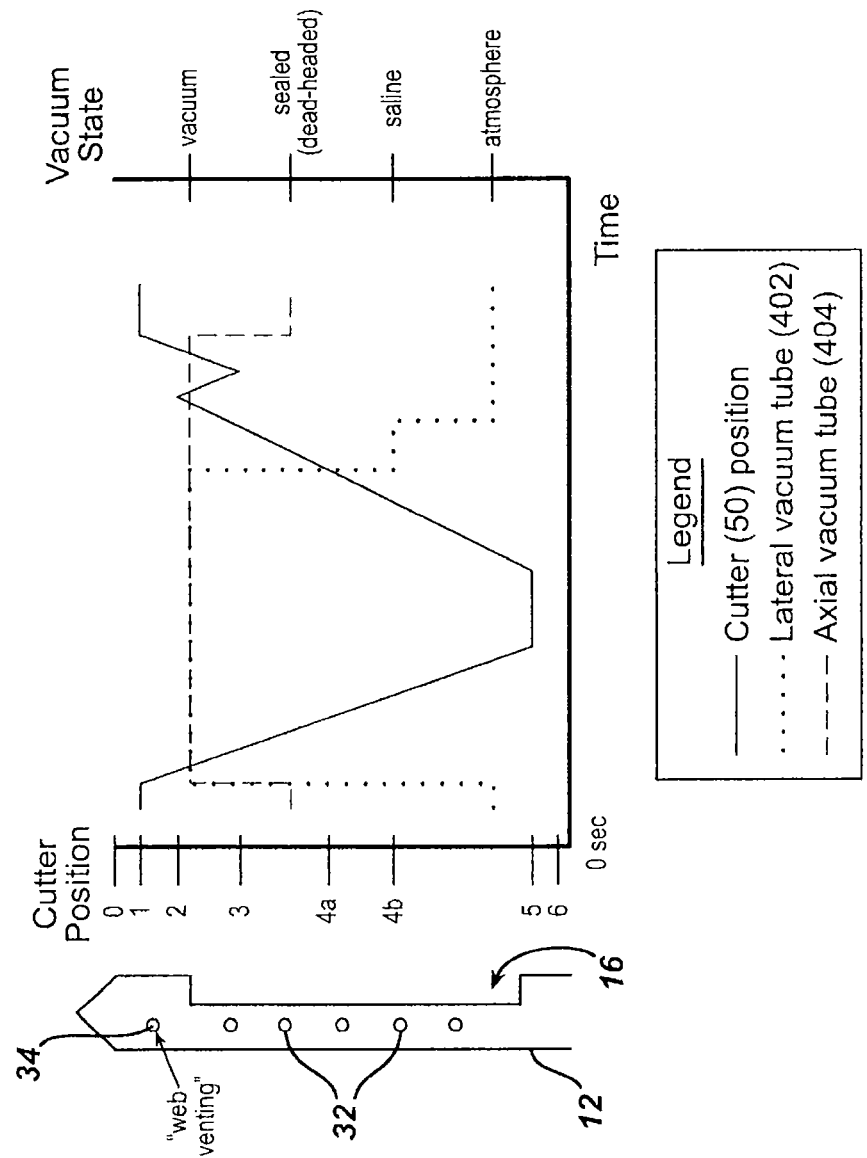
FIG. 61 depicts an exemplary sequence of the position of a cutter within a cannula, relative to fluid communication being provided through lateral and axial vacuum tubes, in an exemplary "sample" cycle.

Another exemplary operational mode, which may overlap with the "view sample" mode discussed above, is a sampling mode, during which a "sample" cycle may be initiated. An exemplary sequence of cutter (50) position within outer cannula (12), relative to fluid communication through tubes (402, 404), in a "sample" cycle is shown in FIG. 61. This cycle is initiated after needle portion (10) has been inserted into the breast of a patient. With needle portion (10) inserted, lateral and axial vacuum are applied. In particular, solenoids (456) are activated such that tips (476, 478) are moved upward to substantially disengage tubes (402, 404), permitting a vacuum to be communicated through tubes (402, 404). Given the fluid connection of tube (402) with needle manifold (80, 366), as well as the transverse openings (32) formed through wall (30), communication of a vacuum through tube (402) will draw a lateral vacuum relative to cannula lumen (20). Communication of a vacuum through tube (404) will draw an axial vacuum through cutter lumen (52), given the fluid connection of tube (404) to cutter lumen (52) via tissue sample holder (140, 368) in this example.

With the axial and lateral vacuum applied as described above, cutter (50) is retracted axially. Such axial retraction is performed using motor (272, 312) and cutter rotation and translation mechanism (120) as described above. The axial retraction of cutter (50) will serve to "open" aperture (16), which results in tissue prolapsing into aperture (16) under the influence of the above-described vacuums. Cutter (50) may dwell in a retracted position for a certain period of time to ensure sufficient prolapse of tissue.

Next, cutter (50) is advanced distally to sever tissue that is prolapsed through aperture (16). Such advancement may be accomplished by simply causing motor (272, 312) to rotate in the direction opposite to the direction in which motor (272, 312) rotated during retraction of cutter (50). In some embodiments, vacuum lumen (40) is switched from vacuum to saline as cutter (50) advances. For instance, solenoids (456) may move tip (478) downward to pinch tube (402), thereby preventing further communication of vacuum through tube (402); and may move tip (472) upward to substantially disengage tube (408), thereby permitting communication of saline through tubes (408, 402). In some other embodiments, vacuum lumen (40) is switched from vacuum to vent as cutter (50) advances. For instance, solenoids (456) may move tip (478) downward to pinch tube (402), thereby preventing further communication of vacuum through tube (402); and may move tip (474) upward to substantially disengage tube (410), thereby permitting venting (e.g., into atmosphere) through tubes (408, 402). In still other embodiments, vacuum lumen (40) alternates between saline and venting. An axial vacuum continues to be communicated through cutter lumen (52) as cutter (50) is advanced.

As the distal end of cutter (50) passes the distal edge of aperture (16), such that cutter (50) "closes" aperture (16), the prolapsed tissue should be severed and at least initially contained within cutter lumen (52). Transverse openings (32) should be configured such that at least one or more of transverse openings (32) are not covered by cutter (50) when cutter (50) has reached a position to "close" aperture (16). With aperture (16) closed and a vent being provided by transverse openings (32) through tube (402), an axial vacuum being communicated through cutter lumen (52) by tube (404) should draw the severed tissue sample (4) proximally through cutter lumen (52) and into a chamber (166, 388) of tissue sample holder (140, 368). Cutter rotation and translation mechanism (120) may also be controlled to cause cutter (50) to reciprocate one or more times through a slight range of motion at a distal position to sever any remaining portions that may have not been completely severed in the first pass of cutter (50).

Before tissue sample (4) is communicated proximally through cutter lumen (52), with aperture (16) being closed by cutter (50), vacuum lumen (40) being vented by tubes (402, 410), and an axial vacuum being provided by tube (404) via cutter lumen (52), cutter (50) is retracted slightly to expose a portion of aperture (16) for a short period of time. During this time, saline may be provided at atmospheric pressure to vacuum lumen (40) by tubes (402, 408). Further retraction of cutter (50) exposes more transverse openings (32), thereby increasing fluid communication between vacuum lumen (40) and cannula lumen (20). Retraction of cutter (50) also exposes the pressure of the tissue cavity (from which tissue sample (4) was obtained) to the distal surface of tissue sample (4). As a result of the slight retraction of cutter (50) in this particular example, the likelihood of atmospheric pressure being applied to the distal face of tissue sample (4) may be increased to help ensure that severed tissue sample (4) does not remain in needle portion (10) (a.k.a. a "dry tap"). Cutter (50) is then fully advanced distally, closing both aperture (16) and all transverse openings (32). Such "closure" of transverse openings (32) may ensure that if medication is applied at this time (between samples) to reduce pain, it will reach the breast cavity through external openings (22) instead of being aspirated through transverse openings (32) and through cutter lumen (52) and tissue sample holder (140, 368).

With the cutter (50) being completely advanced (e.g., such that all transverse openings (32) and aperture (16) are closed), and severed tissue sample (4) being communicated proximally through cutter lumen (52) and into a chamber (166, 388) by an axial vacuum drawn by tube (404), biopsy device (100, 101) will be in a ready state. In this ready state, vacuum lumen (40) is vented to atmosphere, and axial vacuum tube (404) is sealed (a.k.a. "dead-headed"). In other words, tip (472) is pinching saline tube (408) to prevent fluid communication therethrough, tip (474) is substantially disengaged from vent tube (410) to permit venting to atmosphere therethrough, tip (476) is pinching axial vacuum tube (404) to prevent fluid communication therethrough, and tip (478) is pinching lateral vacuum tube (402) to prevent fluid communication therethrough. In this ready state, biopsy device (100, 101) is ready to obtain another tissue sample (4), such as by initiating another sampling sequence as described above.

It will be appreciated that a "sample" cycle may be carried out in a variety of alternative ways. For instance, motion of cutter (50) may vary during the process of acquiring a tissue sample. Furthermore, the timing of, sequence of, and interrelationships between lateral vacuum, axial vacuum, venting, and saline may be varied in a number of ways. Accordingly, the inventors contemplate a host of other permutations of such variables, and do not consider the invention to be limited in any way to the merely illustrative permutations explicitly discussed in detail above.

C. Exemplary "Clear Probe" Cycle

Figure 62:
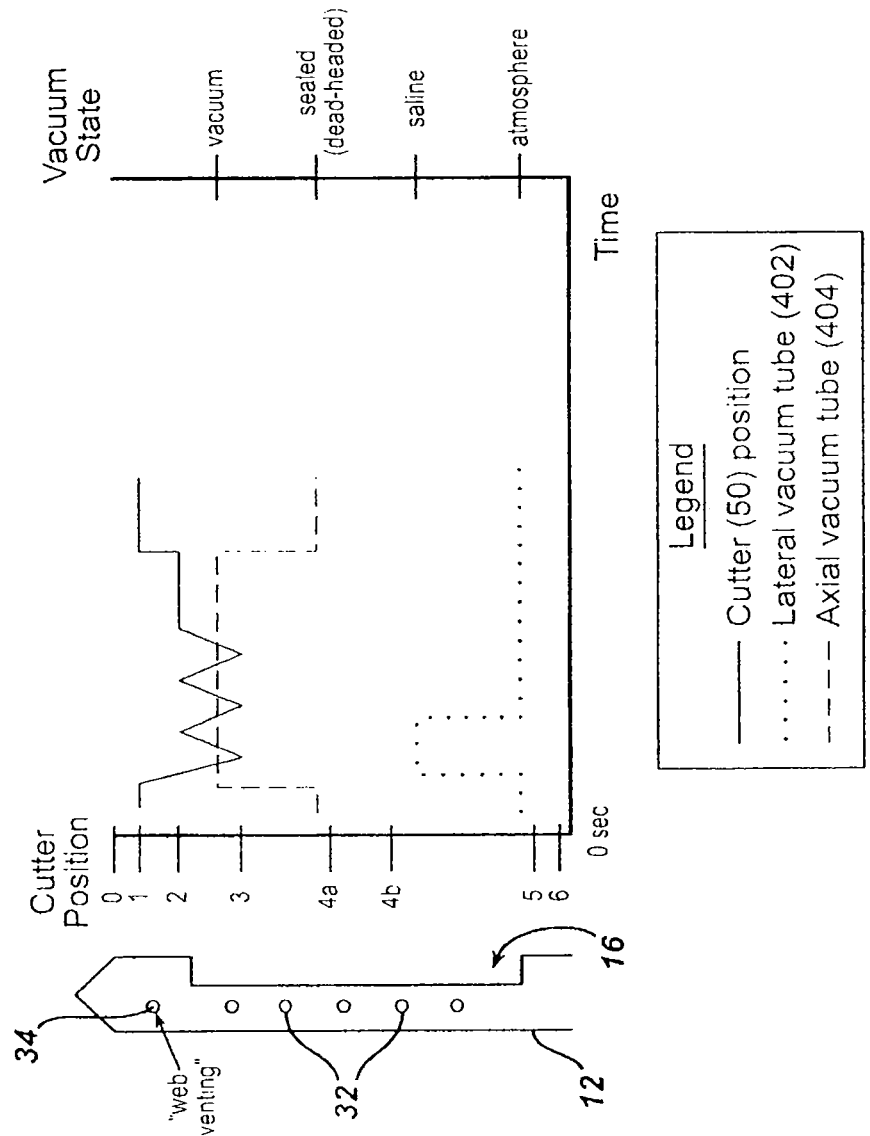
FIG. 62 depicts an exemplary sequence of the position of a cutter within a cannula, relative to fluid communication being provided through lateral and axial vacuum tubes, in an exemplary "clear probe" cycle.

It will be appreciated that, at some point during use of biopsy device (100, 101), biopsy device (100, 101) may exhibit signs of being jammed with tissue or other debris. Such signs will be apparent to those of ordinary skill in the art in view of the teachings herein. During such times, or otherwise, it may be desirable to initiate a sequence that may clear such tissue or debris in order to improve the performance of biopsy device (100, 101). To that end, biopsy system (2) may permit a "clear probe" cycle to be initiated. A merely exemplary "clear probe" cycle will be described in detail below, while other variations of a "clear probe" cycle will be apparent to those of ordinary skill in the art in view of the teachings herein. FIG. 62 depicts an exemplary sequence of the position of cutter (50) within needle portion (10), relative to fluid communication being provided through tubes (402, 404), in an exemplary "clear probe" cycle.

If the "clear probe" cycle of the present example is initiated while biopsy system (2) is in a "view sample" mode as described above, manifold (144, 366) will be rotated move chamber (166, 388) from the three o'clock (or nine o'clock) position back to the twelve o'clock position. If biopsy system (2) is not in a "view sample" mode when the "clear probe" cycle of the present example is initiated, then manifold (144, 366) is not rotated. Next, cutter (50) retracts slightly to expose a portion of aperture (16) for a short period of time. During this period of exposure, air and/or saline (at atmospheric pressure) is communicated via tube (402). Also during this time, vacuum is provided through tube (404). Cutter (50) then advances to close aperture (16) without covering all of transverse openings (32). This same cycle is repeated additional times (e.g., one to four additional times, etc.) to complete the "clear probe" cycle. After the "clear probe" cycle is completed, biopsy system (2) enters a ready state. To the extent that a next "sample" cycle is not initiated within a certain amount of time (e.g., a few seconds, etc.), the "view sample" mode may be reactivated until the next "sample" cycle is initiated.

It will be appreciated that a "clear probe" cycle may be carried out in a variety of alternative ways. For instance, motion of cutter (50) may vary during the process of clearing a probe (102, 103). Furthermore, the timing of, sequence of, and interrelationships between lateral vacuum, axial vacuum, venting, and saline may be varied in a number of ways. Accordingly, the inventors contemplate a host of other permutations of such variables, and do not consider the invention to be limited in any way to the merely illustrative permutations explicitly discussed in detail above.

D. Exemplary "Position" Cycle

Figure 63:
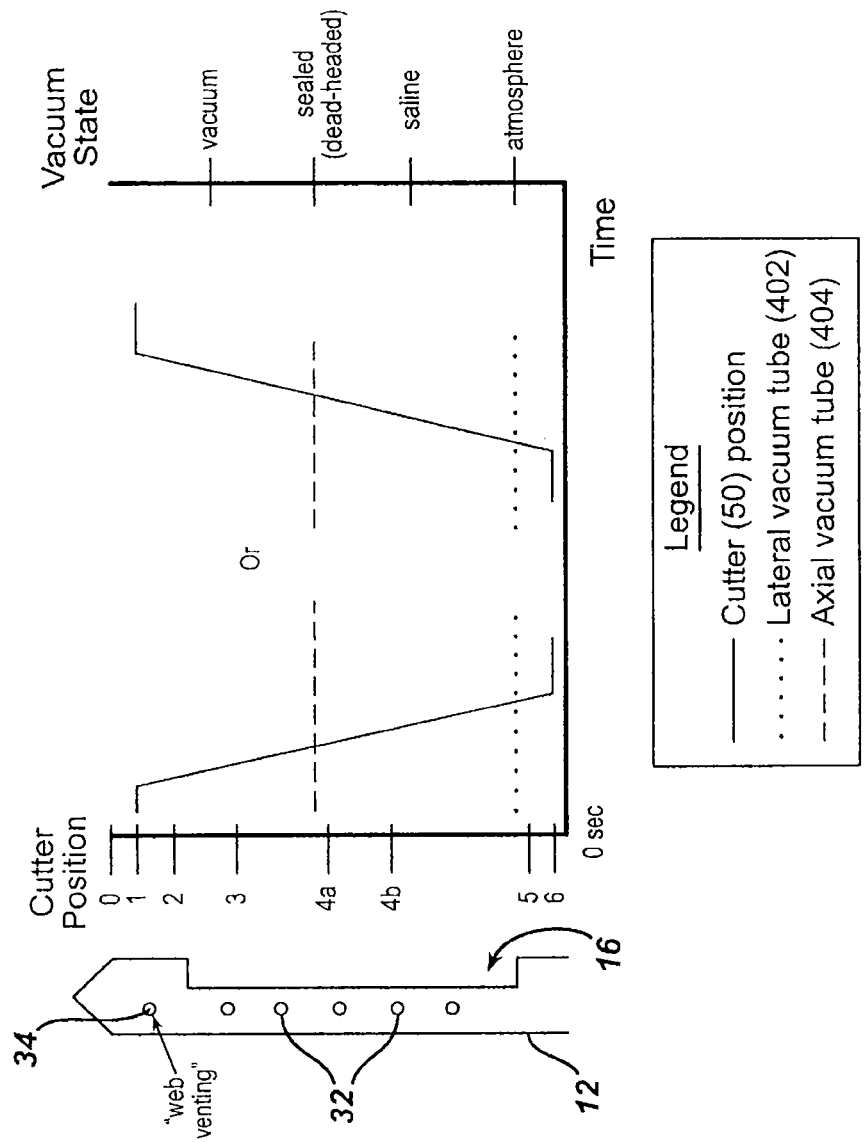
FIG. 63 depicts an exemplary sequence of the position of a cutter within a cannula, relative to fluid communication being provided through lateral and axial vacuum tubes, in an exemplary "position" cycle.

FIG. 63 depicts an exemplary sequence of the position of cutter (50) within needle portion (10), relative to fluid communication being provided through tubes (402, 404), in an exemplary "position" cycle. If a "position" cycle is initiated when aperture (16) is closed (e.g., when cutter (50) is advanced to a distal position) and when biopsy device (100, 101) is in a ready state, then cutter (50) is retracted proximally. During this time, tube (402) continues to be vented to atmosphere and tube (404) is sealed (a.k.a. dead-headed) by being pinched by tip (476).

A "position" cycle may be used in a variety of contexts. For instance, during an ultrasound guided procedure or other procedure, a needle (10) may be inserted into tissue with aperture (16) closed. To confirm the location of aperture (16) within the tissue, a "position" cycle may be initiated to open the aperture (16) to aid in visualizing the aperture (16). Once the aperture (16) location is confirmed, a "position" cycle may be initiated to close aperture (16). Another application of a "position" cycle may be when a marker is to be deployed into the tissue through cutter lumen (52) and into the tissue via aperture (16). In this context, a "position" cycle may be initiated to open aperture (16) to allow the tissue marker to be deployed into tissue via the open aperture (16). Other suitable uses for a "position" cycle will be apparent to those of ordinary skill in the art in view of the teachings herein.

If a "position" cycle is initiated when aperture (16) is open (e.g., when cutter (50) is retracted to a proximal position) and when biopsy device (100, 101) is in a ready state, then cutter (50) is advanced distally to close aperture (16). During this time, tube (402) continues to be vented to atmosphere and tube (404) is sealed (a.k.a. dead-headed) by being pinched by tip (476).

A variation of the "position" cycle may be used to vary the size of aperture (16) with cutter (50) in a manner such that aperture (16) will not open further than a preselected size during a "sample" cycle. For instance, it may be desirable to "shorten" the length of aperture (16) in order to acquire tissue samples (4) of a relatively shorter length, to acquire tissue samples (4) that are relatively close to the surface of a patient's skin, or for other purposes. Exemplary uses of cutter (50) position to vary the size of an aperture (16) during acquisition of tissues samples (4) are disclosed in U.S. Pub. No. 2006/0200040, entitled "Biopsy Device with Variable Side Aperture," published Sep. 7, 2006, the disclosure of which is incorporated by reference herein. As will be described in greater detail below, user interfaces (700, 800) may be used to variably select the degree to which aperture (16) may be opened during a "sample" cycle.

It will be appreciated that a "position" cycle may be carried out in a variety of alternative ways. For instance, motion of cutter (50) may vary during the process of positioning a cutter (50). Furthermore, the timing of, sequence of, and interrelationships between lateral vacuum, axial vacuum, venting, and saline may be varied in a number of ways. Accordingly, the inventors contemplate a host of other permutations of such variables, and do not consider the invention to be limited in any way to the merely illustrative permutations explicitly discussed in detail above.

E. Exemplary "Aspirate" Cycle

Figure 64:
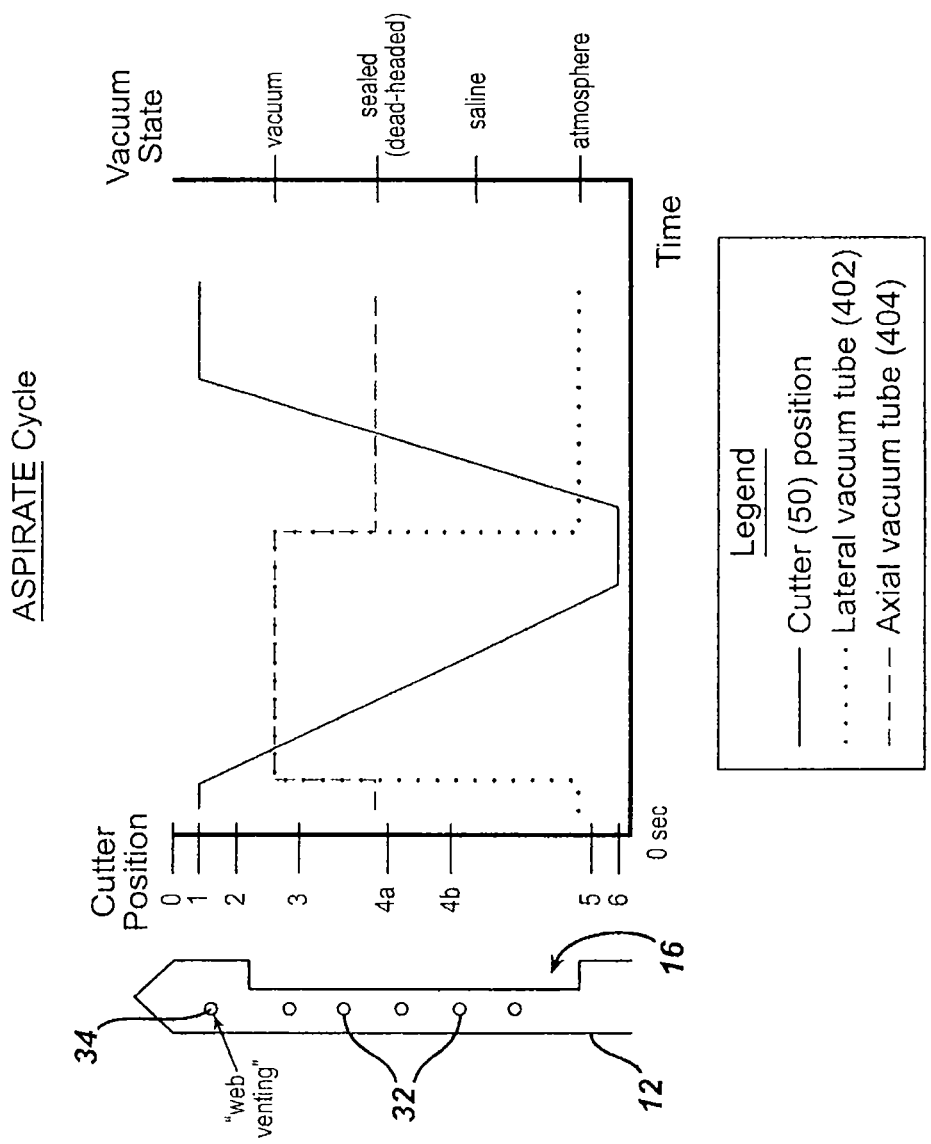
FIG. 64 depicts an exemplary sequence of the position of a cutter within a cannula, relative to fluid communication being provided through lateral and axial vacuum tubes, in an exemplary "aspirate" cycle.

It may be desirable to remove fluids from a biopsy site during a biopsy procedure. Accordingly, biopsy system (2) of the present example includes an "aspirate" cycle, which may be used to remove such fluids or for other purposes. FIG. 64 depicts an exemplary sequence of the position of cutter (50) within needle portion (10), relative to fluid communication being provided through tubes (402, 404), in an exemplary "aspirate" cycle.

If the "aspirate" cycle of the present example is initiated while biopsy system (2) is in a "view sample" mode as described above, manifold (144, 366) will be rotated move chamber (166, 388) from the three o'clock (or nine o'clock) position back to the twelve o'clock position. If biopsy system (2) is not in a "view sample" mode when the "aspirate" cycle of the present example is initiated, then manifold (144, 366) is not rotated. Next, as an aspirate button (not shown) is being actuated, or as some other user input is being provided, cutter (50) retracts until such actuation or input ceases. Thus, the longer the button is depressed or other input is provided, the more of aperture (15) is exposed by cutter (50). In addition, as the aspirate button is actuated or some other user input is provided, vacuum is provided through both of tubes (402, 404). Such vacuum is thus communicated axially through cutter lumen (52), and laterally (relative to cannula lumen (20)) through transverse openings (32). It will be appreciated that, with aperture (16) being at least partially open, vacuum provided through tubes (402, 404) may serve to draw fluids from the biopsy site. Such fluids will be deposited in vacuum canister (500) in the present example.

When the aspirate button is released, or similar user input ceases or changes, tube (402) may be switched from providing a lateral vacuum to providing a vent. In other words, solenoids (456) may be activated such that tip (478) substantially engages tube (402) to prevent further communication of a vacuum through tube (402), and such that tip (474) substantially disengages tube (410) to permit venting through tubes (410, 402). In addition, tube (404) is sealed (a.k.a. dead-headed) at this time, such as by tip (476) substantially engaging tube (404) to prevent further communication of a vacuum through tube (402). After a brief pause (e.g., a few seconds), cutter (50) is completely advanced distally, closing aperture (16) and covering transverse openings (32). Biopsy device (100, 101) is then again in a ready state.

If aperture (16) was open (e.g., cutter (50) at least partially retracted) when the "aspirate" cycle was initiated, then aperture (16) will remain open during the "aspirate" cycle, and vacuum is provided through tubes (402, 404) during the duration of the aspirate button being actuated (or during the duration of some other user input being provided). Once the aspirate button is released (or the other user input ceases or changes), then aperture (16) remains open, and biopsy device (100, 101) is again in a ready state. Accordingly, cutter (50) need not move during an "aspirate" cycle.

It will be appreciated that a "aspirate" cycle may be carried out in a variety of alternative ways. For instance, motion of cutter (50) may vary during the process of aspirating through a probe (102, 103). Furthermore, the timing of, sequence of, and interrelationships between lateral vacuum, axial vacuum, venting, and saline may be varied in a number of ways. Accordingly, the inventors contemplate a host of other permutations of such variables, and do not consider the invention to be limited in any way to the merely illustrative permutations explicitly discussed in detail above.

F. Exemplary "Smart Vac" Cycle

Figure 65:
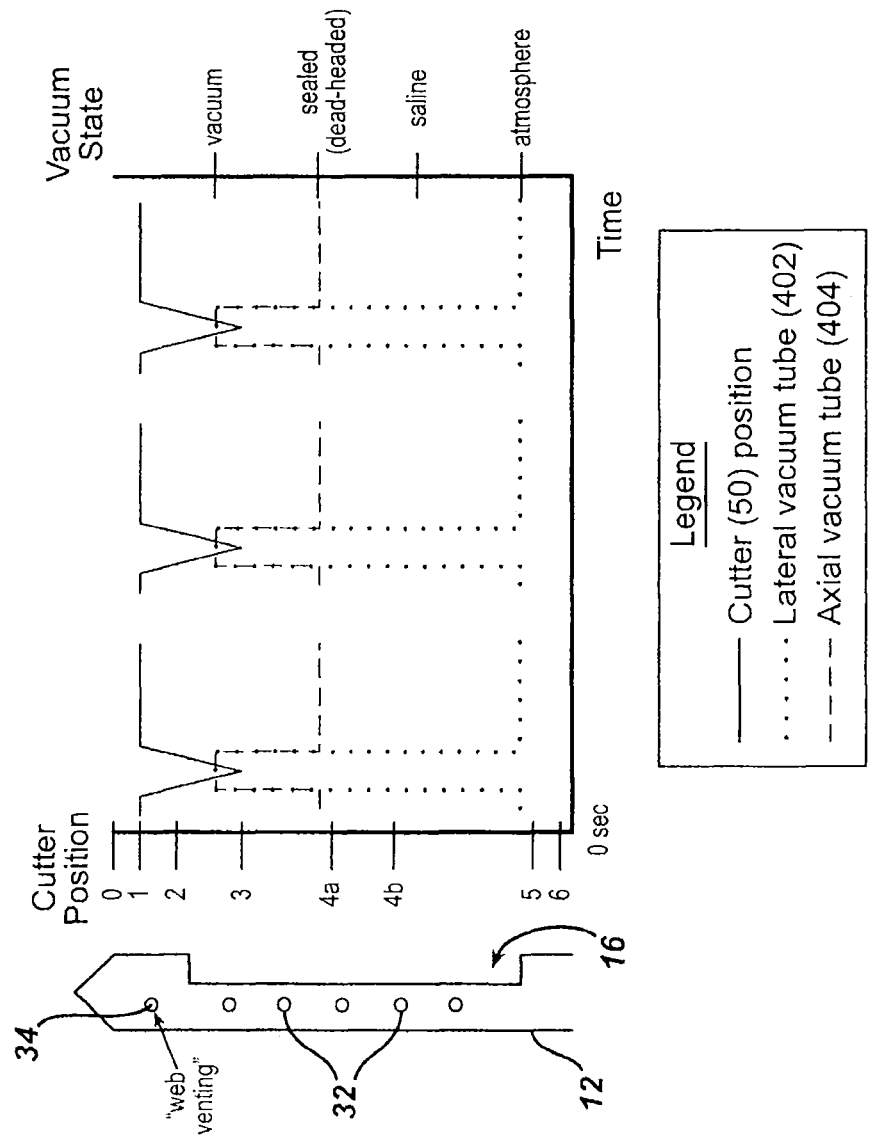
FIG. 65 depicts an exemplary sequence of the position of a cutter within a cannula, relative to fluid communication being provided through lateral and axial vacuum tubes, in an exemplary "smart vac" cycle.

There may be situations that arise during use of biopsy system (2) when needle portion (10) remains inserted in a patient's breast without tissue samples (4) being taken for a certain period of time. It may be desirable to remove fluids from a biopsy site during such periods. Accordingly, biopsy system (2) of the present example includes a "smart vac" cycle, which may be used to periodically remove such fluids during such periods or for other purposes. FIG. 65 depicts an exemplary sequence of the position of cutter (50) within needle portion (10), relative to fluid communication being provided through tubes (402, 404), in an exemplary "smart vac" cycle.

A "smart vac" cycle of the present example may be initiated when biopsy system (2) has been in a ready state for an extended period of time (e.g., one minute, thirty seconds, other periods of time, etc.) without any user inputs having been provided during such time. Such a period of dormancy may cause a "smart vac" cycle to be initiated automatically, whereby cutter (50) retracts slightly to expose a portion of aperture (16) during a short period of time (e.g., a few seconds). With cutter (50) slightly retracted, vacuum is applied through tubes (402, 404) to remove fluids from the biopsy site. Cutter (50) then automatically advances to close off aperture (16), and biopsy system (2) returns to a ready state. The "smart vac" cycle again automatically repeats if no further user inputs are provided within a certain period of time after the first "smart vac" cycle is completed. This process may be repeated indefinitely.

In an alternate embodiment, the level of vacuum may be lower during a "smart vac" cycle then it is during other operational cycles. Such a lower vacuum level may be provided in a variety of ways. For instance, tips (476, 478) may partially pinch tubes (402, 404) to restrict but not cut off fluid communication through tubes (402, 404). Alternatively, operation of vacuum pump (440) may be modified to adjust vacuum levels induced by vacuum pump (440). Other ways in which a vacuum level may be varied will be apparent to those of ordinary skill in the art in view of the teachings herein.

It will be appreciated that a "smart vac" cycle may be carried out in a variety of alternative ways. For instance, motion of cutter (50) may vary during the process of removing fluids from a biopsy site. Furthermore, the timing of, sequence of, and interrelationships between lateral vacuum, axial vacuum, venting, and saline may be varied in a number of ways. Accordingly, the inventors contemplate a host of other permutations of such variables, and do not consider the invention to be limited in any way to the merely illustrative permutations explicitly discussed in detail above.

VII. Exemplary User Interface on Vacuum Control Module

As discussed above, display screen (702), switches (704), and speaker (706) may be regarded as collectively forming user interface (700). In addition, as also discussed above, face portion (420) is configured such that display screen (702) can be viewed therethrough; such that capacitive switches (704) may be activated therethrough; and such that sounds coming from the speaker (706) can be heard therethrough. Capacitive switches (704) are configured such that switches (704) are activated when a user's finger comes in close enough proximity to switches (704). In particular, a capacitive switch (704) may generate an electrical field, such that the approaching finger of a user may cause a disturbance in the electrical field that may be detected by the approached switch (704). Capacitive switches (704) may have sufficient sensitivity such that a user need not even touch face portion (420) in order to activate a capacitive switch (704). In other words, capacitive switches (704) may be configured such that a user's finger need only reach certain distance from face portion (420) over capacitive switches (704) in order to activate switches (704). Of course, any other suitable "touch-free" technology (e.g., ultrawideband radar, etc.) may be used in lieu of or in addition to capacitive switches (704). Alternatively, other input devices (e.g., conventional buttons, switches, sliders, dials, etc.) may be used.

Capacitive switches (704) of the present example are supplemented with LEDs (not shown). In particular, an LED is positioned with respect to each capacitive switch (704) to provide visual feedback when the associated capacitive switch (704) is sufficiently activated by a user. For instance, an LED associated with each capacitive switch (704) may remain lit by default, and may switch to unlit when its associated capacitive switch (704) has been sufficiently activated. Alternatively, an LED associated with each capacitive switch (704) may remain unlit by default, and may switch to lit when its associated capacitive switch (704) has been sufficiently activated. An LED may also be used to provide visual feedback as to the state of vacuum control module (400). For instance, a status LED may stay constantly lit as vacuum control module (400) is running, and may pulse (e.g., ebb and intensify) when vacuum control module (400) is in a "sleep mode" (e.g., powered-on but not being actively used). Other ways in which LEDs or other light sources or visual indicators may be incorporated into vacuum control module, either in conjunction with capacitive switches (704) or otherwise, will be apparent to those of ordinary skill in the art in view of the teachings herein.

In addition, speaker (706) may emit auditory tones to reinforce feedback associated with use of vacuum control module (400). For instance, speaker (706) may emit a tone when a capacitive switch (704) has been activated. In addition, certain switches (704) may have certain tones or auditory patterns associated with them. Similarly, certain selections made by a user activating switches (704), such as the selections and operations described in greater detail below, may each have a distinct, associated tone or auditory pattern. Of course, auditory tones or patterns, or other uses for speaker (706), may be incorporated into vacuum control module (400) and use of the same in a variety of alternative ways.

Figure 66:
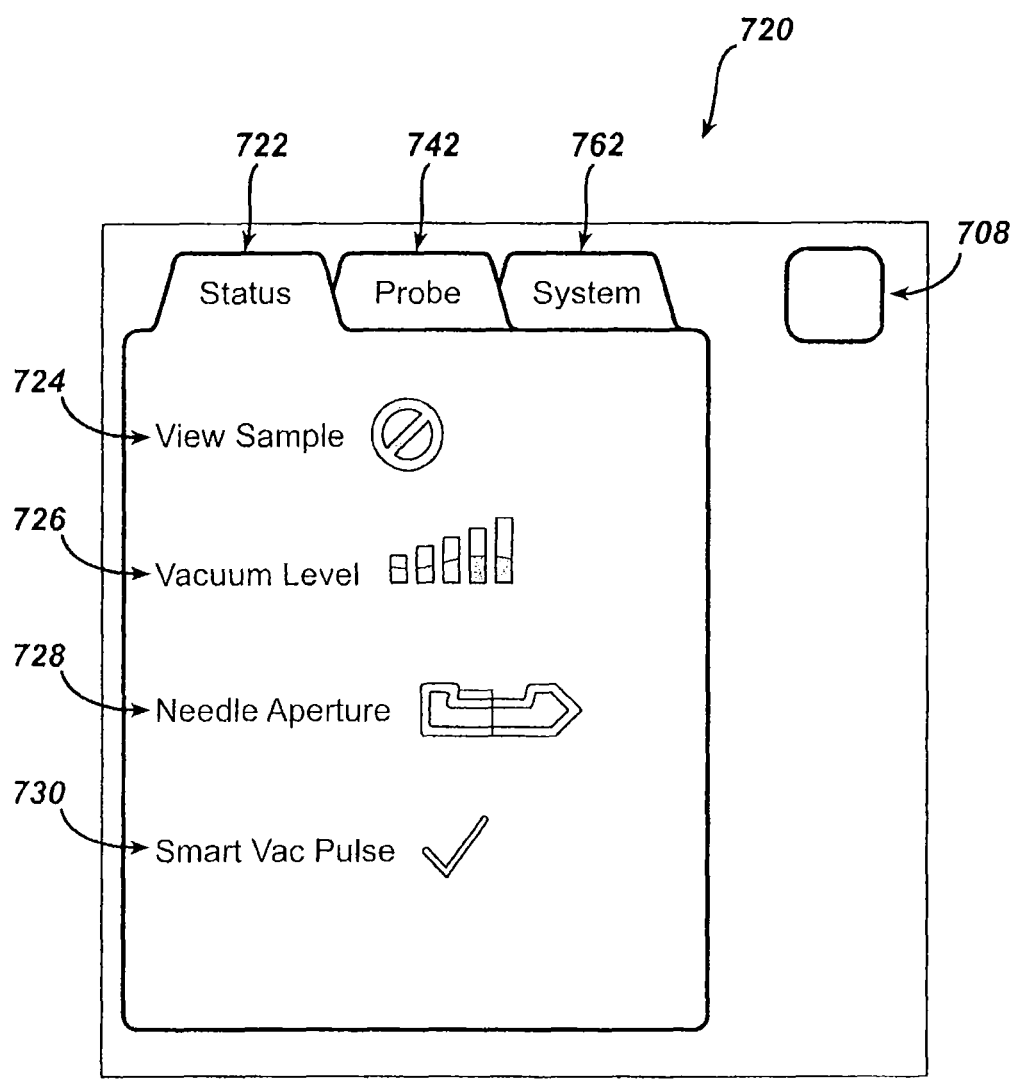
FIG. 66 depicts an exemplary "status" page of an exemplary user interface for a biopsy system.
Figure 67:
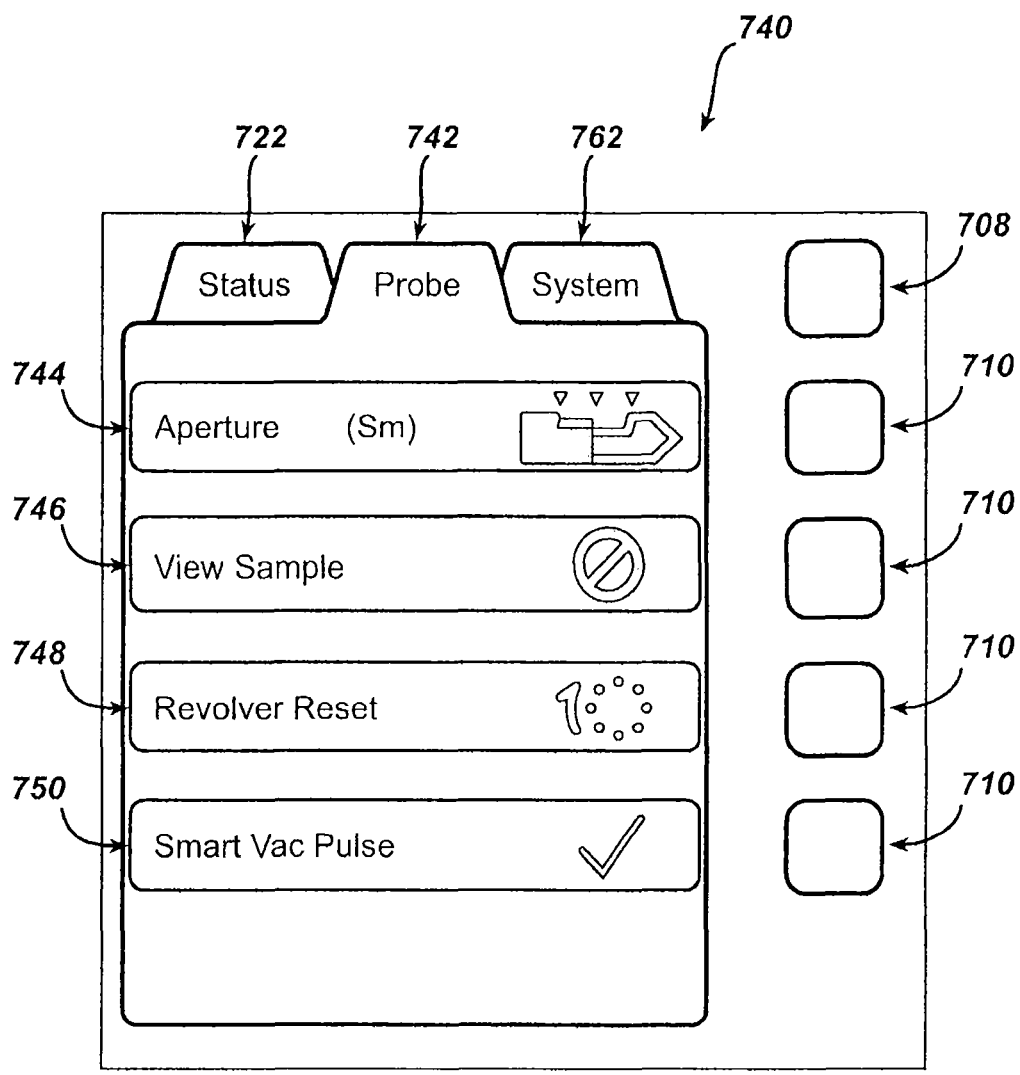
FIG. 67 depicts an exemplary "probe" page of an exemplary user interface for a biopsy system.
Figure 68:
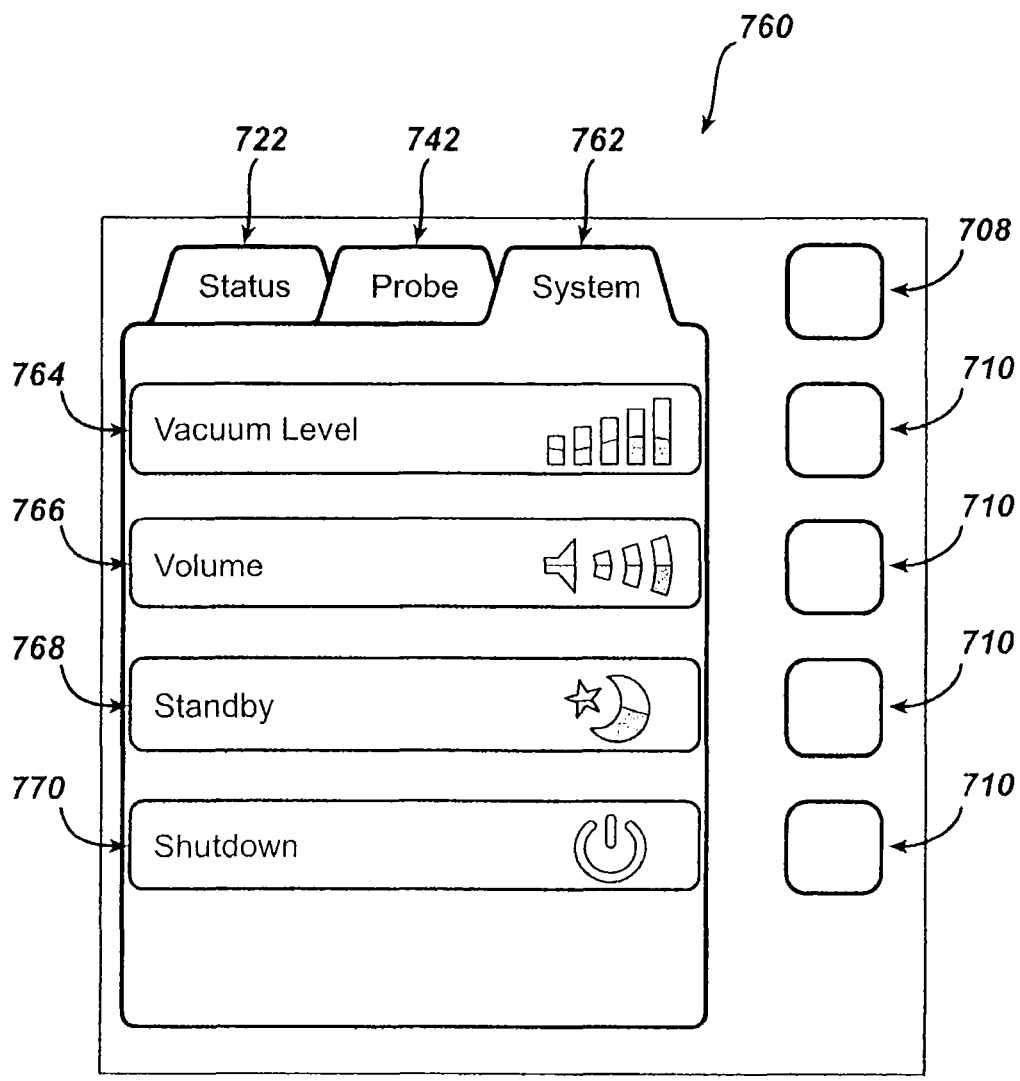
FIG. 68 depicts an exemplary "system" page of an exemplary user interface for a biopsy system.

Other aspects of user interface (700) are shown in FIGS. 66-68. In particular, FIGS. 66-68 show a variety of exemplary screens (720, 740, 760) that may be displayed on display screen (702). Each of these merely exemplary screens (720, 740, 760) will be described in greater detail below. In one embodiment, face portion (420) and display screen (702) configured such that the perimeter of display screen (702) cannot be seen through face portion (420). Furthermore, face portion (420) does not provide any definition for a perimeter associated with display screen (702). Thus, text, icons, and other visual indicia displayed on display screen (702) appears to "float" on the face of vacuum control module (400). Of course, such a configuration is merely optional.

As is also shown in FIGS. 66-68, capacitive switches (704) are visually presented as buttons (708, 710), which are vertically aligned adjacent to screens (720, 740, 760). Buttons (708, 710) include a top button (708), which is used to cycle between the various screens (720, 740, 760); and lower buttons (710), which are used to provide input selections relative to an active screen (720, 740, 760). In particular, each time top button (708) is activated, such activation causes display screen (702) to change from one screen (720, 740, 760) being active to the next screen (720, 740, 760) being active.

Each screen (720, 740, 760) has a corresponding tab (722, 740, 762) associated therewith. In particular, a "Status" tab (722) is associated with a status screen (720), a "Probe" tab (742) is associated with a probe screen (740), and a "System" tab (762) is associated with a system screen (760). Tabs (722, 740, 762) are arranged at the top of each corresponding screen (720, 740, 760), and the tabs (722, 740, 762) of other screens (720, 740, 760) can still be seen when a given screen (720, 740, 760) is active. For instance, in FIG. 66, the status screen (720) is active, yet the "Probe" tab (742) and "System" tab (762) may still be seen. However, the "Status" tab (722) is more brightly lit than the "Probe" tab (742) and "System" tab (762) in FIG. 66. In FIG. 67, the probe screen (740) is active; while in FIG. 68, the system screen (762) is active. It will be appreciated by those of ordinary skill in the art in view of the teachings herein that tabs (722, 740, 762) are merely exemplary, and that tabs (722, 740, 762) may be incorporated into a user interface (700) in a variety of alternative ways. In addition, there are a variety of alternative features that may be used in addition to or in lieu of tabs (722, 740, 762).

A. Exemplary "Status" Screen

Referring back to FIG. 66, a merely exemplary status screen (720) includes several visual indicators (724, 726, 728, 730). For instance, a "view sample" indicator (724) indicates whether biopsy system (2) is in "view sample" mode, examples of which are described in greater detail above. As shown, the "view sample" indicator (724) of this example includes an icon shown as a circle with a slash to indicate that the "view sample" mode is turned off. A checkmark or other indication may be used to indicate when the "view sample" mode is turned on. A user may turn the "view sample" mode on or off when the probe screen (740) is active, as will be described in greater detail below. Of course, other suitable visual indicators may be used in addition to or in lieu of the circle with a slash and/or checkmark to indicate the status of the "view sample" mode.

A "vacuum level" indicator (726) is also provided on status screen (720). As shown, the "vacuum level" indicator (726) of this example includes an icon shown as a set of ascending bars, to indicate the vacuum level of biopsy system (2). A user may adjust the vacuum level of biopsy system (2) when the system screen (760) is active, as will be described in greater detail below. Incremental increases in the vacuum level are indicated in this example by the illumination of an additional bar in the set of ascending bars of "vacuum level" indicator (726). In other words, the number of bars that are illuminated in "vacuum level" indicator (726) will be indicative of the vacuum level of biopsy system (2). Of course, any other suitable visual indicators (e.g., a simulated needle gauge, a number, etc.) may be used in addition to or in lieu of ascending bars to indicate the level of vacuum within biopsy system (2).

A "needle aperture" indicator (728) is also provided on status screen (720). As shown, the "needle aperture" indicator (726) of this example includes an icon shown as a needle end with a brightly lit cutter. This "needle aperture" indicator (726) may be used to indicate the maximum distance to which cutter (50) will be retracted within needle portion (10) during use of biopsy system (2). For instance, as noted above in the context of a "position" cycle, a user may wish to restrict proximal movement of cutter (50) to restrict the degree to which aperture (16) will be opened within a breast. Such use of a cutter (50) to vary the aperture (16) opening for a biopsy procedure is described in U.S. Pub. No. 2006/0200040, entitled "Biopsy Device with Variable Side Aperture," published Sep. 7, 2006, the disclosure of which is incorporated by reference herein. A user may adjust this effective needle aperture (16) when the probe screen (740) is active, as will be described in greater detail below. The position of the cutter portion of the icon in the "needle aperture" indicator (726) relative to the needle portion of the icon in the "needle aperture" indicator (726) may be indicative of the effective needle aperture (16) set by a user. Of course, any other suitable visual indicators may be used in addition to or in lieu of a rendering of a needle and cutter end to indicate the effective needle aperture set by a user.

A "smart vac pulse" indicator (730) is also provided on status screen (720), to indicate whether biopsy system (2) is in "smart vac" mode as described in greater detail above. As shown, the "smart vac pulse" indicator (730) of this example includes an icon shown as checkmark to indicate that the "smart vac pulse" mode is turned on. A circle with a slash or other indication may be used to indicate when the "smart vac pulse" mode is turned off. A user may turn the "smart vac" mode on or off when the probe screen (740) is active, as will be described in greater detail below. Of course, other suitable visual indicators may be used in addition to or in lieu of the circle with a slash and/or checkmark to indicate the status of the "smart vac" mode.

In view of the foregoing, status screen (720) of the present example is used merely to indicate the status of several variables within biopsy system (2). Status screen (720) of this particular example is not configured to accept user inputs to change any of these variables or otherwise alter the operation of biopsy system (2). Buttons (710) are not active when status screen (720) is active. In order to change any of the variables, a user must activate top button (708) in status screen (720) in order to switch active screens from status screen (720) to probe screen (740) or system screen (760), where the user may then provide inputs to change variables. In other embodiments, however, a status screen (720) may permit a user to change some or all variables whose status is indicated on status screen (720). Other ways in which a status screen (720) or other screen may be provided will be apparent to those of ordinary skill in the art in view of the teachings herein. In addition, in some embodiments, a status screen (720) is simply omitted altogether (e.g., such that only a probe screen (740) and system screen (760) and/or other screens are used, etc.).

B. Exemplary "Probe" Screen

Referring back to FIG. 67, a merely exemplary probe screen (740) includes several visual indicators (744, 746, 748, 750). For instance, an "aperture" indicator (742) indicates the maximum distance to which cutter (50) will be retracted within needle portion (10) during use of biopsy system (2). For instance, as noted above, a user may wish to restrict proximal movement of cutter (50) to restrict the degree to which aperture (16) will be opened within a breast. A user may adjust this effective needle aperture (16) by activating the button (710) that is next to the "aperture" indicator (742). Each time the user activates this button (710), biopsy system (2) will make a corresponding adjustment to the effective needle aperture (16), such as through controller (480). Such adjustments may be incremental, such as to provide an aperture (16) that is 50%, 75%, or 100% open, though other increments may be used. In addition, each time the user activates this button (710), the cutter portion of the icon in the "aperture" indicator (742) moves relative to the needle portion of the icon in the "aperture" indicator (742). Arrows are also shown above the needle portion of the icon to emphasize the maximum proximal position of the needle selected by the user. Furthermore, a text representation (e.g., "Sm" for small aperture (16), "Lg" for large aperture, etc.) may be included to further indicate the effective aperture (16) size selected by the user.

It will be appreciated in view of the teachings herein that "aperture" indicator (742) on probe screen (740) is similar to "needle aperture" indicator (728) on status screen (720), except that "aperture" indicator (742) on probe screen (740) provides additional information on the effective aperture (16) length selected by the user. Furthermore, unlike status screen (720) in the present example, probe screen (740) permits the user to adjust the effective aperture (16) length by activating the button (710) that is next to "aperture" indicator (742). Each activation of button (710) by the user may result in an incrementally decreased effective aperture (16) length, until the length reaches zero, at which time a subsequent activation of button (710) may result in the length "flipping back" to the full aperture (16) length. As an alternative to permitting incremental changes in effective aperture (16) length, user interface (700) may permit a user to gradually change the effective aperture (16) length, such as by using a slider, dial, knob, etc., including by use of touch-sensitive virtual representations (e.g., on a touch-sensitive screen) of such input devices. Other ways in which a user may be permitted to adjust effective aperture (16) length will be apparent to those of ordinary skill in the art in view of the teachings herein. In addition, any other suitable visual indicators may be used in addition to or in lieu of a rendering of a needle and cutter end to indicate the effective needle aperture set by a user.

Probe screen (740) of the present example also includes a "view sample" indicator (746), which indicates whether biopsy system (2) is in "view sample" mode as described above. As shown, the "view sample" indicator (746) of this example includes an icon shown as a circle with a slash to indicate that the "view sample" mode is turned off. To turn the "view sample" mode on, the user may activate the button (710) next to the "view sample" indicator (746). A checkmark or other icon or indicator may replace the circle with a slash to indicate that the "view sample" mode has been turned on. To turn the "view sample" mode back off, the user may activate the button (710) next to the "view sample" indicator (746) again.

It will be appreciated in view of the teachings herein that "view sample" indicator (746) on probe screen (740) is similar to "view sample" indicator (724) on status screen (720), except that probe screen (740) permits the user to turn the "view sample" mode on and off by activating the button (710) that is next to "view sample" indicator (746). Of course, other suitable visual indicators may be used in addition to or in lieu of the circle with a slash and/or checkmark to indicate the status of the "view sample" mode.

Probe screen (740) of the present example also includes a "revolver reset" indicator (748), which indicates that the button (710) that is next to the "revolver reset" indicator (748) may be activated to reset the manifold (144, 366) position. In particular, as noted above, encoder wheel (292) and sensor (296) are used in some embodiments to track the rotational position of manifold (144, 366) during use of biopsy device (100, 101). When a user has replaced manifold (144, 366), such that the last chamber (166, 388) that biopsy system (2) "thinks" is aligned with cutter lumen (52) is no longer aligned with cutter lumen (52), the user may activate the button (710) that is next to the "revolver reset" indicator (748) to indicate to biopsy system (2) that a new manifold (144, 366) has been coupled with probe (102, 103). Biopsy system (2) will then "assume" that the predefined chamber (166, 388), or the passage (158) is aligned with cutter lumen (52). The button (710) that is next to the "revolver reset" indicator (748) may also be activated under other conditions, such as when a user has manually rotated manifold (144, 366) to align the predefined chamber (166, 388) with cutter lumen (52).

Probe screen (740) of the present example also includes a "smart vac pulse" indicator (750), which indicates whether biopsy system (2) is in "smart vac" mode as described in greater detail above. As shown, the "smart vac pulse" indicator (750) of this example includes an icon shown as checkmark to indicate that the "smart vac pulse" mode is turned on. A circle with a slash or other indication may be used to indicate when the "smart vac pulse" mode is turned off. To turn the "smart vac" mode off, the user may activate the button (710) next to the "smart vac pulse" indicator (750). A circle with a slash or other icon or indicator may replace the checkmark to indicate that the "smart vac" mode has been turned off. To turn the "smart vac" mode back on, the user may activate the button (710) next to the "smart vac pulse" indicator (750) again.

It will be appreciated in view of the teachings herein that "smart vac pulse" indicator (750) on probe screen (740) is similar to "smart vac pulse" indicator (730) on status screen (720), except that probe screen (740) permits the user to turn the "smart vac" mode on and off by activating the button (710) that is next to "smart vac pulse" indicator (750). Of course, other suitable visual indicators may be used in addition to or in lieu of the circle with a slash and/or checkmark to indicate the status of the "smart vac" mode.

C. Exemplary "System" Screen

Referring back to FIG. 68, a merely exemplary system screen (760) includes several visual indicators (764, 766, 768, 770). For instance, a "vacuum level" indicator (764) is provided on system screen (760). As shown, the "vacuum level" indicator (764) of this example includes an icon shown as a set of ascending bars, to indicate the vacuum level of biopsy system (2). To adjust the vacuum level of biopsy system (2), the user may activate the button (710) next to the "vacuum level" indicator (764). Each time the user activates this button (710), the vacuum level of biopsy system (2) may increase incrementally. Such incremental increase may be indicated by illuminating an additional bar in the set of ascending bars of "vacuum level" indicator (764). In other words, the number of bars that are illuminated in "vacuum level" indicator (764) will be indicative of the vacuum level of biopsy system (2).

If the user activates the associated button (710) when all of the bars are illuminated (e.g., which may indicate that the vacuum level is at its highest), the level of vacuum may be significantly decreased to the lowest level, such that only the first bar in the set of bars is illuminated. Thus, a user may cycle through various incremental vacuum levels by repeatedly activating the button (710) that is next to the "vacuum level" indicator (764), and these incremental changes in the vacuum level may be indicated in the set of ascending bars of the "vacuum level" indicator (764).

It will be appreciated that control of vacuum level, as selected by a user via the system screen (760), may be effected in a variety of ways. For instance, the selected vacuum level may be effected by changing the operation of vacuum pump (440). Alternatively, the selected vacuum level may be effected by changing the degree to which tips (476, 478) disengage tubes (402, 404) when a vacuum is to be applied through tubes (402, 404). For instance, solenoids (456) may be activated to release tips (476, 478) from tubes only slightly, such that tips (476, 478) create a restriction in tubes (402, 404) without preventing a vacuum from being communicated through tubes (402, 404). In another variation, an additional valve (not shown) or other component at any suitable location is used to vary the vacuum level in accordance with a user's selections.

It will be appreciated in view of the teachings herein that "vacuum level" indicator (764) on system screen (760) is similar to "vacuum level" indicator (764) on status screen (720), except that system screen (760) permits the user to change the vacuum level of biopsy system (2) by activating the button (710) that is next to "vacuum level" indicator (764). Of course, any other suitable visual indicators (e.g., a simulated needle gauge, a number, etc.) may be used in addition to or in lieu of ascending bars to indicate the level of vacuum within biopsy system (2).

System screen (760) of the present example also includes a "volume" indicator (766). As shown, the "volume" indicator (766) of this example includes an icon shown as a speaker and a set of bars that increase in size, to indicate the volume level of tones that will be emitted by speaker (706). To adjust the volume, the user may activate the button (710) that is next to the "volume" indicator (766). Each time the user activates this button (710), the volume may increase incrementally. Such incremental increase may be indicated by illuminating an additional bar in the set of ascending bars of "volume" indicator (766). In other words, the number of bars that are illuminated in "volume" indicator (766) will be indicative of the volume of tones or other sounds that will be emitted by speaker (706). "Volume" indicator (766) and its associated button (710) are thus similar to "vacuum level" indicator (764) and its associated button (710) as described above, with the exception that the former are associated with volume levels while the latter are associated with vacuum levels. Of course, any other suitable visual indicators (e.g., a simulated dial, a number, etc.) may be used in addition to or in lieu of a speaker and bars that increase in size to indicate the volume level.

System screen (760) of the present example also includes a "standby" indicator (768). As shown, the "standby" indicator (768) of this example includes an icon shown as a star and a moon. To put biopsy system (2) in a standby mode, the user may activate the button (710) that is next to the "standby" indicator (768). In one version of standby mode, vacuum pump (440) is turned off, and at least some user input devices are deactivated (e.g., user interface (800) on holster (202, 302), a footswitch, etc.). Other variations of a standby mode will be apparent to those of ordinary skill in the art in view of the teachings herein. In order to bring biopsy system (2) out of standby mode, a user may simply activate any capacitive switch (704) at user interface (700), activate any switch or button on holster (202, 302), or perform some other action.

System screen (760) of the present example also includes a "shutdown" indicator (770). As shown, the "shutdown" indicator (770) of this example includes an icon representative of a power button. To shut biopsy system (2) down, the user may activate the button (710) that is next to the "shutdown" indicator (770). Of course, there are a variety of other ways in which a user may be permitted to shut biopsy system (2) down.

While not shown in the accompanying drawings, it will be appreciated that display screen (702) may display a variety of other displays not explicitly described above. By way of example only, when cable (484) is not connected to port (482), display screen (702) may display a message instructing the user to connect cable (484). Similarly, when vacuum canister (500) is not inserted into canister compartment (458), or if a satisfactory seal is not obtained between vacuum ports (462, 514), display screen (702) may display a message instructing the user to properly insert vacuum canister (500) into canister compartment (458).

VIII. Exemplary User Interface on Holster

In addition to or in lieu of a user interface (700) being provided by a vacuum control module (400), a user interface (800) may be provided on biopsy device (100, 101). For instance, such a user interface (800) may be provided on a probe (102, 103) and/or on a holster (202, 302). In the present example, a merely exemplary user interface (800) is provided on holster (202). Also in the present example, controls provided through user interface (700) of vacuum control module (400) relate more to settings of biopsy system (2), while controls provided through user interface (800) of holster (202) relate more to actual operation of biopsy device (100). It will be appreciated, however, that such roles may be reversed or mixed. For instance, user interface (800) may be configured to permit a user to adjust at least some settings of biopsy system (2), and/or user interface (700) may be configured to permit a user operate biopsy device (100).

Figure 69:
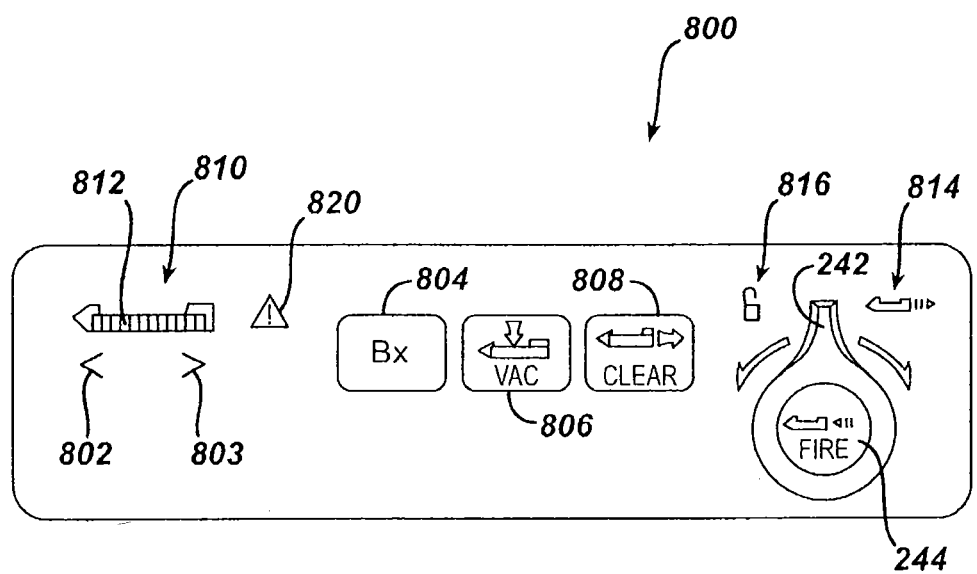
FIG. 69 depicts an exemplary user interface that may be applied to a portion of a biopsy device.

Referring to FIG. 69, user interface (800) of the present example is provided as a membrane that is securable to either or both of side panels (214, 216). User interface (800) may also be provided, at least in part, as an in-mold decoration (IMD). Such an IMD configuration may provide a seal of holster (202), such that the presence of user interface (800) does not create undesirable leak points. An IMD configuration may nevertheless provide flexible areas for user input, such as buttons (802, 803, 804, 806, 808) described below. In other embodiments, user interface (800) is provided, at least in part, through a double shot molding process. Other ways in which a user interface (800) may be provided will be apparent to those of ordinary skill in the art in view of the teachings herein.

User interface (800) of the present example comprises five buttons (802, 803, 804, 806, 808), each of which will be described in greater detail below, though any other suitable number of buttons may be used. In some embodiments, buttons (802, 803, 804, 806, 808) are provided as thin film switches as part of the membrane. In other embodiments, buttons (802, 803, 804, 806, 808) are formed in the side panel (214, 216) to which the membrane is adhered. In still other embodiments, buttons (802, 803, 804, 806, 808) comprise capacitive switches. In the present example, buttons (802, 803, 804, 806, 808) (or at least a perimeter of buttons (802, 803, 804, 806, 808)) are lit by LEDs or other sources of light behind a membrane. Other ways in which buttons (802, 803, 804, 806, 808) may be provided will be apparent to those of ordinary skill in the art in view of the teachings herein.

Buttons (802, 803) of the present example may be actuated to advance or retract cutter (50), respectively. Such advancement or retraction may be used to selectively reduce the effective aperture (16) size, as noted above, during a sampling cycle. Alternatively, a user may wish to vary aperture size (16) while aspirating. Other situations in which a user may wish to advance or retract cutter (50) by activating buttons (802, 803) will be apparent to those of ordinary skill in the art in view of the teachings herein. As will be described in greater detail below, the cutter (50)

position obtained through a user's activation of buttons (802, 803) may be indicated through the discrete lighted sections (812) of a cutter position indicator (810) on user interface (800).

Button (804) of the present example is operable to initiate a sampling cycle. Exemplary sampling cycles are discussed above in detail, and will therefore not be described in greater detail here. Suitable ways in which a button (804) may be made operable to initiate a sampling cycle will be apparent to those of ordinary skill in the art in view of the teachings herein. Furthermore, in some variations, button (804) also performs the same function of button (802) as described above, such that button (802) may be omitted. Similarly, in other variations, button (802) performs the same function as button (804) as described above, such that button (804) may be omitted.

Button (806) of the present example is operable to initiate a lateral vacuum within probe (102). For instance, actuation of button (806) may result in a vacuum being communicated through tube (402), which may in turn be communicated through transverse openings (32). Suitable ways in which a button (806) may be made operable to initiate a lateral vacuum will be apparent to those of ordinary skill in the art in view of the teachings herein.

Button (808) of the present example is operable to initiate a clear probe cycle. Exemplary clear probe cycles are discussed above in detail, and will therefore not be described in greater detail here. Suitable ways in which a button (808) may be made operable to initiate a clear probe cycle will be apparent to those of ordinary skill in the art in view of the teachings herein.

User interface (800) also includes a cutter position indicator (810), which includes a representation of the distal end of outer cannula (12) and a plurality of discrete lighted sections (812). By way of example only, one or more LEDs or other sources of light may be used to illuminate discrete sections (812). The lighting of discrete sections (812) may serve to indicate the position of cutter (50) relative to aperture (16). For instance, the last lit discrete section (812) may indicate the distal end of cutter (50). In some embodiments, only those discrete sections (812) corresponding to cutter (50) position are lit, while the remaining discrete sections (812) are unlit. In other embodiments, those discrete sections (812) corresponding to cutter (50) position are lit with one color (e.g., red), while the remaining discrete sections (812) are lit with another color (e.g., yellow). Still other ways in which a cutter position indicator (810) may be used to indicate the position of cutter (50) will be apparent to those of ordinary skill in the art in view of the teachings herein. In addition, there are a variety of ways in which cutter (50) position data may be effectively communicated to cutter position indicator (810). By way of example only, one or more sensors may be communicatively coupled with cutter (50), cutter rotation and translation mechanism (120), and/or cutter drive mechanism (270).

User interface (800) also includes an icon (814) indicating an needle cocking direction for trigger (242), as well as an icon (816) indicating an unlocking direction for trigger (242). Ways in which trigger (242) may be used to cock and fire (e.g., in conjunction with actuation of button (244)) needle portion (10) are described in greater detail above. Icons (814, 816) may simply provide visual indications of the directions for rotating trigger (242) to accomplish such actions.

In addition, user interface (800) includes an error light (820). Error light (820) may be selectively lit under a variety of conditions. For instance, error light (820) may be lit when a tissue is jammed in cutter lumen (52) or elsewhere within biopsy system (2). Error light (820) may also provide "trouble codes" by flashing in a particular sequence or pattern that is associated with a particular condition. For instance, the number of times error light (820) flashes before repeating a flashing sequence may be varied based on error conditions. It will also be appreciated that other components of user interface (800) may be used to communicate one or more error conditions, in lieu of or in addition to error light (820). For instance, discrete sections (812) of cutter position indicator (810) may flash or be selectively lit in certain patterns or sequences to indicate certain error conditions. Other ways in which error conditions may be communicated to a user, via lights or otherwise, will be apparent to those of ordinary skill in the art in view of the teachings herein. Similarly, ways in which error conditions may be detected will be apparent to those of ordinary skill in the art in view of the teachings herein.

In versions where both sides of a holster (202, 302) have buttons (802, 803, 804, 806, 808), biopsy system (2) may be configured to assign the first side on which a button (802, 803, 804, 806, 808) is activated as the "active" side of the holster (202, 302). Similarly, biopsy system (2) may assign the first side on which a trigger (242) or button (244) s activated as the "active" side of the holster (202, 302). By way of example only, in versions providing a "view sample" mode as described above, such an assignment of an "active" side may dictate whether recently acquired tissue samples (4) are presented at a three o'clock position or at a nine o'clock position. In other words, if a user first activates a button (244, 802, 803, 804, 806, 808) or trigger (242) on a side corresponding to the three o'clock position of tissue sample holder (140, 368), manifold (144, 366) may rotate to present a recently acquired tissue sample (4) to the user at a three o'clock position. Alternatively, biopsy system (2) may be configured to vary other functions in response to an assignment of an "active" side, or may simply not assign an "active" side at all.

It will be appreciated that a variety of components may be used to give effect to buttons (802, 803, 804, 806, 808), lighted sections (812), and error light (820). For instance, one or more printed circuit boards (not shown) may be provided within holster (202). In addition, user interface (800) may be at least partially in communication with vacuum control module (400), such as via cable (484) or otherwise. Other ways in which user interface (800) may be incorporated into biopsy system (2), as well as other variations of user interface (800), will be apparent to those of ordinary skill in the art in view of the teachings herein.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed an sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A biopsy system operable to obtain severed tissue samples from a tissue mass, the biopsy system comprising:
    (a) a biopsy device including a needle portion insertable in the tissue mass, a cutter movable with respect to needle to sever a tissue sample from tissue received by the needle portion, and a tissue sample holder for receiving tissue samples severed by the cutter; and
    (b) a user interface providing a cutter position indicator configured to depict a position of the cutter relative to the needle portion, a first adjustment feature configured to adjust the position of the cutter relative to the needle portion between one of a plurality of predetermined aperture positions to variably select an effective aperture size, a vacuum level indicator configured to graphically depict a selected level of vacuum provided from a vacuum source to the biopsy device among at least three levels of vacuum provided from a vacuum source to the biopsy device, and a second adjustment feature configured to adjust the selected level of vacuum,
    the user interface further providing a graphical button, the graphical button being configured to be in a continuous position through operation of the user interface and being further configured to activate the first adjustment feature and the second adjustment feature for adjustment of both the position of the cutter relative to the needle and the selected level of vacuum provided to the biopsy device.

2. The biopsy system of claim 1, wherein the user interface further provides a plurality of different user selectable operational modes of the biopsy device, wherein the user interface is in communication with the biopsy device to manipulate the biopsy device through the plurality of different user selectable operational modes, wherein at least one of the user selectable operational modes of the biopsy device includes a sample mode, and wherein at least one of the user selectable operational modes is a non-sampling mode, wherein one of the user selectable operational modes includes a clear probe mode.

3. The biopsy system of claim 1, wherein the user interface further provides a plurality of different user selectable operational modes of the biopsy device, wherein the user interface is in communication with the biopsy device to manipulate the biopsy device through the plurality of different user selectable operational modes, wherein at least one of the user selectable operational modes of the biopsy device includes a sample mode, and wherein at least one of the user selectable operational modes is a non-sampling mode, wherein one of the user selectable operational modes includes a view operational mode to provide viewing of a sample stored in the tissue sample holder.

4. The biopsy system of claim 3, wherein the user interface is configured to rotate the tissue sample holder between a first position and a second position while in the view operational mode.

5. The biopsy system of claim 1, wherein the user interface further provides a plurality of different user selectable operational modes of the biopsy device, wherein the user interface is in communication with the biopsy device to manipulate the biopsy device through the plurality of different user selectable operational modes, wherein at least one of the user selectable operational modes of the biopsy device includes a sample mode, and wherein at least one of the user selectable operational modes is a non-sampling mode, wherein one of the user selectable operational modes is operable to advance the cutter with respect to the needle without sampling tissue.

6. The biopsy system of claim 1, wherein the user interface further provides a plurality of different user selectable operational modes of the biopsy device, wherein the user interface is in communication with the biopsy device to manipulate the biopsy device through the plurality of different user selectable operational modes, wherein at least one of the user selectable operational modes of the biopsy device includes a sample mode, and wherein at least one of the user selectable operational modes is a non-sampling mode, wherein one of the user selectable operational modes is operable to vary the effective length of a transverse tissue receiving aperture of the needle portion.

7. The biopsy system of claim 1, wherein the user interface further provides a plurality of different user selectable operational modes of the biopsy device, wherein the user interface is in communication with the biopsy device to manipulate the biopsy device through the plurality of different user selectable operational modes, wherein at least one of the user selectable operational modes of the biopsy device includes a sample mode, and wherein at least one of the user selectable operational modes is a non-sampling mode, wherein the needle portion includes a transverse tissue receiving aperture, and wherein one of the user selectable operational modes is operable to provide user selection from a plurality of predefined cutter positions to effectively shorten the length of the transverse tissue receiving aperture.

8. The biopsy system of claim 1, wherein the user interface further provides a plurality of different user selectable operational modes of the biopsy device, wherein the user interface is in communication with the biopsy device to manipulate the biopsy device through the plurality of different user selectable operational modes, wherein at least one of the user selectable operational modes of the biopsy device includes a sample mode, and wherein at least one of the user selectable operational modes is a non-sampling mode, wherein one of the user selectable operational modes is operable to aspirate fluids from a biopsy site.

9. The biopsy system of claim 1, wherein the user interface further provides a plurality of different user selectable operational modes of the biopsy device, wherein the user interface is in communication with the biopsy device to manipulate the biopsy device through the plurality of different user selectable operational modes, wherein at least one of the user selectable operational modes of the biopsy device includes a sample mode, and wherein at least one of the user selectable operational modes is a non-sampling mode, wherein at least one of the user selectable operational modes includes an operational cycle for removing fluids from a biopsy site when the needle portion remains inserted in tissue for a predetermined period of time without a tissue sample being taken.

10. The biopsy system of claim 9, wherein the operational cycle for automatically removing fluids is operable to retract the cutter partially, but not fully, with respect to the needle portion.

11. The biopsy system of claim 10, wherein the operational cycle for automatically removing fluids is operable to apply vacuum through the cutter.

12. The biopsy system of claim 9, wherein the operational cycle for removing fluids from the biopsy site is operable to repeat automatically within predetermined period of time if no further user inputs are provided.

13. The biopsy system of claim 9, wherein the operational cycle for removing fluids from the biopsy site is configured such that the level of vacuum applied during the operational cycle for removing fluids from the biopsy site is less than a vacuum level applied to transport a tissue sample through the cutter to the tissue sample holder.

14. The biopsy system of claim 9, wherein the user interface is configured to override at least one operational mode when the operational cycle for automatically removing fluids is activated.

15. The biopsy system of claim 14, wherein the user interface is configured to override a view sample operational mode when the operational cycle for automatically removing fluids is activated.

16. A biopsy system operable to obtain severed tissue samples from a tissue mass, the biopsy system comprising:
(a) a biopsy device including a needle portion insertable in the tissue mass, a cutter movable with respect to needle to sever a tissue sample from tissue received by the needle portion, and a tissue sample holder for receiving tissue samples severed by the cutter; and
(b) a control module including a user interface, wherein the user interface provides a cutter position indicator configured to depict a position of the cutter relative to the needle during operation of the biopsy device, and a vacuum level indicator configured to depict a level of vacuum corresponding to an actual vacuum level provided to the biopsy device via a vacuum source from a plurality of predetermined levels of vacuum,
the user interface further providing a graphical button, a first adjustment feature, and a second adjustment feature, the graphical button being positioned at a single location on the user interface and being configured to activate both the first adjustment feature for adjustment of the position of the cutter relative to the needle between a plurality of predetermined proximal aperture positions to variably select an effective aperture size_ and the second adjustment feature for adjustment of the actual vacuum level provided to the biopsy device.

17. The biopsy system of claim 16, wherein the user interface further provides a plurality of different user selectable operational modes, wherein the control module is in communication with the biopsy device to manipulate the biopsy device through the plurality of different user selectable operational modes via the user interface, wherein each user selectable operational mode is configured to correspond to a plurality predetermined operational sequences of the biopsy device, wherein at least one user selectable operational mode corresponds to a biopsy mode having a predetermined operational sequence configured to acquire a biopsy sample, wherein at least one user selectable operational mode includes a predetermined operational sequence configured to manipulate the cutter of the biopsy device through a plurality of discrete positions.

18. The biopsy system of claim 16, wherein the user interface further provides a plurality of different user selectable operational modes, wherein the control module is in communication with the biopsy device to manipulate the biopsy device through the plurality of different user selectable operational modes via the user interface, wherein each user selectable operational mode is configured to correspond to a plurality predetermined operational sequences of the biopsy device, wherein at least one user selectable operational mode corresponds to a biopsy mode having a predetermined operational sequence configured to acquire a biopsy sample, at least one user selectable operational mode includes a predetermined operational sequence configured to manipulate the tissue sample holder of the biopsy device through a plurality of discrete positions.

19. The biopsy system of claim 16, wherein the user interface further provides a plurality of different user selectable operational modes, wherein the control module is in communication with the biopsy device to manipulate the biopsy device through the plurality of different user selectable operational modes via the user interface, wherein each user selectable operational mode is configured to correspond to a plurality predetermined operational sequences of the biopsy device, wherein at least one user selectable operational mode corresponds to a biopsy mode having a predetermined operational sequence configured to acquire a biopsy sample, wherein the control module is responsive to the user interface to selectively cycle through each operational mode of the at least three operational modes.

20. A biopsy system, wherein the biopsy system comprises:
(a) a probe having a needle defining an aperture and a cutter configured to translate relative to the aperture of the needle, wherein the probe is configured to acquire biopsy samples from a patient via the needle and the cutter;
(b) a holster, wherein the holster is configured to receive at least a portion of the probe;
(c) a tissue sample holder, wherein the tissue sample holder is associated with the probe and the holster to collect the biopsy samples acquired by the probe, wherein the tissue sample holder includes a rotatable member defining a plurality of cavities, wherein the tissue sample holder is rotatable by the holster to selectively align a selected cavity of the plurality of cavities into communication with the probe; and
(d) a control module, wherein the control module includes a user interface feature, wherein the control module is in communication with the holster to selectively manipulate the probe via the holster, wherein the control module is configured to selectively restrict the cutter of the probe to one of a plurality of predetermined proximal aperture positions relative to the aperture to variably select an effective aperture size, wherein the user interface feature includes an aperture indicator configured to depict the effective aperture size.

* * * * *